US008002465B2

(12) United States Patent
Ahn

(10) Patent No.: US 8,002,465 B2
(45) Date of Patent: Aug. 23, 2011

(54) PATIENT POSITIONING SYSTEM AND METHODS FOR DIAGNOSTIC RADIOLOGY AND RADIOTHERAPY

(75) Inventor: Peter Hyung-Kyun Ahn, Houston, TX (US)

(73) Assignee: Pyronia Medical Technologies, Inc., Great Neck, NY (US)

( * ) Notice: Subject to any disclaimer, the term of this patent is extended or adjusted under 35 U.S.C. 154(b) by 1 day.

(21) Appl. No.: 12/272,966

(22) Filed: Nov. 18, 2008

(65) Prior Publication Data
US 2009/0129556 A1 May 21, 2009

Related U.S. Application Data

(60) Provisional application No. 60/988,838, filed on Nov. 19, 2007, provisional application No. 60/992,111, filed on Dec. 4, 2007, provisional application No. 61/077,150, filed on Jun. 30, 2008.

(51) Int. Cl.
*A61B 6/08* (2006.01)
(52) U.S. Cl. .............................. 378/205; 378/20; 378/65
(58) Field of Classification Search ..................... 378/65, 378/208, 209, 195, 20, 205
See application file for complete search history.

(56) References Cited

U.S. PATENT DOCUMENTS

| 3,565,195 A | 2/1971 | Miller et al. |
| 4,051,380 A | 9/1977 | Lasky |
| 4,262,306 A | 4/1981 | Renner |
| 4,827,763 A | 5/1989 | Bourland et al. |
| 4,830,461 A | 5/1989 | Ishiharada et al. |
| 4,846,173 A | 7/1989 | Davidson |
| 4,905,267 A | 2/1990 | Miller et al. |
| 5,010,772 A | 4/1991 | Bourland et al. |
| 5,315,630 A | 5/1994 | Sturm et al. |
| 5,531,229 A | 7/1996 | Dean et al. |
| 5,564,438 A | 10/1996 | Merchant |
| 5,588,430 A | 12/1996 | Bova et al. |
| 5,595,191 A | 1/1997 | Kirk |
| 5,622,187 A | 4/1997 | Carol |
| 5,693,886 A | 12/1997 | Seimiya et al. |
| 5,727,554 A | 3/1998 | Kalend et al. |
| 5,764,723 A | 6/1998 | Weinberger et al. |
| 5,775,337 A | 7/1998 | Hauger et al. |
| 5,796,059 A | 8/1998 | Boon |

(Continued)

FOREIGN PATENT DOCUMENTS
EP 1795229 6/2007
(Continued)

OTHER PUBLICATIONS

Li, X.A., et al., Technical and dosimetric aspects of respiratory gating using a pressure-sensor motion monitoring system. Medical Physics Jan. 2006; 33(1):145-154.

(Continued)

*Primary Examiner* — Hoon Song
(74) *Attorney, Agent, or Firm* — Saul Ewing, LLP

(57) ABSTRACT

The system provides new ways to ensure that a patient is positioned correctly, e.g. identically with an original planning scan if the patient is to undergo radiotherapy. The system also detects if there is patient movement during a scan. It is an aspect of the present method to immobilize the patient based on a specific site of interest by using positioning sensors that record patient physical orientation based on measurements of patient weight distribution and pressure distribution among other features.

28 Claims, 33 Drawing Sheets

U.S. PATENT DOCUMENTS

| | | | |
|---|---|---|---|
| 5,930,152 | A | 7/1999 | Dumont et al. |
| 5,983,727 | A | 11/1999 | Wellman et al. |
| 6,279,579 | B1 | 8/2001 | Riaziat et al. |
| 6,621,889 | B1 | 9/2003 | Mostafavi |
| 6,826,423 | B1 | 11/2004 | Hardy et al. |
| 6,847,391 | B1 | 1/2005 | Kassatly |
| 6,973,202 | B2 | 12/2005 | Mostafavi |
| 7,030,764 | B2 | 4/2006 | Smith et al. |
| 7,073,508 | B2 | 7/2006 | Moyers |
| 7,117,136 | B1 * | 10/2006 | Rosedale ............... 703/7 |
| 7,199,382 | B2 | 4/2007 | Rigney et al. |
| 2003/0135105 | A1 | 7/2003 | Jack et al. |
| 2005/0085710 | A1 | 4/2005 | Earnst et al. |
| 2005/0228255 | A1 | 10/2005 | Saracen et al. |
| 2005/0234327 | A1 | 10/2005 | Saracen et al. |
| 2006/0004281 | A1 | 1/2006 | Saracen |
| 2006/0262898 | A1 | 11/2006 | Partain et al. |
| 2007/0033735 | A1 | 2/2007 | Formenti |

FOREIGN PATENT DOCUMENTS

| | | |
|---|---|---|
| WO | WO 00/27331 | 5/2000 |

OTHER PUBLICATIONS

Ashruf, C.M.A., Thin flexible pressure sensors. Sensor Review 2002; 22(4); 322-327.

Hamlet, S., Larynx motion associated with swallowing during radiation therapy. International journal of radiation oncology, biology, physics Jan. 15, 1994; 28(2):467-70.

Kooy, H.M., et al., Adaptation and Verification of the Relocatable Gill-Thomas-Cosman Frame in Stereotactic Radiotherapy. International journal of radiation oncology, biology, physics Oct. 15, 1994; 30(3); 685-691.

Gill, S.S., et al., Relocatable frame for stereotactic external beam radiotherapy. International journal of radiation oncology, biology, physics 1991; 20(3):599-603.

Kim S, et al., An Immobilization system for claustrophobic patients in head-and-neck intensity-modulated radiation therapy. International journal of radiation oncology, biology, physics 2004; 59(5), 1531-1539.

Martin J., et al., Treatment with a belly-board device significantly reduces the volume of small bowel irradiated and results in low acute toxicity in adjuvant radiotherapy for gynecologic cancer: results of a prospective study. Radiotherapy and Oncology Mar. 2005; 74(3):267-274.

Koelbl O., et al., Influence of patient positioning on dose-volume-histogram and normal tissue complication probability for small bowel and bladder in patient receiving pelvic irradiation: a prospective study using a 3D planning system and a radiobiological model. International Journal of Radiation Oncology, Biology, Physics 1999; 45(5): 1193-1198.

European search report, issued for 08852317.0, Nov. 5, 2010, Peter H. Ahn.

* cited by examiner

PATIENT POSITIONING SYSTEM AND METHODS FOR DIAGNOSTIC RADIOLOGY AND RADIOTHERAPY

FIELD

The field of the invention relates to targeted delivery of radiation or nuclear medicines for diagnostic or therapeutic purposes, and more particularly targeted delivery by accurately measuring patient position for real time therapeutic and diagnostic radiology.

BACKGROUND

For the delivery of radiation to treat cancer and a few nonmalignant diseases, radiotherapy requires precision in order to deliver more radiation to tumors and avoid excess radiation to normal tissues. Radiotherapy requires prior treatment planning, which involves corresponding diagnostic radiology scans, including, but not limited to, CT, MRI, MRS, PET/PET-CT scan and other nuclear medicine scans including, among others, SPECT and bone scans for precise positioning of the patient. After the planning scan, patients are typically treated with radiotherapy, with every effort to maintain the patient in the original planning position, anywhere from 1 to more than 45 times—often on a once-a-week, daily or twice-daily basis. Recent advancements in increased precision in radiotherapy delivery place great importance on the premise that the patients stay in the same position as during their planning scan(s).

There are 6 or more degrees of freedom in the position of a given part of the body on a day to day and intraday basis while a patient is on a treatment table or diagnostic table (FIG. 1). This includes translational motion in the x, y and z axis, as well as rotational shifts defined as pitch, roll or yaw. The spine is flexible and consists of multiple vertebral bodies; each vertebral body would have 6 degrees of freedom. This would be multiplied by the number of vertebral bodies would be at the same level as the treatment field (e.g., for head and neck radiotherapy, this would commonly extend from the skull, and the C1-T2 vertebral bodies=60 or more degrees of freedom).

Currently, there is no easy way of ensuring that a patient is positioned identically with their original planning scan. If a patient is undergoing or is to undergo radiation therapy, they can be immobilized according to the site of interest. In radiotherapy, in the example of head and neck cancer, this usually entails a custom-made mask for the head and an arch support for the neck. Both head and neck are immobilized onto the treatment table or diagnostic scan table. Tumors of the thorax, abdomen and pelvis may be positioned for treatment by immobilizing the legs and arms, but may require the creation of a rigid and patient-specific mold of the person's anatomy. The patient-specific mold would then be used with every treatment and every planning scan. Following immobilization, a patient is typically positioned with the placement of small pinpoint tattoos or other surrogate reference points on their body. The reference points are then lined up to a reference coordinate system, usually defined by a set of lasers and/or cameras. A set of 2-dimensional radiographs is taken, often on a daily, twice-weekly or weekly basis, in order to verify that a patient is aligned correctly in relation to bony anatomy and soft tissue silhouette.

Radiology or nuclear medicine scans including computed tomography (CT), magnetic resonance imaging (MRI), magnetic resonance spectroscopy (MRS), positron emission tomography (PET/PET-CT), Single Photon Emission Computed Tomography (SPECT), bone scan and other diagnostic scans including angiography are utilized in the diagnosis or in determining the extent of disease. Once disease is established, these or subsequent scans can be utilized to determine the targeting of localized therapies including radiation (radiation treatment planning) or other treatment modalities. If a patient undergoes several scans for purely diagnostic or assessment purposes (not for treatment planning), the position of the area of interest (e.g., an area of tumor that was previously excised with surgery or treated with radiation therapy, or a vascular malformation) is often determined on a patient only with respect to anatomical landmarks instead of with a coordinate system.

With the advent of sophisticated modes of radiation delivery, 2-dimensional radiography as discussed can be inadequate because sophisticated and ultra-precise delivery methods necessitate alignment in 3-dimensional space. This would require that a patient be scanned with either an in-room CT scanner or with a cone-beam CT scanner attached to the treatment linear accelerator, in order to verify the patient's position. However, the process of positioning a patient based on these radiological images is cumbersome, since it requires that many different points of a patient's anatomy be visually compared with that seen in the planning scan. Even if the matching process is automated, visual verification is difficult, especially since different parts of the body (e.g., parts of the spine) may vary in position semi-independently of each other. If a large mismatch is found, then the radiotherapy technician (RTT) or treating physician may prescribe a shift in the radiation or may need to reposition the patient. In such circumstances, obtaining greatest accuracy may entail another time-intensive rescan to verify the patient's position. For diagnostic radiology scans, a patient may be immobilized in the same manner and with the same tools as for radiotherapy (usually in the setting for radiotherapy planning purposes, or for radiology-guided procedures such as biopsy), or may be scanned in the most comfortable or neutral position for the patient on the scanning table with or without immobilizing devices.

Others have attempted to address problems outlined above. Primarily, these solutions have involved a method of imaging a patient more frequently, matching patient contours with a video camera system, or using infrared cameras to track fiducial markers that are attached to the skin. U.S. Pat. No. 4,262,306, U.S. Pat. No. 5,662,187, U.S. Pat. No. 5,727,554 and GB Patent 2,310,792, each of which is incorporated by reference herein in its entirety, teach imaging methods using camera devices to assess and monitor patient position during radiotherapy. U.S. Pat. No. 7,199,382, herein incorporated by reference in its entirety teaches x-ray imaging method to assess and monitor patient positioning. Systems for assessing respiration have used devices that track abdominal movement as a surrogate for respiratory motion, including a marker attached to the abdominal wall that is optically tracked or a belt that a patient wears around the abdomen or thorax containing a single pressure sensor to measure excursion with respiration as taught by U.S. Pat. No. 6,621,881, herein incorporated by reference in its entirety. Currently, there is a continuing unmet need for real time, patient positioning system and position monitoring system that minimizes or eliminates the requirement of time consuming radiology scans in radiotherapy and/or ensures patient positioning during radio-diagnostic procedures by sensing and/or detecting a patient's position during the course of the procedure to allow for current adjustments in patient position in radiation delivery.

BRIEF DESCRIPTION OF THE DRAWINGS

FIG. 3 shows different embodiments of the invention.

FIG. 6a represents the method through which the cycle of respiration, extent of chest excursion or diaphragm position could be determined by the sensor grid(s).

FIG. 9a is a view of a schematic view of the pressure sensors. FIG. 9b is a schematic of the pressure sensor with an adhesive.

FIG. 10 is an embodiment of how sensors could be incorporated in specific areas in a mask of a body contour, in this case the head and neck, for positional verification.

FIG. 16 is an example of a commercially available dental impression 82, mouthpiece, "bite block" or mouth guard. The figure demonstrates a view of the patient's upper teeth and hard palate, looking up from below the level of the patient's mouth.

FIG. 18 is a flowchart which shows a likely implementation of this invention with dental impressions for head immobilization.

SUMMARY

Figure 1:
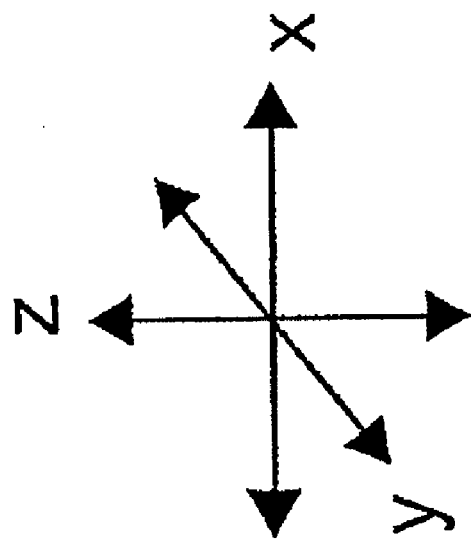
FIG. 1 is schematic representation of a patient's body, demonstrating the 6 degrees of freedom that may be present in any portion of the body.
Figure 1:
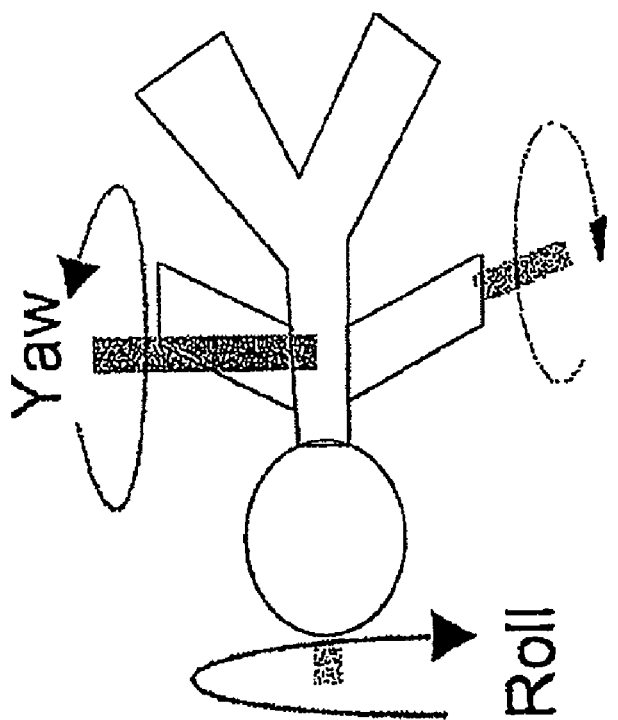

Provided herein is a new system for ensuring that a patient is positioned correctly during radiation therapy. Radiation therapy and diagnostics (RTD), as used herein, is defined to include radiation therapy, radiotherapy, radiodiagnostics, radio-surgery, stereotactic radiotherapy, stereotactic radio-surgery, diagnostic radiology, nuclear medicine and any radiation based procedures that require patient immobilization or monitoring of patient position for delivery and/or detection of radiation in any portion of the electromagnetic spectrum. These terms from time-to-time herein may be used interchangeably as the techniques, methods and devices described herein may be applied to the administration and detection of radiation for diagnostic and/or therapeutic and/or surgical purposes.

The system disclosed herein involves new ways to ensure that a patient is positioned correctly, e.g. identically with an original planning scan if the patient is to undergo radiotherapy. The system also detects if there is patient movement during a scan. It is an aspect of the present method to immobilize the patient based on a specific site of interest by using positioning sensors that record patient physical orientation based on measurements of patient weight distribution and pressure distribution among other features.

The immobilization devices can be any device as are known in the art or any custom or fitted immobilization device. The purpose of immobilization devices is to ensure that the patient remains in the correct position during treatment. In conjunction with those devices, a patient can be first brought into the correct position by using reference lasers for alignment. Several pressure-sensitive sensors may be utilized. Such sensors may be affixed or embedded into the immobilization device. This would be used by the radiotherapy or radiology technician (RTT) and/or physician to further verify patient alignment using this system, in real-time without the need to wait for a rescan.

It is an embodiment of the invention to provide for an improved patient positioning system for precise, accurate and stable alignment of a patient during radiation therapy and diagnostics (RTD) comprising: a patient immobilization device conformed to at least a portion of a patient's anatomy; at least one sensor attached to the patient immobilization device; and an external interrogator device, wherein said immobilization device transmits data to said external interrogator device and said external interrogator device analyzes said data and transmits a control output. The external interrogator device may be the same computer controlling RTD sessions for one or more patients. The external interrogator device may also be a separate control unit, i.e. computer that can be integrated into existing RTD computer systems. The patient immobilization device may be a diagnostic table upon which the patient is positioned, patient formed masks or molds, or other such devices as are known to those of skill in the art.

The method further comprises recording patient position data from a first therapy session in data storage medium and comparing said patient position data from said first radiotherapy session with subsequent radiotherapy session. The first therapy session may be a planning session utilizing a diagnostic radiology or diagnostic radiology-like scanner. The method further comprising interconnecting a patient stabilizer the immobilization device and the external interrogator device and comprises maintaining said treatment position continuously prior to, in the course of and subsequent to each of at least one radiotherapy treatment session(s). The method further comprises manipulating said patient stabilizer to precisely control patient position utilizing directed output from the external interrogator device.

These and other aspects of some exemplary embodiments will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments without departing from the spirit thereof. Additional features may be understood by referring to the accompanying drawings, which should be read in conjunction with the following detailed description and examples.

DETAILED DESCRIPTION

The system disclosed herein comprises pressure-sensitive sensors embedded in an immobilization device that controls and monitors the physical orientation and/or anatomical positioning of patients for the administration of RTD. The invention may include capacitance, resistive, rubber, textile, haptic or piezoelectric sensors and any others as are known to those of skill in the art that can measure physical properties. The measurements are processed in real-time by a computer to accurately determine the precise positioning of a patient undergoing RTD. The sensors of the invention can provide a quantitative measure of the amount of pressure placed on each point on the grid. Individual pressure sensitive sensors may be placed at discrete and/or selected positions on an immobilization device. The sensors may be placed on such device individually, as one or more strips of sensors, or one or more arrays of sensors. The sensors may be placed on a device in any pattern, e.g. linear, rectangular grid, circular, or irregular to measure physical properties. The sensors may be placed at sub-millimeter or other great distances as desired from one another.

The immobilization devices can be any device as are known in the art or any custom or fitted immobilization device. The purpose of immobilization devices is to ensure that the patient remains in the correct position during treatment. In conjunction with those devices, a patient can be first brought into the correct position by using reference lasers for alignment. Several pressure-sensitive sensors may be utilized. Such sensors may be affixed or embedded into the immobilization device. This would be used by the radiotherapy or radiology technician (RTT) and/or physician to further verify patient alignment using this system, in real-time without the need to wait for a radiologic rescan.

It is an embodiment of the invention to provide for an improved patient positioning system for precise, accurate and stable alignment of a patient during radiation therapy and diagnostics (RTD) comprising: a patient immobilization device abutting or conformed to at least a portion of a patient's anatomy; at least one sensor attached to the patient immobilization device; and an external interrogator device, wherein said immobilization device transmits data to said external interrogator device and said external interrogator device analyzes said data and transmits a control output. The external interrogator device may be the same computer controlling RTD sessions for one or more patients. The external interrogator device may also be a separate control unit, i.e. computer that can be integrated into existing RTD computer systems. The patient immobilization device may be a diagnostic table upon which the patient is positioned, patient formed masks or molds, or other such devices as are known to those of skill in the art.

The system may further comprise a patient stabilizer interconnected with the immobilization device and an external interrogator device. The patient stabilizer may be used to adjust patient position either automatically or manually by an RTT. The patient stabilizer may be controlled by the interrogator device when adjustments are determined based on patient position data collected from the sensors.

The system further comprises output which is regulative feedback provided by the external interrogator device to the patient stabilizer or RTT for maintaining a precise initial patient position and an accurate patient position continuously prior to, in the course of and/or subsequent to a radiotherapy or diagnostic radiology session.

The system of claim, wherein said output comprises regulative feedback maintaining a precise initial patient position and an accurate patient position continuously prior to, in the course of and subsequent to each of at least two radiotherapy sessions. The patient stabilizer can be manipulated to precisely control patient position in real time according to output from said external interrogator device. The regulative feedback may further comprise surrogate feedback accounting for respiratory phase or excursion to deliver instructions to turn on or off a radiation therapy unit, correlating to said respiratory phase or excursion, for selectively treating or scanning the body or portion thereof.

The system may comprise a plurality of sensors the plurality may be in arranged individually, in groupings arranged as strip(s), grid(s), ellipse(s) or array, or any irregular shape on a table or flat surface, in a mask or mold of the abdomen and/or pelvis (or any other area of the patient's anatomy as described herein) to assess for patient position.

The one sensor can be removably attached with an adhesive, permanently embedded into said patient immobilization device or a combination thereof.

In one embodiment, the system may comprise selectively delivering radiation to tumors or targets comprising thoracic, abdominal and/or pelvic regions (e.g. tumors in those regions or regions suspected of hosting tumors).

In yet another embodiment, the patient positioning system for precise, accurate and stable alignment of a patient during radiation therapy and diagnostics (RTD) comprising: a head and/or neck immobilization device conformed to at least a portion of the head and neck region of the patient; at least one sensor attached to the immobilization device; and an external interrogator device, wherein said immobilization device transmits data to said external interrogator device and said external interrogator device analyzes said data and provides control output. The system output comprises regulative feedback maintaining a precise initial head and neck region position and an accurate head and neck region position continuously prior to, in the course of and/or subsequent to a radiotherapy session and wherein said output comprises regulative feedback maintaining a precise initial head and neck region position and an head and neck region position continuously prior to, in the course of and subsequent to a radiotherapy session. The system further provides for monitoring verifying the position of a patient's larynx and assessing swallowing status Yet another embodiment of the invention provides for a method for positioning for precise, accurate and stable alignment of a patient during radiation therapy and diagnostics (RTD) comprising: conforming a patient immobilization device comprising at least one sensor to a portion of a patient's anatomy identified for treatment; connecting said at least one sensor to an external interrogator device; interrogating the sensor for a patient position pattern and receiving the patient position pattern by an external interrogator device in real-time; evaluating said patient position pattern by said external interrogator device to determine a treatment position; monitoring said treatment position in real-time; maintaining said treatment position continuously prior to, in the course of and/or subsequent to radiotherapy; and delivering radiotherapy to the tumor or target.

The method further comprises recording patient position data from a first therapy session in data storage medium and comparing said patient position data from said first radiotherapy session with subsequent radiotherapy session. The method further comprising interconnecting a patient stabilizer the immobilization device and the external interrogator device and comprises maintaining said treatment position continuously prior to, in the course of and subsequent to each of at least one radiotherapy treatment session(s). The method further comprises manipulating said patient stabilizer to precisely control patient position directed output from the external interrogator device.

In yet another embodiment the monitoring step of the method comprises accounting for respiratory phase and delivering instructions to turn on or off a radiation therapy unit, correlating to said respiratory phase or excursion, for selectively delivering radiation to a patient. In another embodiment the monitoring step further comprises verifying the position of a patient's larynx and assessing swallowing status.

In yet another embodiment, the method further comprises delivering radiotherapy to tumors selected from the group consisting of thoracic, abdominal, pelvic, skull, extremity, head and neck tumors.

The system may include pressure sensors used directly on the patient table without a separate patient immobilization device for RTD scanning, wherein is potentially less material interfering with the path of a radiotherapy beam or allowing a patient to be scanned in a small bore scanner such as in an MRI machine in a reproducible position, wherein the need for one or more sessions of radiographic confirmation (orthogonal films, CT, etc.) of patient position prior to radiotherapy treatment may be obviated, permitting decreased overall treatment time and therefore allowing more patients to be treated on a radiotherapy machine on a given day. Additionally, the system may permit decreased positional uncertainty and allow smaller planning margins for this uncertainty, decreasing the exposure of normal tissue to radiation.

There are other systems for verifying patient position. Those systems include methods of imaging a patient more frequently, matching patient contours with a video camera system, or using infrared cameras to track fiducial markers that are attached to the skin. U.S. Pat. No. 4,262,306, U.S. Pat. No. 5,662,187, U.S. Pat. No. 5,727,554 and GB Patent 2,310,792, each of which is incorporated by reference herein in its entirety, teach imaging methods using camera devices to assess and monitor patient position during radiotherapy. U.S. Pat. No. 7,199,382, herein incorporated by reference in its entirety teaches x-ray imaging method to assess and monitor patient positioning. The system disclosed herein has a number of advantages over such systems.

It is an advantage of the system to permit the use of an immobilizing device for the head and neck, such as a thermoplastic mask, while assessing for head and/or neck movement beneath the mask or mold at multiple points during therapy and allowing for real time automated adjustment of RTD and/or patient positioning. Other proposed systems only look at one part, such as the head, while ignoring the neck, or do not use an immobilizing device in this area, which introduce setup uncertainties and complexities. The system provides a multiplexed approach for easy patient positioning. Camera, infra-red, laser tracking or s-ray systems largely preclude the use of anterior immobilization devices. Therefore, for head and neck RTD, for example, the inability to use an anterior mask results in challenges in consistently positioning patients. It is a feature and advantage of the system disclosed herein to provide for consistent, accurate and precise patient positioning because the system does not rely on the imaging of patient contours which would be obscured when using typical immobilization devices. Moreover, camera systems can be blocked by physical obstacles including the radiotherapy unit gantry head or may be challenged by the use of small bore MRI machines for example. Because soft and hard tissue pressure and weight distribution is assessed in the present method, such challenges are over come by the system and method disclosed herein.

The system allows for real-time assessment of patient motion during an RTD session or diagnostic radiology/nuclear medicine scan. Current methods of ensuring accurate patient setup, such as taking a single CT image before and/or after a patient receives radiation therapy, take only a snapshot of patient movement. The system described here provides an output which may be assessed numerous times before, during, and/or after radiotherapy treatment or during the diagnostic scan by a computer-based system that correlates patient weight and pressure distribution to position.

The system assesses patient weight loss based on the pressure that each immobilized part of the body places on the immobilizing device(s). This would therefore be an indication of whether a patient would need to be re-planned for radiotherapy, since a consistent decrease in exerted pressure against the immobilizing device could be an indicator of severe weight loss. The system can also automatically adjust RTD based on an analysis of patient weight-loss determination and positional variation. Because the system measures soft tissue and bone (hard and soft pressure points), the effect that a patients weight loss or tumor shrinkage may have on typical imaging systems is minimized since this system does not only rely on the soft pressure points of skin contours.

The system allows a radiation therapist (RTT) or diagnostic radiology/nuclear medicine technician to change a patient's position with respect to the immobilizing devices based on real-time measurements of pressure being applied against the sensor(s). This would help ensure that a patient's head, torso or other body part is always in the same position with respect to the anterior and/or posterior immobilizing device(s), and would not require or decrease the requirement for a time-consuming confirmation with an imaging scan including CT.

Typically, the abdomen is used as a surrogate for respiratory movement, and anterior abdominal compression devices are often utilized to minimize respiratory movement during RTD. While the compression decreases movement with respiration, it does not eliminate it. Unlike other respiratory gating systems, the system described here can permit the use of respiratory gating in situations in which the abdomen is compressed.

The system allows the use of pressure-measuring sensors arranged individually, in groupings arranged as strip(s), grid(s), ellipse(s) or array, or any irregular shape in a mask or mold of the abdomen and/or pelvis (or any other area of the patient's anatomy as described herein) to assess for patient position as well as respiration.

The system further reduces patient positioning variation between simulation sessions for radiotherapy and sessions for radiation therapy, between sequential radiotherapy sessions, between simulation sessions for radiotherapy and any diagnostic tests, and between diagnostic radiographic sessions which require that the patient be placed in as similar a position as possible. In some embodiments, the system can eliminate the need for simulation or planning scans, or repeat planning scans. In RTD, the system would decrease variation in daily patient positioning, therefore having utility in RTD administered via photon or gamma-rays, electron beams, with heavy ions including carbon ions, with proton or neutron particles, or any other forms of radiation. The system may be used to permit a technician to align a patient in a neutral position on the treatment planning or initial diagnostic scanning table, which the patient could more comfortably replicate in future sessions or could be used irrespective of the anticipated need for any future scan or treatment. This may or may not also involve using the invention to align a patient with the spine and body directly parallel to the longitudinal or any other axis of the table.

The system provides for readings at one or multiple parts of a patient's body, which allows verification and adjustment of flexible parts of the body with respect to each other. Further adjustment can be made so that a rigid relationship between flexible parts of the body to each other can be reliably reproduced on a daily basis.

The system also takes readings in real-time, which allows monitoring of patient motion during RTD or diagnostic radiology scans. In RTD, one application could be to ensure that there is no intrafraction movement before, during, and after treatment with a conventional or IMRT multi-field plan, as well as with treatment using arc radiotherapy (e.g. conventional or IMRT) or tomotherapy. This can also be used to ensure that there is no intrafraction motion during stereotactic radiosurgery. In diagnostic radiology or nuclear medicine scans, this can be used to measure the amount that a patient moves during a scan and correlate this measured result with the resulting images, or reprocess the scan to delete those images when patients were moving or out of position.

Patient chest and/or abdominal excursion can also be tracked during respiration and can turn the radiotherapy machine on and off depending on the phase of respiration, inside or outside the setting of anterior and/or side abdominal compression. This includes tracking of the differential pressures exerted by the chest and/or abdomen on the anterior, side, or posterior portions.

In another embodiment, the system can determine if the patient has maintained their weight, lost weight or gained weight between radiotherapy treatments in the portion of the anatomy being measured. This may be useful in determining when a new radiotherapy plan may need be to generated to compensate for changes in patient anatomy that accompany weight changes. The system can further make and/or suggest changes in a radiotherapy plan to compensate for changes in patient anatomy.

Sensors

The pressure-measuring sensors of the system can be spaced less than a millimeter or up to several centimeters or more apart from each other. A number of different sensors, including capacitance, resistive, piezoelectric sensors or others as are known in the art can be used to measure the pressure or weight exerted on a small area; capacitance sensors can be preferred. These sensors can be used individually, or connected together to create a strip, array, or grid of sensors. These sensors may be pliable or rigidly placed in relation to each other, allowing a strip or array of these sensors. In one embodiment, these sensors can be attached to a deformable or rigid device by a technician. In another embodiment, these sensors can be embedded into the material of the immobilization device (e.g. radiation textile, polymeric, etc.). Individual pressure sensors, strips, arrays or grid(s) of these sensors, using one of a number of the available technologies, including capacitance, resistive, rubber, textile or piezoelectric sensors, can be used to provide a quantitative measurement of the amount of pressure placed on each sensor. The sensors can be connected together to create a strip, array, or grid of sensors. The sensors may be pliable or rigidly placed in relation to each other; this allows the sensors to be attached to either a deformable or irregularly-shaped device, or flat on a hard table. In a preferred embodiment, the sensors are attached to a flat, hard table and on the immobilization device that isolates a patient's anatomy for RTD.

Radiotherapy of Head and Neck

In the case of head and neck radiotherapy, it is common practice to create a mold or thermoplastic mask that conforms to the unique contours of a particular patient's head and/or neck, and which is then indexed to the treatment or diagnostic radiology table. Typically, a low-temperature thermoplastic deformable sheet material is used to form the mask. However, with the side effects of chemotherapy and radiation include nausea and irritation in the mouth, there is often a large degree of weight loss in the middle of treatment. A patient's head and neck will often become loose with the weight loss, and with the loss of the tight fit in the mask there may unanticipated movement. A patient may swallow in the middle of treatment or during a diagnostic scan, or the position of the larynx may change as daily treatment proceeds. Currently, no easily available and noninvasive manner exists in which to determine when a patient swallows.

Dental clay or other hardening molds are typically available for non-invasive head and neck positioning to restrict patient movement during treatment. The molding material hardens on a polyethylene mouth plate, forming a permanent impression of the teeth. With the teeth positioned in the hardened mold, the maxillae and to some extent the mandible, not soft tissue, is immobilized for positioning. Such devices are non-invasive; however, they do not provide repeatable, accurate and precise position to minimize over administration of radiation to a patient. Such devices include Bite•Bloc™ sold by Best Medical located in Springfield, Va., by way of example, not limitation.

Radiotherapy is often administered as a definitive or post-operative therapy in head and neck cancers. Additionally, a related form of radiation therapy, stereotactic radiosurgery (SRS), utilizes large and ablative doses of radiation to benign or malignant tumors or blood vessel formations in the cranial area, usually in single but possibly in several or more sessions. The high doses of radiation administered during each session necessitate extreme precision in the targeting and treatment of the tumor or malformation due to the close proximity of many important structures in centers of the brain and other areas of the head and neck.

In order to target and treat these structures with high doses of radiation, it is often necessary to limit the extent of positioning uncertainty to the sub millimeter level. Such levels of immobilization are possible with invasive stereotactic frames that are attached by a neurosurgeon to the patient by inserting several screws through a rigid frame, which are then drilled through the skin into the patient's bone. Due to the need for the patient to be immobilized in the same position during the treatment as during the planning scan, the patient often has the frame attached in the morning followed by the planning scan, after which the patient must continue to have the frame attached for a time period of several hours to the entire day, after which they would receive treatment in order to be able to precisely reproduce the position of the target between the scan and the treatment, after which the invasive frame can be removed.

Methods of patient immobilization for SRS and stereotactic radiotherapy (SRT) that do not require such invasive, labor-intensive and inconvenient techniques for patients are available, including but not limited to the Gillman-Thomas-Cosman (GTC) and University of Florida (UF) methods. These methods contain components including a rigid frame which are attached to the treatment table and to the patient, a custom-made dental impression mouthpiece onto which a patient bites, and certain methods include a custom thermoplastic mask These methods have been demonstrated to have large variations in patient positioning often on the order of 2 mm or more between scan and treatment sessions (when submillimeter precision is required). The variance in patient position often precludes the use of such methods for SRS. However, they provide sufficient immobilization for SRT, and have been demonstrated to provide improved immobilization for daily fractionated radiotherapy in cancers of the head and neck, although still not to an ideal extent.

In yet another embodiment of the invention described herein provides for the placement of the pressure-measuring, electronic sensors into a mouthpiece attached to a rigid frame. The addition of a thermoplastic mask and/or a posterior neck rest or a custom-made mold of a patient's posterior neck or posterior portion of their skull can be provided. The mask or posterior immobilization devices may or may not contain similar electronic sensors as described herein. The use of electronic, real-time pressure sensors in the mouthpiece would be novel and would be utilized to increase the level of precision in patient positioning between any two radiology, nuclear medicine or angiography scans, as well as between any scan and any radiotherapy or other treatment.

Immobilizing mouthpiece-based verification system using one or multiple pressure sensors, including but not limited to capacitance, resistive, rubber, textile, piezoelectric, or piezoresistive, when used for radiation therapy, including but not limited to photon or gamma-rays, electron beams, with heavy ions including carbon ions, or with proton or neutron particles, stereotactic radiosurgery, fractionated stereotactic radiotherapy, or a diagnostic radiology/nuclear medicine scan, including but not limited to fluoroscopy, CT fluoroscopy, CT, MRI, MR-spectroscopy, PET/PET-CT, SPECT, stereotactic cerebral angiography, provide advantages as explained throughout this disclosure.

In one embodiment, sensors can be used individually, in strip(s), grid(s) or array on a rigid mask conformed to a patient's head, facial, neck, shoulder, torso, pelvic and/or extremity contours to assess whether a patient's mask is loose or needs adjustment and to assess alignment of a patient in relation to the immobilizing device for RTD and/or diagnostic radiology/nuclear medicine scans between any two days or within one session. The system can be used to pause and/or adjust the treatment or diagnostic machine if the patient moves out of position during the treatment or scan. The system allows for real time adjustment of the radiation or patient position while RTD is suspended.

In an embodiment of the system, pressure/weight-measuring sensors can be used individually, in strip(s) or grid(s) placed on a mouthpiece onto which a patient clamps in order to improve immobilization for a diagnostic scan or a therapeutic modality, including but not limited to RTD. The invention can be used to assess in real-time or after-the-fact, whether a patient's skull is in the same position as that recorded during an initial planning scan on a subsequent diagnostic or planning scan or a subsequent treatment that is performed in the same position as the initial scan or reference treatment. The patient's position can be shifted in real-time to match their position during an initial reference scan for treatment or for a subsequent scan using the invention.

In another embodiment, the sensor(s) can be placed on a rigid mask conformed to the patient's neck, and be used to verify the position of a patient's thyroid cartilage, cricoid cartilage and larynx and therefore assess swallowing status before, during and/or after radiotherapy or during a diagnostic radiology/nuclear medicine scan. The system can send a signal to pause a radiotherapy machine from treating a patient while a patient is swallowing or not swallowing, or to associate diagnostic radiology or nuclear medicine scan images with whether a patient was swallowing or not or to the phase of their swallowing.

In another embodiment, the sensor(s) of the system are placed on the mouthpiece used for patient immobilization and can monitor a patient's skull position before, during and/or after radiotherapy treatment. If the system detects that a patient has moved out of position during a scan or treatment, it can be used to temporarily pause the treatment machine or diagnostic scanner, during which time a therapist can reposition the patient to the correct position. The treatment or scan can then be continued or can be integrated with automated pressure repositioning devices to automatically reposition patients.

In another embodiment, the mouthpiece containing the invention can be used in conjunction with other forms of reproducible, noninvasive immobilization that are used for stereotactic diagnosis or treatment.

In those cases in which the mouthpiece is not rigidly attached to the treatment table or to the floor in the treatment or diagnostic scan room, the sensors can be in place to measure the amount of pressure that the patient is using to bite on the mouthpiece. The sensor embedded mouthpiece can be attached to a scanning apparatus to improve reproducibility, as it permits greater confidence that change in position of the mouthpiece is related to movement of the skull as opposed to opening of the jaw.

The sensor embedded mouthpiece embodiment can be used with other embodiments disclosed herein in the immobilization for diagnostic planning scanning or radiotherapy, or other treatment modalities, that encompasses the skull, head and neck for cancers or other diseases of the head and neck area. This system can improve immobilization and reproducibility of position of the neck during stereotactic or fractionated daily treatments. Treatments may space a single session, two sessions or more, or even 40 or more sessions using this system.

The embodiments may include a mouthpiece sensor which can modify standard immobilizing devices, mouthpiece attached to a rigid frame or other device, for the head and neck and/or skull that already achieve 2 mm or smaller variations in patient positioning. The addition of the quantitative, electronic pressure sensor(s) in the mouthpiece provides even improved immobilization. In this context, it may permit the use of this noninvasive form of immobilization with the mouthpiece with or without a standard thermoplastic mask and/or standard posteriorly-based immobilization devices for stereotactic radiosurgery for certain targets in the brain in which currently only an invasive frame can be used. This would greatly improve patient comfort, as there would be no penetration of the patient's skin and the patient would not have a wait for hours with a frame immobilized onto their head until they received treatment.

The system can be used with any current frameless stereotactic radiosurgery method that is available, can incorporate the use of a mouthpiece to assist in the immobilization, and does not preclude the use of other standard immobilizing devices, such as thermoplastic masks or molds of the face or anterior neck, immobilizing devices such as neck-rests or molds of the posterior skull or posterior neck, unlike other devices that have been proposed for improvement in patient immobilization in this region of the body.

It is an embodiment of the system that it provides for real-time assessment of patient motion. Currently, invasive head-frames are necessary for stereotactic radiosurgery since otherwise a patient can move without the treatment physician being aware, with disastrous consequences given the high doses of radiation given in a single fraction. Using the sensors integrated into or attached to the mouthpiece that the patient is biting on, with or without sensors in other areas of the head or neck, the system would automatically assess for any change in the pressure placed on the system and turn off the scanner or treatment machine if the patient moves out of place.

The system provides for the use of stereotactic cerebral angiography to be used in planning for radiotherapy and stereotactic radiosurgery of vascular malformations, since the invention would be used to assure reliable and noninvasive patient immobilization during the angiogram as well as during subsequent scan(s) and treatment(s).

The system can assess for treatment response with the use of a stereotactic coordinate system during scan(s) or angiogram(s) taken after treatment, including 3D angiography. This would allow a direct and accurate comparison of the pre-therapy tumor or malformation with the post-therapy result, since the attainment of an accurate and reproducible immobilization system would permit the use of a coordinate system to define the exact position of the target with respect to a reference point or points.

Other, non-anatomically based radiographic systems such as bone scan or any imaging modality with radio-labeled markers that use PET, SPECT, or other nuclear medicine imaging can be integrated with the system described herein to overlay and integrate the results with an anatomically-based imaging system such as CT or MRI scan.

Custom-made impressions of the patient's teeth, gums or palate or floor of mouth can be used with a generic bite block. If both mandibular and maxillary impressions are made, an electronic pressure sensor can be placed in between the two impressions, in order to measure the total bite pressure. The sensor enhanced mouthpiece can be combined or not combined with the pressure sensors used in other parts of the standard immobilization apparatus, the use of this invention provides for greater confidence that the actual delivery of radiation is closer to that intended during the original planning scan. With this more accurate delivery of radiation, this permits smaller margins for error and decreases irradiated volumes and decreases toxicity of radiation.

The system described herein in its various embodiments allows for immediate and accurate determination of patient position during, before and/or after, RTD. This allows more rapid correction and verification of the performed correction than other methods that require repeat imaging where the technician needs to leave the room, take a time-consuming scan, return and make corrections based on those scan(s).

Radiotherapy of the Abdomen, Thorax, Pelvis and/or Extremities

For radiotherapy of areas of the abdomen, thorax, and/or pelvis, another embodiment of the system herein described can utilize pressure sensors not only in the posterior aspect of the patient's body, but on the anterior portion and integrated into device(s) used for immobilizing part of the body.

In one embodiment, the device can assess respiratory motion and allow provisions for diagnostic scans that associate scan images with phase of respiration, or control an RTD device to treat only at specific phases of the respiratory cycle.

For radiotherapy and stereotactic radio-surgery of areas of the thorax, abdomen and/or pelvis, respiration may or may not lead to large variations in movement of normal tissues (lung, liver, retroperitoneal organs, prostate, etc) up to 3 cm or more, and may therefore need to be accounted for in patient undergoing radiotherapy. One approach to account for respiratory motion is allowing free breathing, but placing a surrogate of motion on the patient's abdomen; this has been shown to correspond with respiration and can be used to control either the device that delivers radiotherapy (turning it on or off), or the diagnostic radiology or nuclear medicine scanner in which a set of images is associated with a specific phase of the respiratory cycle or excursion. The other approach to radiotherapy or stereotactic radiosurgery in these areas is to decrease the motion with breathing as much as possible. This is performed either with having the patient hold their breath, or by having a device that compresses the abdomen.

In one embodiment, an array of sensors aligned in grid(s) or strips(s) on a table or contour-based posterior mold can be used to assess and improve alignment of a patient on a radiation therapy or diagnostic radiology/nuclear medicine table.

In another embodiment, the pressure-measuring sensor grid(s) or strip(s) can be used to measure patient movement in real-time and to assess movement before, during, and/or after radiation therapy or diagnostic radiology/nuclear medicine scan.

In yet another embodiment, the pressure/weight-measuring sensors aligned in grid(s) or strips(s) can be used as a surrogate for respiration and therefore be used to turn a radiation therapy unit on or off to more selectively treat thoracic, abdominal and/or pelvic tumors or be used on a diagnostic radiology/nuclear medicine scanner to associate specific scan images, with respiratory phase or amount of chest or abdominal excursion and/or diaphragmatic position.

In one embodiment, system can verify that abdominal compression is being performed consistently between any two days in which a radiation therapy session and/or diagnostic radiology/nuclear medicine scan is being performed.

In another embodiment, the sensor(s) can be attached to a rigid abdominal compression device and can take measurements to create a surrogate for cycle of respiration and/or diaphragmatic position. Therefore, the invention can be used to adjust an RTD machine in order to more selectively treat thoracic, abdominal and/or pelvic tumors according to respiratory phase and/or excursion or selectively scan for diagnostic purposes. The system can automatically adjust the RTD machine by turning the machine on and off in phase with a patient's respective cycle or excursion. The system can also modify the quality of the radiation to account for patient respiration. The system can also modify the intensity, focus, size and/or shape of the radiotherapy beam, or be used on a diagnostic radiology/nuclear medicine scanner to associate specific scan images and phase of respiration, chest and/or abdominal excursion or diaphragmatic position.

Prone Positioning for Radiotherapy

In most cases, the patient is positioned on the table in the supine position (i.e. on their back) for diagnostic radiology or nuclear medicine scan, radiotherapy planning or radiotherapy treatment session. However, patients may also be scanned or treated in prone position (lying face-down on the table). In radiotherapy applications, this can involve prone breast treatment. This consists of an elevated platform on top of the scanning or treatment table, with an opening through which the treated breast falls through to increase the distance between the treated breast and the adjacent lung and heart. Additionally, patients are commonly treated or scanned in prone position with a belly board that contains an opening through which the abdominal contents including a significant portion of the intestines can pass through via gravity, decreasing the volume of sensitive organs (e.g., intestines) that are exposed to high doses of radiotherapy when the pelvis or lower abdomen is irradiated. Although this technique is most often used in treatment of rectal cancer with radiotherapy, it has also been used in gynecological cancers and may be used in cancer of any other abdominal or pelvic site. Disadvantages of positioning patients on their abdomens in prone position consist largely of inconsistency in day-to-day patient positioning, and patient motion as the abdomen moves in and out with patient respiration.

Multiple prone breast devices are commercially available; each system can provide for positioning a patient to separate treated and untreated portions of the body as far away from each other as possible to minimize side effects of radiotherapy. Although prone positioning is often advantageous in pushing normal tissues away from the radiation beam in select cases, there are questions concerning positional consistency when patients are positioned in this manner. In the example of prone breast radiotherapy, there are issues with consistent patient positioning, as it is critically important to keep the untreated breast away from the radiation beam (FIG. 19), especially if there are day-to-day variations in patient translational or rotational setup. Consistently immobilizing the contralateral, untreated breast is difficult to do since the untreated breast is compressed and out of view of the radiation therapist, and therefore subject to day-to-day variations in translational and rotational positioning. As part of the utility of this invention, pressure sensor(s) can be arranged individually, in grids or in arrays and affixed or integrated onto standard patient positioning devices for prone breast radiotherapy. These pressure sensor(s) may be placed anywhere on the patient positioning devices, although the sensor(s) can be preferably placed most commonly on areas of the elevated immobilizing device underlying the contralateral untreated breast, as well as under the abdomen and the arms (FIG. 20). In common practice, a wedge may be placed underneath the contralateral, untreated breast in order to rotate the patient even further; pressure sensors can also be placed on this wedge as well, for purposes of ascertaining untreated breast position throughout the treatment course.

Other embodiments of the utility of this invention in prone therapy include the use of the pressure sensors in patients who are positioned in prone position for any other body site, including to the cranium or to the abdomen or pelvis. Besides treatment of the breast in prone position, patients are often treated in prone position for treatment of rectal cancer. Using a similar setup as the prone breast board, a commercially available prone belly board or customized vacuum bag would be affixed with pressure sensor(s) 58/60 arranged individually, in grids, or in arrays. These would be arranged using the same technique as outlined for prone breast and other body sites, with the pressure sensor(s) strategically placed on the treatment table and/or elevated immobilizing devices underlying portions of the patient's body with which the table or immobilizing device(s) come into direct contact.

For prone breast radiotherapy and diagnostic scanning as well as in other treatment or scanning sites, the change in pressure readings on the sensors as a patient breathes in and out may be tracked, and used to determine the phase of a patient's respiration. This may be used in similar manner to other embodiments of respiratory gating described elsewhere in this application for patients in the supine position, with the information on the phase of breathing using the quantitative pressure sensor measurements utilized to place the images into different bins that represent different phases of the respiratory cycle, chest/abdominal excursion or diaphragmatic position, or to gate radiotherapy treatment so that radiation beams are turned on only during specific phases of the respiratory cycle, chest/abdominal excursion or diaphragmatic position. Similar to the applications described with patients in supine position, the sensors may be used to track patient movement during treatment, and correspondingly send a signal to the treatment or scanning machine that may be used to turn off the radiotherapy beam or diagnostic scanner if a patient moves out of position.

The pressure sensors may also be used in patients who are positioned for diagnostic scanning, radiotherapy planning or radiotherapy treatment in the decubitus position, in which the patient on the side, either on the flat table or with a customized immobilization device. This positioning technique is commonly used for patients scanned or treated to manipulate normal tissue in relation to the area of interest that is being scanned or administered radiation. The application of the sensors is the same as that described for the other commonly used positions: use in initial positioning of the patient, monitoring and tracking of patient movement during the scan or treatment, as well as monitoring and tracking of patient respiration during treatment. Interpretation of data from the sensors may be used to output a signal to the scanning or radiotherapy machine, which may be used to pause the scan or the treatment.

Prone and decubitus positioning, with the patient on their side, also has advantages in terms of diagnostic imaging, largely due to the same advantages of pulling the breast or other structures of interest away from the rest of the body. The pressure sensors may also be used in these applications in radiographic or nuclear medicine imaging of these structures while the patient is laying on their side or is on their abdomen. The pressure sensors may be used for respiratory gating, as described elsewhere in this application.

DETAILED DESCRIPTION OF THE DRAWINGS

Now turning to the drawings where the embodiments described herein are more fully explained. Where reference is made to reference numerals, such reference numerals are used consistently in each of the figures.

FIG. 1 is schematic representation of a patient's body, demonstrating the 6 degrees of freedom that may be present in any portion of the body. In total, there are thousands if not tens of thousands of degrees of freedom since each portion of the body is related semi-independently of any other portion.

Figure 2:
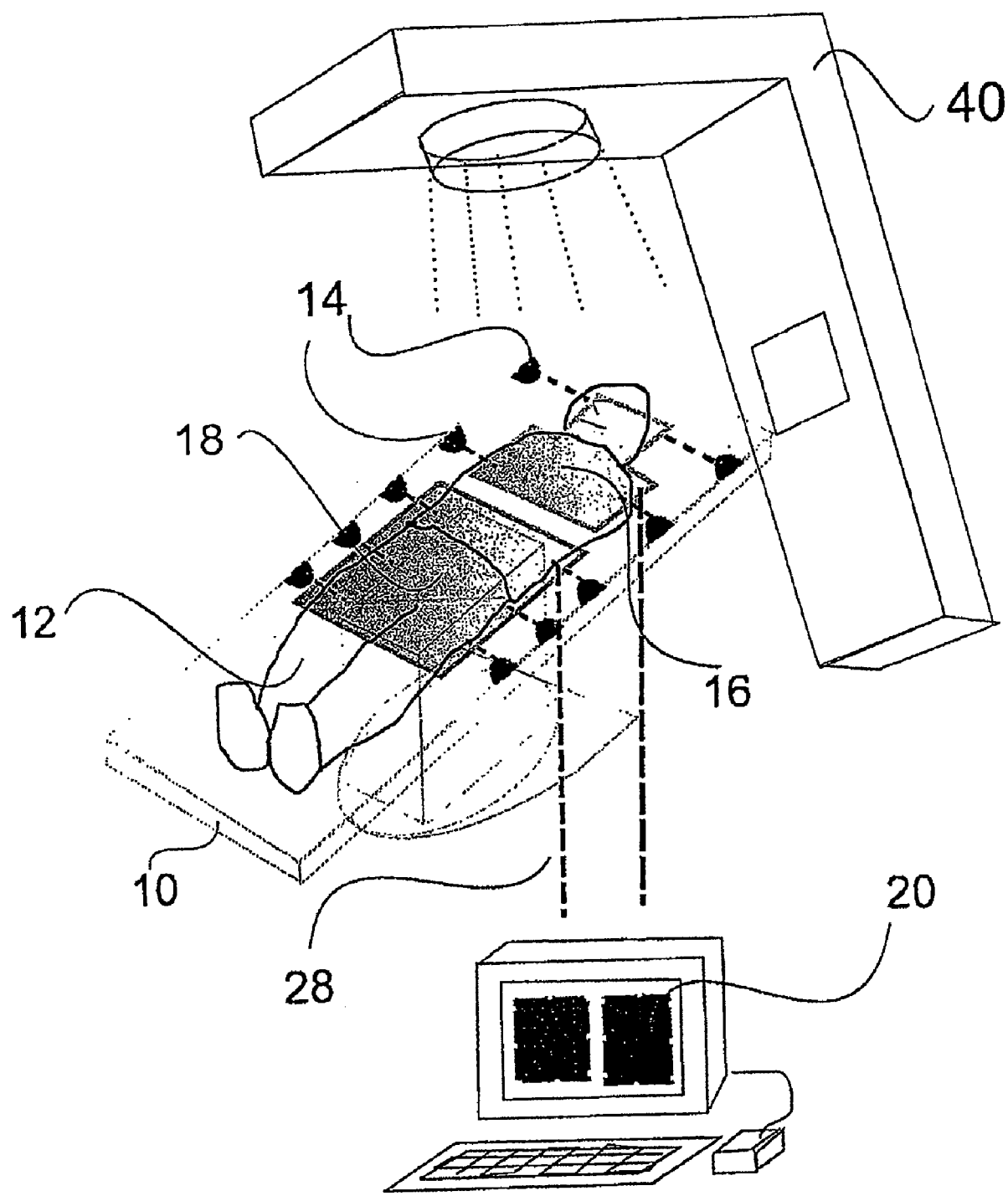
FIG. 2 is a perspective view of a patient on a treatment table for radiotherapy treatment, with a patient lying on a table with a grid of pressure-sensitive devices.

FIG. 2 is a perspective view of a patient on a treatment table for radiotherapy treatment, with a patient lying on a table with a grid of pressure-sensitive devices.

The system and device to reduce variability in patient positioning and/or to track respiratory motion is described here. In FIG. 2, a grid of weight-bearing pressure sensors 18 is to be placed on top of a table 10 onto which the patient 12 is positioned by the RTT or radiology technologist. The grid 18 shown below is rectangular and is placed underneath the patient's pelvis and abdomen, but it can also be square, an array of sensors arranged in one or several strips, an ellipse, curved or irregularly shaped 16 in any dimension and can be placed under the entire body or a relevant portion of the body. In this example, another grid 16 is simultaneously attached to or incorporated onto the table at the same time as the first grid, at the level of the head, neck and upper thorax. 1 or more sensor grids may be used at the same time. If not directly incorporated into the table, the pressure-measuring grids are directly or indirectly attached to the table via rigid supports which are attached to connectors 14 at the sides of standard radiotherapy or diagnostic radiology tables which may consist of divots, hooks or other interfacing connectors. The table may be manufactured with one or more of the pressure-measuring grids already incorporated. In the example given here, the table and patient are attached to a linear accelerator 40 for radiotherapy treatment, although a diagnostic radiology, angiography or nuclear medicine scanner may be used instead. An electronic output is generated by the pressure-sensitive grids in real-time and sent electronically to one or more computers 20 inside and/or outside the treatment room. On day 1, the output is stored representing a snapshot of the patient's position during that day. On subsequent days, the weight pattern from the original diagnostic or planning scan is recalled and compared with the current weight pattern as measured by the identical sensor grid(s) setup. The RTT or radiation technologist may then shift the patient's position based on this real-time comparison.

FIG. 3 shows different embodiments of the invention.

Figure 3A:
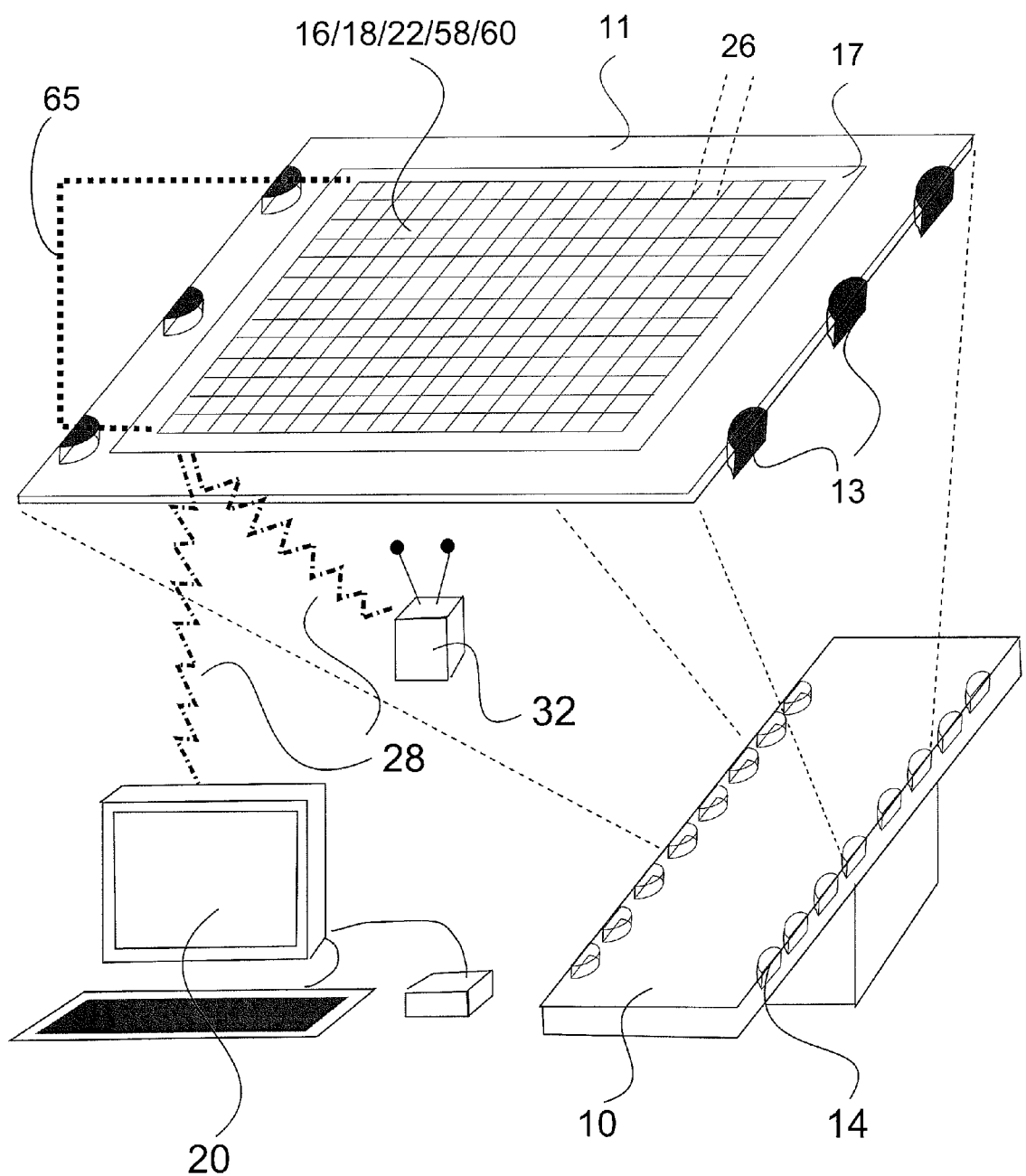
FIG. 3a is a view of a representative mat, containing a commercially-available pressure-measuring grid of sensors, immobilized on a flat surface.

FIG. 3a is a view of a representative mat, containing a commercially-available pressure-measuring grid of sensors, immobilized on a flat surface.

FIG. 3a represents a close-up drawing of the pressure sensors to be placed directly or indirectly onto the treatment or diagnostic scanning table or onto a mask or mold that conforms to any portion of a patient's body contour. The sensor array could be regularly shaped 18 such as in a rectangular configuration shown here, or irregularly 16 shaped (not shown) on a rigid backing, regularly or irregularly shaped on a flexible backing 22 to be placed on the table or customized or noncustomized immobilization device placed on the table (not shown), a sensor 58 constaining a single sensing element with a flexible or rigid casing placed on a mask or mold overlying the patient, or a sensor array 60 containing multiple sensing elements with a flexible or rigid casing placed on the mask or mold. Each sensor array or grid 16/18/22/58/60 consists of one or more individual sensing elements 26 which are adjacent to each other. The grid contains a number of sensing elements 26 which are spaced apart from each other anywhere from a submillimeter distance to tens of centimeters from each other, dependent on the limits of the particular technology used to measure pressure. Typically, each sensing element 26 will be spaced approximately 1-2 mm apart from each other (defining its resolution), but may be spaced closer or further apart. The sensor array is contained in a casing 17 which may be rigid or flexible. In this example, the sensor array with its casing is integrated or attached to a rigid board 11 which is attached via a connector 13 to a receiving connector 14 on the treatment or scanning table 10. The sensor arrays have outputs (wired or wireless) 28 which attach to a computer 20 that stores, displays and/or interprets the data which is sent. The data from the each sensing element 26 of pressure-measuring device 16/18/22/58 or 60 may or may not be sent to an ancillary device 32. The sensor(s) will face the patient's skin. FIG. 9b represents the backing of the pressure-measuring array or grid of sensor(s). Any mode of attachment of the sensor or sensor grid(s) may be used to attach the device to the mask or mold of the patient's body contour or to the table, including an adhesive or mechanical connector 59 that attaches to the mask, mold or table material. In the drawing presented here, an adhesive or other connector 59 is present in the backing of the rigid or flexible casing 17 containing the pressure-measuring sensors. It may be applied by the technician on the day the mold or mask is conformed to the patient's body contour, or it may have an adhesive or other backing applied at time of manufacture.

Figure 3B:
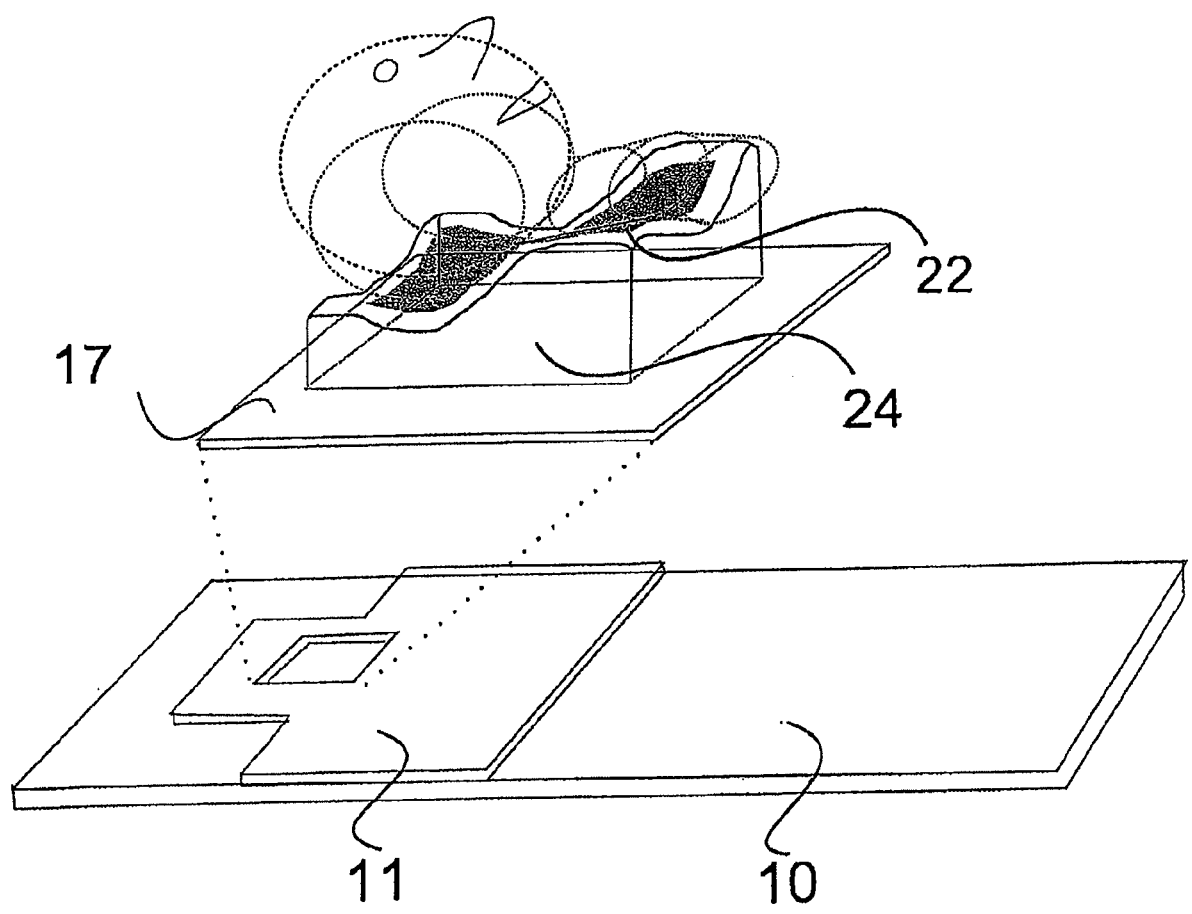
FIG. 3b is another view of the table and patient head and neck positioned on a neck-rest.

FIG. 3b shows the grid of pressure-mapping structures incorporated onto an irregular shape, which represents common immobilization devices used in radiotherapy. This is an example of a neck rest which may be a standard shape or customized to the particular patient, commonly used to help immobilize the neck in radiotherapy and in a diagnostic/planning scan for head and neck tumors, with the invention incorporated.

Figure 3C:
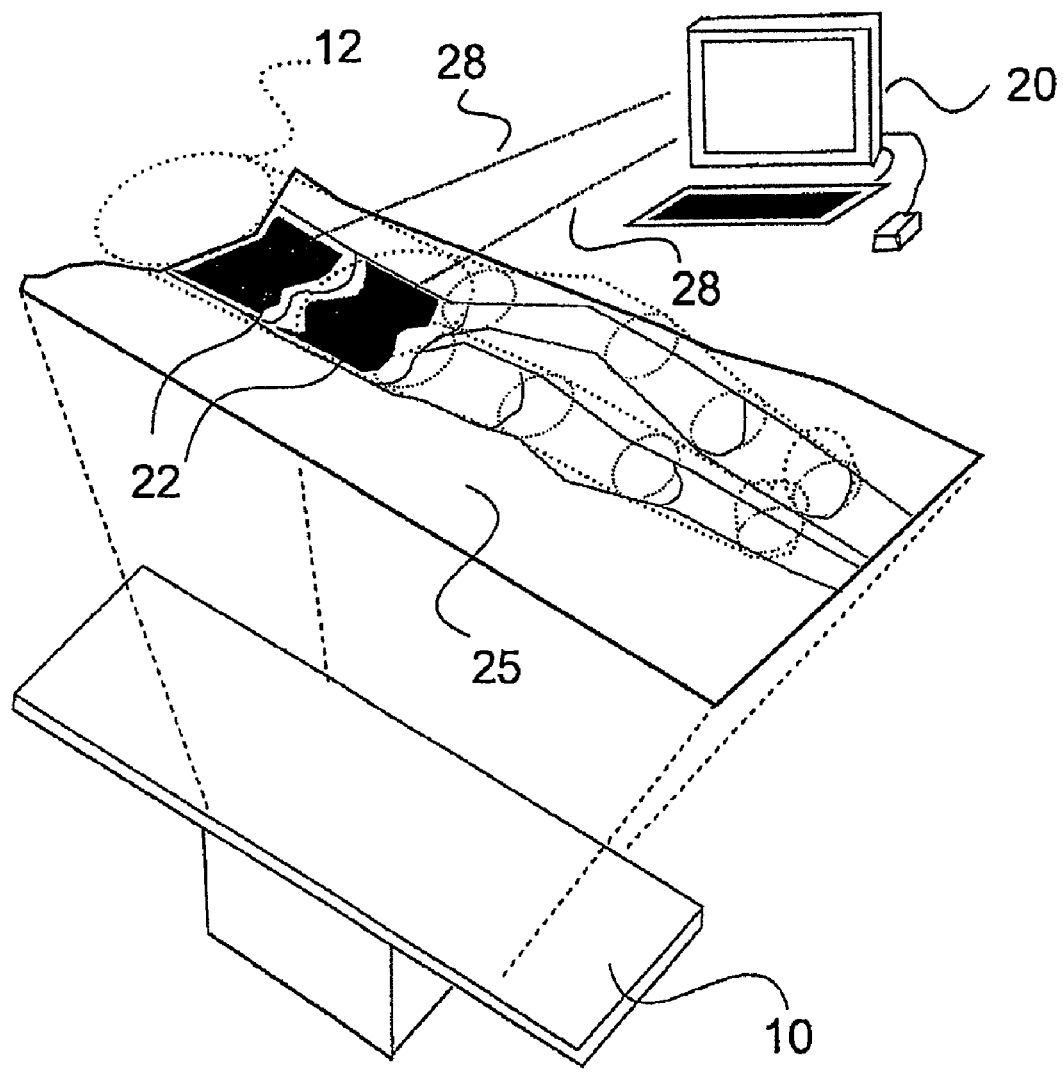
FIG. 3c shows an alpha-cradle or Vac-lok that are commonly used for immobilization for thoracic, abdominal, and/or pelvic tumors.

FIG. 3c shows an alpha-cradle or Vac-loc that are commonly used for immobilization for thoracic, abdominal, and/or pelvic tumors. It incorporates a grid or strip(s) of pressure-sensing elements.

FIG. 3 demonstrates applications for placement of representative sensor grids. One common embodiment—FIG.

3a—is a flat grid which would be immobilized onto the treatment table or would be incorporated as part of the table at manufacture. This particular mat 18 is immobilized against a flat surface (by stretching, or with prior incorporation of sensors directly into a flat board which are then rigidly hooked or slotted onto the radiotherapy, diagnostic radiology or nuclear medicine table). The grid could be regularly shaped 18 such as in a rectangular configuration shown here, or irregularly 16 shaped (not shown). The grid contains a number of sensing elements which are spaced apart from each other anywhere from a submillimeter distance to tens of centimeters from each other 26, dependent on the limits of the particular technology used to measure pressure. Typically, each sensing element 26 will be spaced approximately 1-2 mm apart from each other (defining its resolution), but may be spaced closer or further apart. The edges of the grid contains hooks, projections or other connectors 13 that attach to fasteners, indentations or other connectors 14 incorporated into the table. The grid is attached to a device that transmits by electrical signal 28 via a wire or via a wireless communication device to a receiving device 20 and/or 32. Due to the plasticity of the sensing elements, a regularly or irregularly shaped flexible grid containing the pressure sensors 22 can also be incorporated into or rigidly affixed to an irregularly shaped surface such as a head and neck rest 24 as represented in FIG. 3b. In FIG. 3b, the irregularly shaped surface shown below is curved 24 and is used to place a patient's neck for head and neck radiotherapy treatments, but the surface can be irregularly shaped in any dimension or manner. FIG. 3c represents the placement of the pressure-sensing grid in a mold such as a Vac-Lok (CIVCO, Kalona, Iowa) or alpha-cradle (Smithers Medical, North Canton, Ohio) 25 that is customized to conform to a contour of the pelvis, abdomen, or any other part of the body. Any customized reusable or one-time mold may be used. The sensing elements in a flexible 22 or rigid 16/18 backing (not shown) may be manufactured already incorporated as part of this mold that conforms to a portion of the patient's body including the head and/or neck, chest, abdomen, pelvis or extremity or it may be placed on top of the mold after its manufacture and fixed into place (either before or after the mold has been conformed to the patient's body contour). The multidimensional array of measured pressure values is then outputted to the display and computer 20 or directly to a storage device. The frequency of the measurement and communication would depend on the application. The communication can be performed as a snapshot once during the procedure, or it can be performed in real-time with the array of values being communicated (depending on the limit of the technology, up to hundreds of times a second), displayed and stored as an array of time-stamped values. Typically, if cycle of respiration, chest/abdominal excursion, diaphragmatic or other patient motion is being measured then the values of the measured array would be communicated in real-time several times a second. At the time of first imaging or first radiotherapy treatment, a snapshot of the values generated in the array are saved to create a reference for future comparison. This snapshot will typically be taken at the time the patient passes through the scanner. At the time of subsequent imaging or treatment session, a technician will align the patient 12 (whose original weight-bearing blueprint will have been saved on the receiving device), and will manually compare these results with the original weight-bearing pattern or this comparison will be automated (see FIG. 5). This technique will therefore allow the patient to be aligned properly with respect to both translational shifts as well as rotational shift in pitch, roll or yaw in relation to the treatment or diagnostic table, as well as any other immobilizing device.

One or multiple sets of grids may be placed on either the table or other immobilizing device, and the electronic results are stored and compared with the reference values taken on the initial measurement session.

Figure 4:
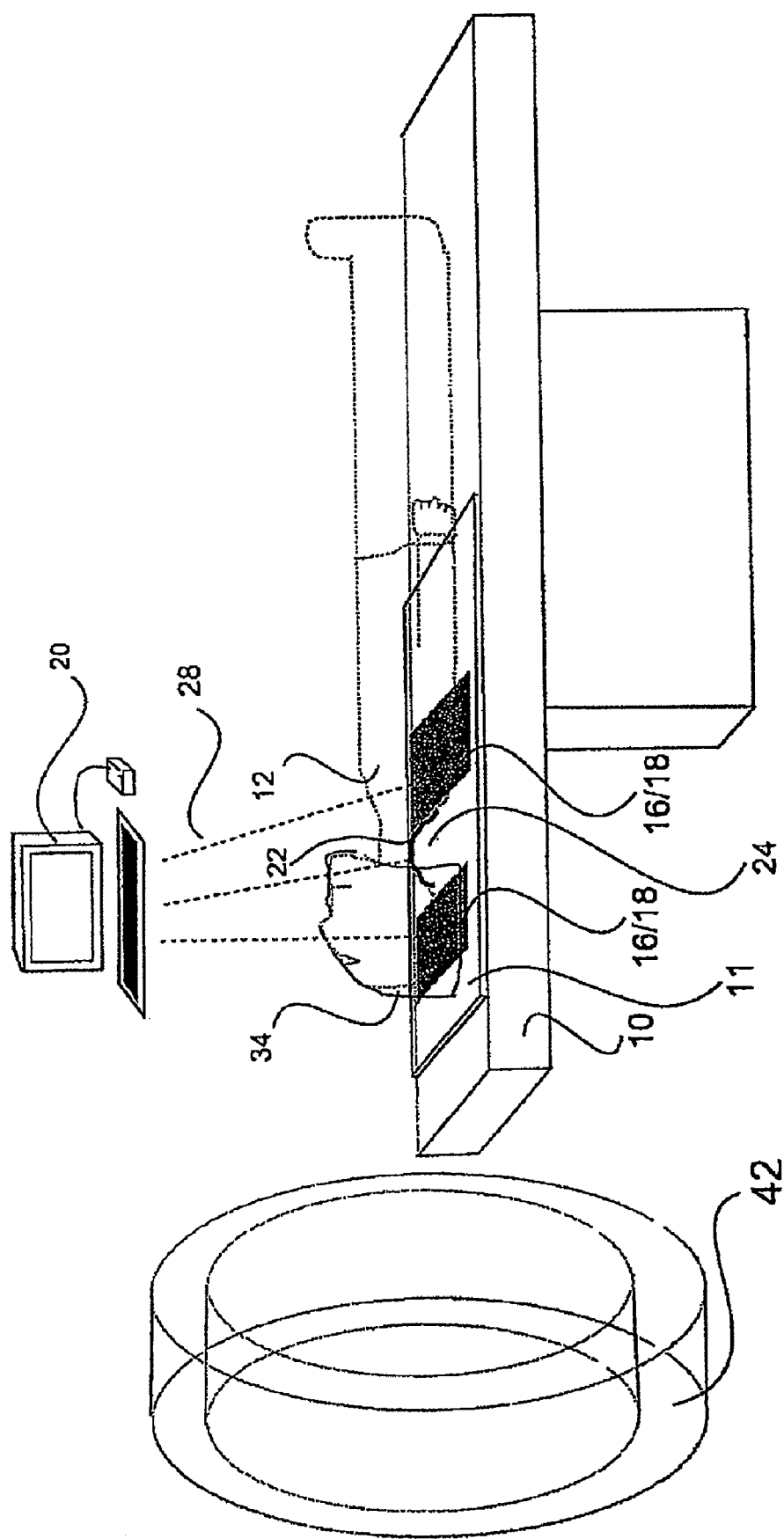
FIG. 4 is a side view which shows a patient immobilized for treatment for head and neck radiotherapy or scanning for diagnosis or radiotherapy planning, with the pressure-sensing grids or strips of sensors in place.

FIG. 4 is a side view which shows a patient immobilized for treatment for head and neck radiotherapy or scanning for diagnosis or radiotherapy planning, with the pressure-sensing grids or strips of sensors in place.

FIG. 4 represents an example of how a patient 12 being treated with or planned for radiotherapy or positioned for diagnostic scanning of the head and neck might be positioned using this system. A rigid mask 34 which is conformed to the patient's facial and/or neck contours is placed onto the patient. As is standard commercial practice, the mask may extend to the upper neck in which case there are separate shoulder pulls as used in common practice (not shown), or the mask may extend down to the shoulders. The mask may be kept in place as is common practice, or it may be omitted with the use of the sensor grid(s) on the neck/headrest and/or shoulder pulls. At the region behind the patient's neck, there is a curved surface which supports the neck 24. Although this is commonly used in practice, it may be used or may be omitted in this case. The neck and head-rest, if used, incorporates a grid or several strips of pressure-sensitive sensors 22 affixed or incorporated onto this irregularly shaped surface. The sensor grid(s) can be directly incorporated into the neck and head-rest at the time of manufacture, or it may be stretched onto and/or affixed immediately before the patient is scanned for radiotherapy planning (see FIG. 3b). The head and neck rest is directly locked onto place on the table 10 or locked onto place on a board 11 which itself locks into place on the table, as is common commercial practice. Each of the elements in the grid or strip(s) can individually register the pressure that is placed upon them and outputs the registered values electronically to a device 20 or 32 via a signal 28 and displayed using the method noted in FIG. 5.

Figure 5:
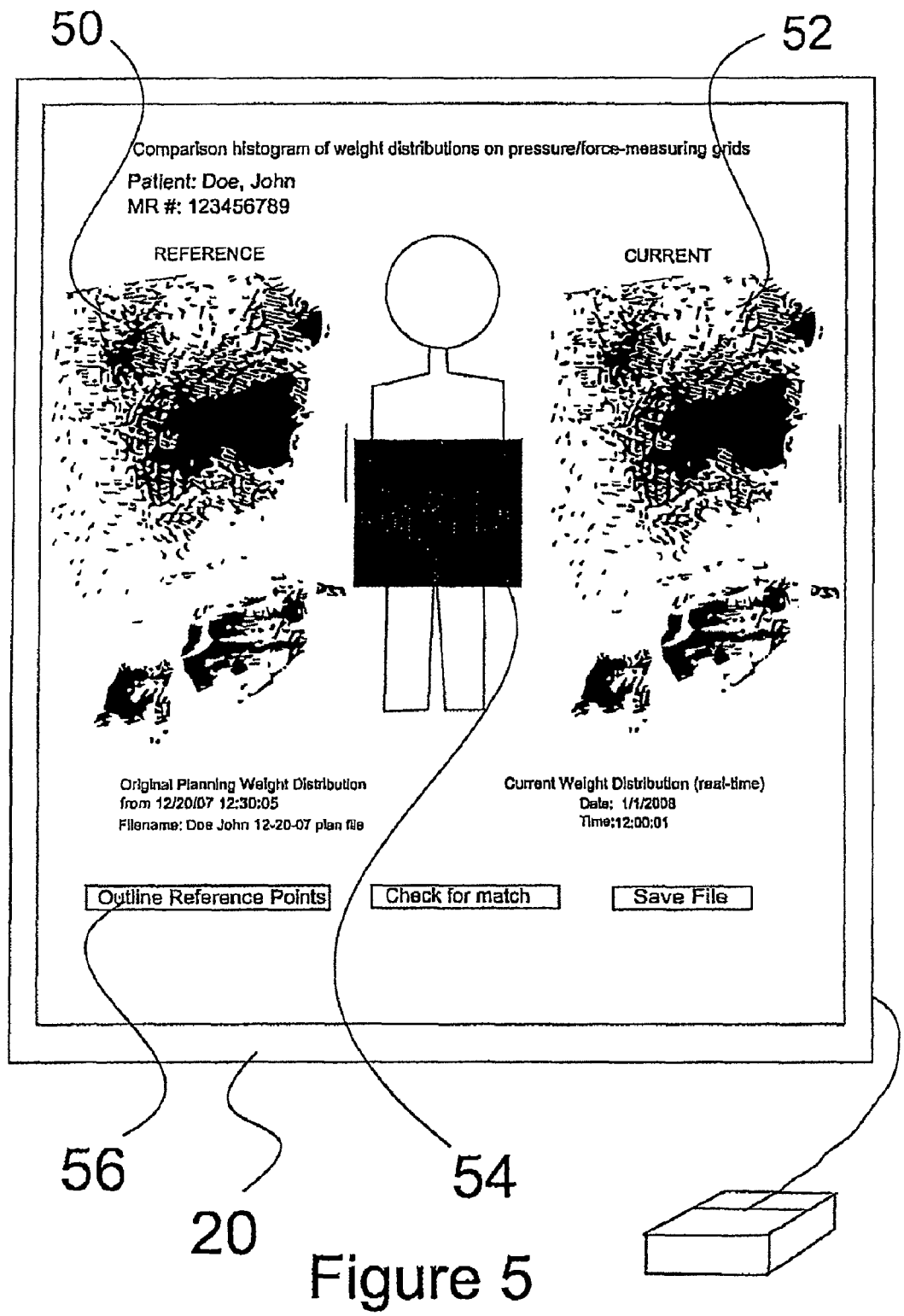
FIG. 5 is a sample view of the screen that a therapist or physician uses with an output from the invention to ensure that the patient's position is matched with the position during the original, planning scan.

FIG. 5 is a sample view of the screen that a therapist or physician uses with an output from the invention to ensure that the patient's position is matched with the position during the original, planning scan. The display may differ in actual practice, but the spirit of this illustration will be retained.

FIG. 5 represents a sample output which is displayed on the monitor of computer 20, which are connected to the grid(s) or strip(s) of pressure sensors. On the example given in this figure, the monitor on the left 50 is a 3-dimensional histogram which represents the pressures exerted on each sensor on the grid(s) saved on the computer, representing the pattern of weight-bearing that the patient had during the original scan and which is used for baseline comparison. The amounts of pressure exerted on the grid can alternatively be represented on a 2 dimensional grid containing numerical pressure measurements or with colors, with the different colors representing the amount of pressure exerted on each sensor (e.g., one color would represent a low amount of measured pressure, and another color would represent a larger pressure load, with gradations of color in between). The image on the right 52 demonstrates the patient's current, real-time pattern of weight distribution on the sensors grid(s), which is compared to the prior, saved pattern 50. The software may also identify spots which represent peaks of pressure, which may represent areas of bony anatomy which are focally pressing on the sensor grid(s) or strip(s). This may be used as reference points or areas (summoned by the operator pressing button 56 on the screen) to assist in aligning a patient with the reference pattern by outlining the stored 50 pressure peak(s) on the real-time measurement 52, and/or using automated algorithms to instruct the user to shift or rotate the patient in a specific direction or along a specific axis. Bony anatomy can provide valuable data, as it would not change with tumor shrinkage or patient bone loss, and would be used in conjunction with lower pressure points representing the skin contour. Any portion of the visual representations 50 52 may be magnified on screen to focus on any region of interest. A diagram which may or may not be included is a representation 54 of the position of the grid(s) or strip(s) in relation to the patient's body. In this case, this demonstrates that the grid of pressure sensors are placed beneath the abdomen, pelvis and upper legs, although the sensors may be placed under any part of the body and thus represented on screen. This may be preprogrammed into the computer by the manufacturer and selected by the operator at the time of initial planning or diagnostic scan.

FIG. 6 is a side view of a patient to be treated for daily fractionated pelvic, abdominal or thoracic radiotherapy or extracranial stereotactic radiosurgery. The patient in this example is immobilized with an anterior abdominal/thoracic immobilizing device, and the pressure sensor grid(s) being used to assess for respiratory motion.

Figure 6A:
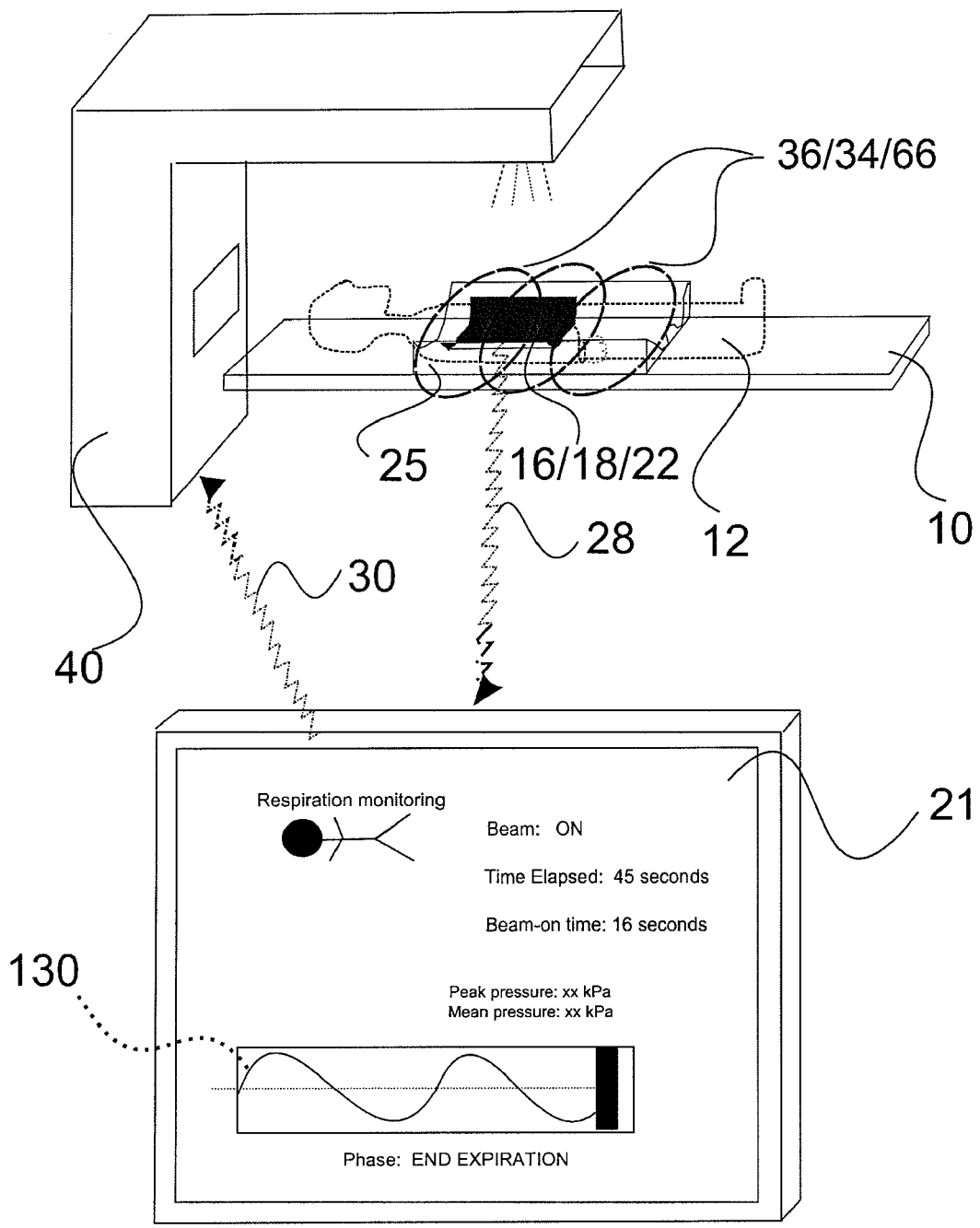
FIG. 6a is a side view of a patient to be treated for daily fractionated pelvic, abdominal or thoracic radiotherapy or extracranial stereotactic radiosurgery.

FIG. 6*a* represents the method through which the cycle of respiration, extent of chest excursion or diaphragm position could be determined by the sensor grid(s) 16/18/22 or strip(s), and used to gate radiotherapy treatment or control the diagnostic scanning machine according the phase of respiration. This is in addition to its function in ensuring proper, consistent patient alignment. In this case in monitoring respiration for radiotherapy purposes—the thorax, abdomen and/or pelvis is being treated. A Vac-Lok, alpha-cradle or other mold 25 may be conformed to the posterior contours of the body. A set of sensor grid(s) 16/18/22 or sensor strips(s) is incorporated into the flexible shell of the mold at time of manufacture or added on by the user prior to use by the patient. Alternatively, a flat sensor grid 16/18 may be placed directly on the table behind the patient without the use of a mold. For additional immobilization, there is the option of wrapping a commercially available, plastic or other flexible material 36 around the patient, with a vacuum seal created that encompasses the anterior part of the body and immobilizes it via compression such as with the BodyFix system. An alternative embodiment is that the material above the table 10 or mold 25 used for anteriorly-based patient immobilization is a rigid material or thermoplastic mask 34/66, without any vacuum seal. The pressure sensor grid(s) may be used in the context of this or other anterior and/or side immobilization devices to verify patient position and for respiratory gating, and may also be incorporated into these immobilization devices 34/36/66 as will be demonstrated in other figures. After the patient 12 is immobilized, their position is changed and verified using the sensor grid(s) or can be stored for future reference if taken during a diagnostic or planning scan. After correct positioning is confirmed, the system is switched to a respiratory monitoring mode 21, in which signals representing the patient's pattern of pressure and weight-bearing are used as a surrogate marker for respiratory motion and respiratory phase. At the time of planning scan or initial diagnostic scan, a movie with time-stamped snapshots of weight-bearing patterns representing the changes in the pattern of weight-bearing (pressure) with respiration is stored. As a patient breathes, there are changes in chest and/or abdominal excursion and expansion during the respiratory cycle which translates into changes in weight-bearing placed on sensors at levels of the thorax and/or abdomen, and this will be measured. With inspiration, more measured pressure will be exerted by the body on the sensor grids placed underneath the thorax as well as the abdomen; this effect will be magnified if there is anterior compression for patient immobilization, although this is not necessary to perform respiratory monitoring and/or gating. With breath expiration and decreased chest excursion and decreased expansion as air exits the lungs, there will be decreased measured pressure placed on the sensor grids. One method of respiratory gating will be essentially similar to the software component used by RPM (Varian Medical Systems, Palo Alto, Calif.) and other similar commercial systems. Each respiratory cycle will be divided into 5-20 or more equally-spaced patterns of weight-bearing, with a typical segment number of 10. In a case where the measured respiratory cycle is 5 seconds and the decision is made to divide the cycle into 10 segments, sensor patterns would be recorded every 0.5 seconds. If the patient is being planned for radiotherapy, each 0.5 second interval would be associated with a set of scan images, as used in current respiratory gating techniques for radiotherapy planning. The physician or therapist would then identify one, several, or any of these segments as portions of the respiratory cycle in which certain parameters are met (i.e., decreased target, normal organ, or tumor movement with respiration). Most commonly, this will be the end-expiratory phase where movement of thoracic and intra-abdominal organs with respiration is minimized. Any subsequent scans (pre-therapy, post-radiation therapy) can be performed with respiratory gating, in which images from these scans (CT, MRI, MRS, PET, PET-CT, SPECT, etc.) would be associated with sets of images that are associated with the respiratory-gated bins. The weight-bearing pattern that corresponds with a specific phase of the respiratory cycle (expiration, inspiration, etc.) can then be recalled during subsequent radiotherapy sessions or diagnostic imaging. Based on the signal 28 received from the sensor grid(s), this can be used to interface with the radiotherapy 40 or diagnostic scanning machine 42 (not shown) with a signal 30. For radiotherapy, this would be used to turn the radiation beams on or off according to the phase(s) of the respiratory cycle 130 that have been preselected to treat the patient—in which there is the least amount of movement with respiration. While the RPM and similar systems use one surrogate on the abdomen or chest, this system can use one or multitude of points over or underlying the abdomen and/or thorax for monitoring respiration. In the setting of extracranial stereotactic radiosurgery or stereotactic radiotherapy in which abdominal compression is utilized, the commercially-utilized surrogate of abdominal motion is difficult to obtain. This method may therefore have utility as a surrogate for respiration in that setting, as well as in the setting of conventional fractionated radiotherapy. For diagnostic radiology and nuclear medicine studies, the sensor grid can be used to associate a set of images with each phase of the respiratory cycle for comparison with the prior diagnostic radiology or nuclear medicine scan.

Figure 6B:
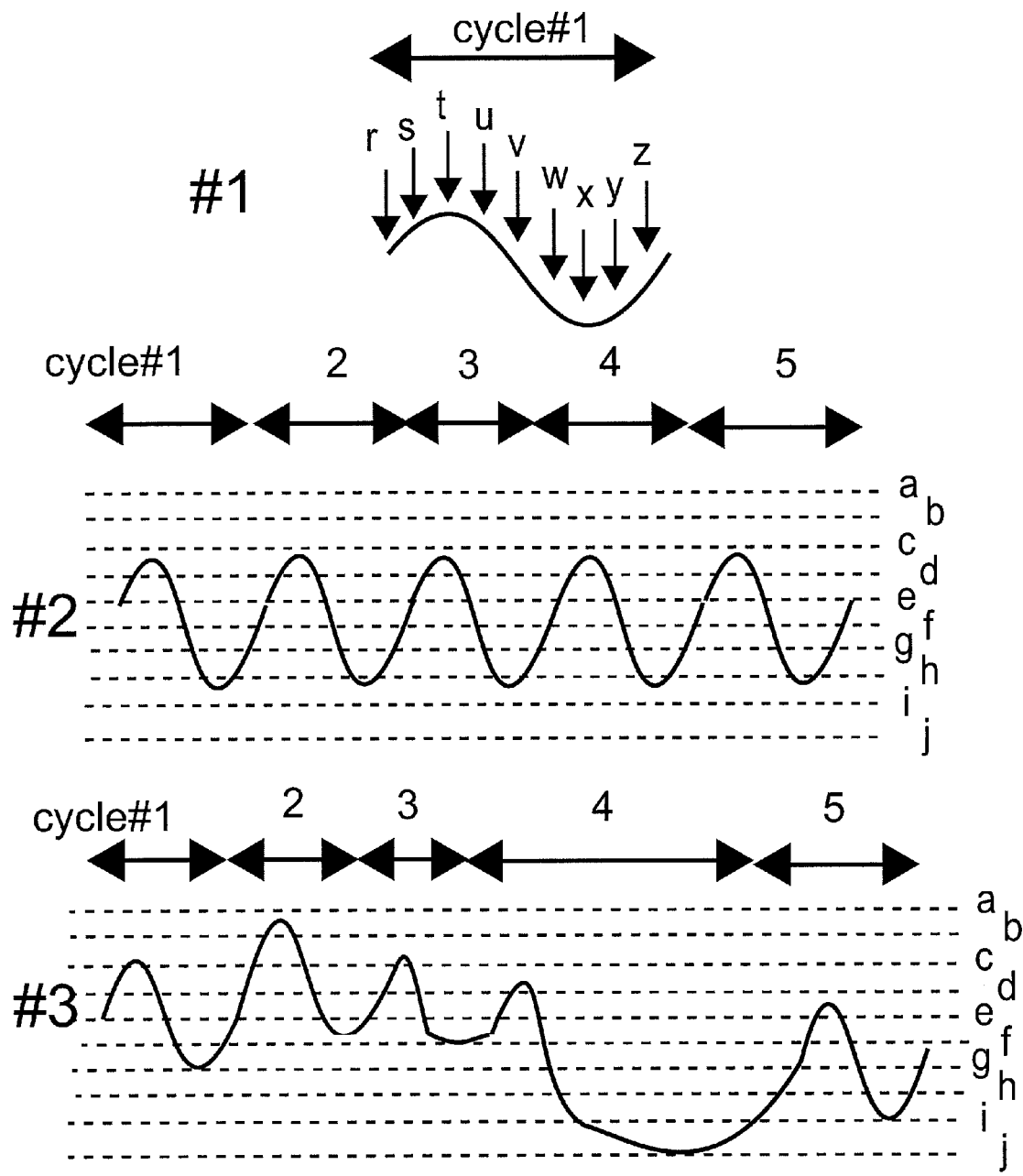
FIG. 6b is a pictoral representation of the respiratory cycle (in FIG. 6a) as well as an alternate utility using respiratory excursion.

FIG. 6*b* is a pictoral representation of the respiratory cycle (130 in FIG. 6*a*). The respiratory cycle 130 is shown as a sine wave about a constant axis (waveform #1) divided into segments r to z, with t representing breath inspiration and x representing breath expiration and forming the basis of most respiratory gating techniques. If the patient breathes completely regularly and with the same amplitude, one may see a respiratory cycle 130 that appears as waveform #2. However, this is often not the case; instead, the patient often takes shallow or deep breaths, and may hold their breath (waveform #3; a is maximum inspiration, while j is maximum expiration). Instead of looking at the respiratory cycle, one may look at the absolute extent of chest/abdominal/diaphragm excursion (letters a through j, vertical axis) with or without the context of phase of the respiratory cycle (letters r through z, horizontal axis). Instead of using only the relative position on the respiratory wave (chest excursion, abdominal movement or other surrogate) about the sinusoidal wave to determine phase of the respiratory cycle, the measurements from the pressure sensors can also be used to determine the exact amount of chest or abdominal excursion, and therefore gate the scan or therapy according to this absolute surrogate. This does not preclude also using the relative position on the respiratory wave or phase. The acquisition of images for a diagnostic or planning scan, or gating for radiotherapy treatment, may occur only at predetermined levels of respiratory excursion. This may be more accurate, since the amount of organ displacement with respiration depends upon the amount of chest, abdominal or diaphragmatic excursion. Use of the pressure sensors is also compatible with breath-hold techniques, in which the respiratory monitoring mode 21 can be used to monitor a patient as they hold their breath while they are being scanned or treated. In that case, the sinusoidal line 130 shown in the figure would approximate a straight horizontal line, and if this monitoring deviated from the desired amount of excursion represented by straight line the treatment or scan would be delayed. This can be used instead of or in conjunction with other breath-hold devices such as Active Breathing Control (Elekta, Stockholm, Sweden).

Figure 7A:
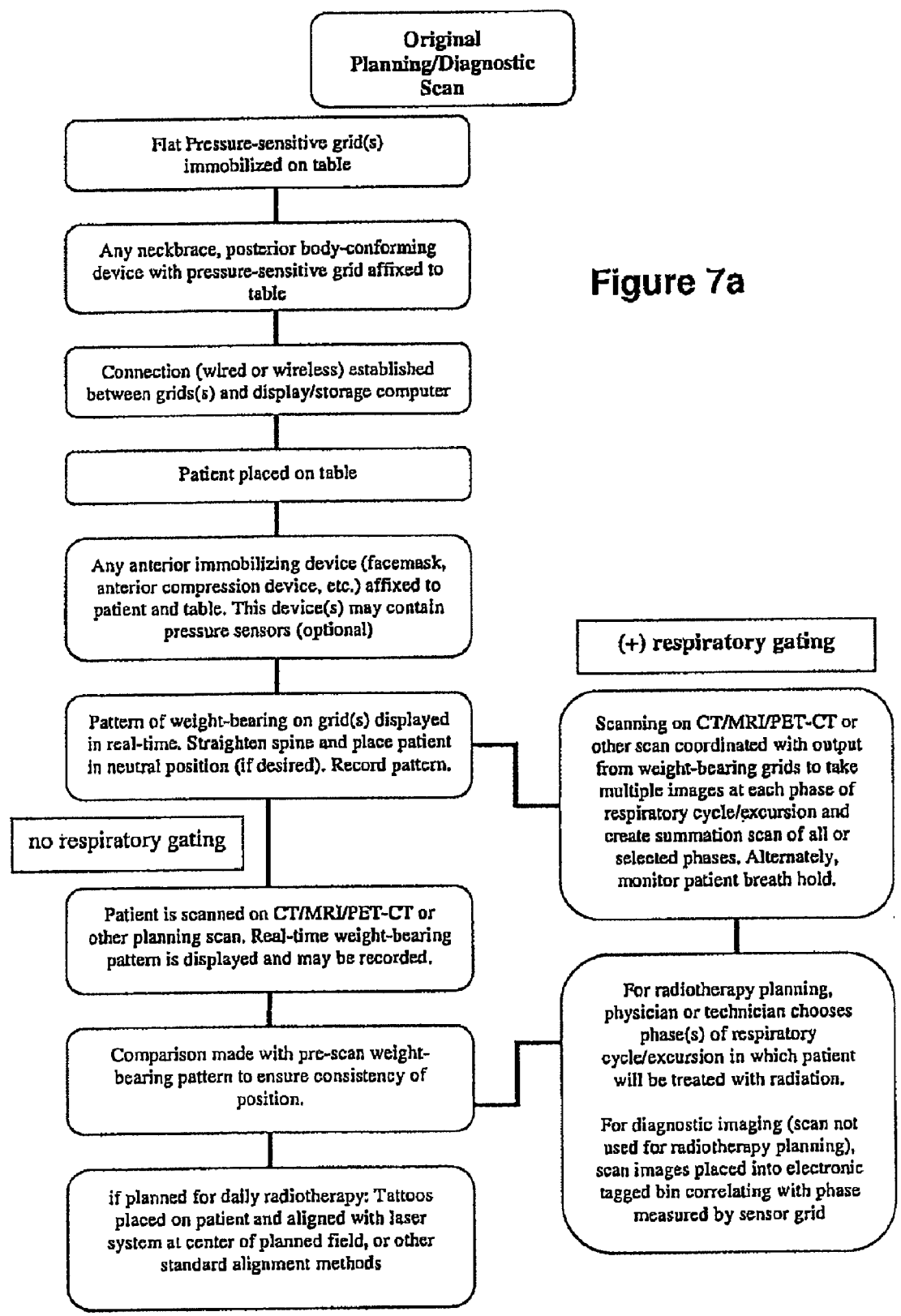
FIGS. 7a and 7b represent flowcharts demonstrating a method utilizing pressure-measuring sensors to ensure that a patient is aligned with a prior planning or diagnostic radiology/nuclear medicine scan.
Figure 7B:
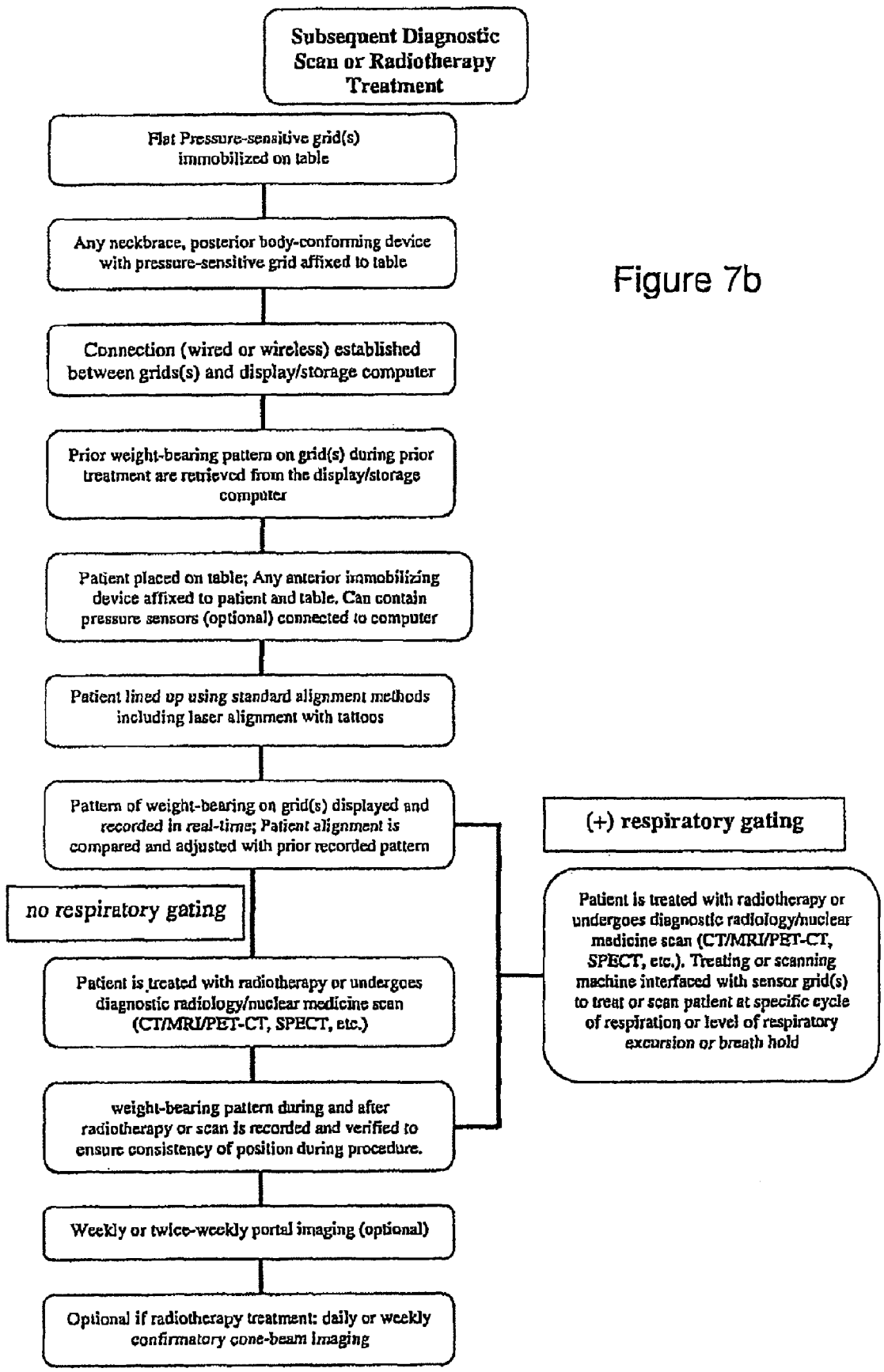

FIG. 7 represents a flowchart demonstrating a method utilizing pressure-measuring sensors to ensure that a patient is aligned with a prior planning or diagnostic radiology/nuclear medicine scan. On day 1, the pattern with which the patient exerts weight on the table and/or body mold(s) is stored (FIG. 7a). Any molds of the posterior aspect of the body may be made—typically using a commercially available device—and may incorporate sensor grid(s) or strip(s) as described in other figures. Methods of alignment currently used in standard practice can be utilized. In the patient being planned for radiotherapy, this will typically involve the placement of 3 pinpoint tattoos at the level representing the center of the treatment field, which will be used in the future to align with a laser-based system such as a LAP-laser (LAP GmbH, Lueneburg, Germany). At the discretion of the user, results from the pressure sensor grid(s) may also be used to shift the patient into a neutral position which may be more easily reproduced on subsequent days, since most patients tend to tense up on the initial day and then relax into a more neutral position in subsequent sessions. In the patient being planned or scanned with respiratory gating or excursion, the changes in weight-bearing pattern with chest and abdominal excursion are noted as in FIG. 6, with the method as described in that figure. On day 2 and beyond (FIG. 7b) for radiotherapy or subsequent radiographic/nuclear medicine imaging, the sensor grids would be locked into place and the molds made on day 1 would be placed based on the patient's original setup. The patient would be aligned using the aforementioned, commercially available methods. The stored original weight-bearing pattern is compared to the real-time pattern seen on day 2 and beyond. If the weight-bearing/pressure patterns do not sufficiently match, then the technician will reposition the patient. Comparison will then be made instantaneously with the new pattern of weight-bearing, and the technician will reposition the patient until there is a match with the original pattern. The match will be based on both areas receiving small-moderate amounts of pressure and weight-bearing (soft tissue), as well as areas of higher levels of pressure that represent bony spine protrusions, protuberances from the skull, protrusions from the scapula and pelvic bones, rib protrusions, as well as bony protrusions of the extremities. For radiotherapy purposes, the patient could periodically receive confirmatory 2-dimensional radiographs (portal imaging) as is standard commercial practice at this time.

Cone-beam CT scan or in-room CT scanners could also be utilized on a weekly or more frequent basis in order to confirm position on a 3D basis, as well as to assess for any anatomical changes with radiotherapy treatment. Secondary confirmatory imaging would not be necessary if the procedure on day 2 or beyond if not radiotherapy, but instead consists of a diagnostic or nuclear medicine scan. If the patient is to undergo respiratory gating, commercially-available methods or the method described in FIG. 6 is utilized.

Figure 8A:
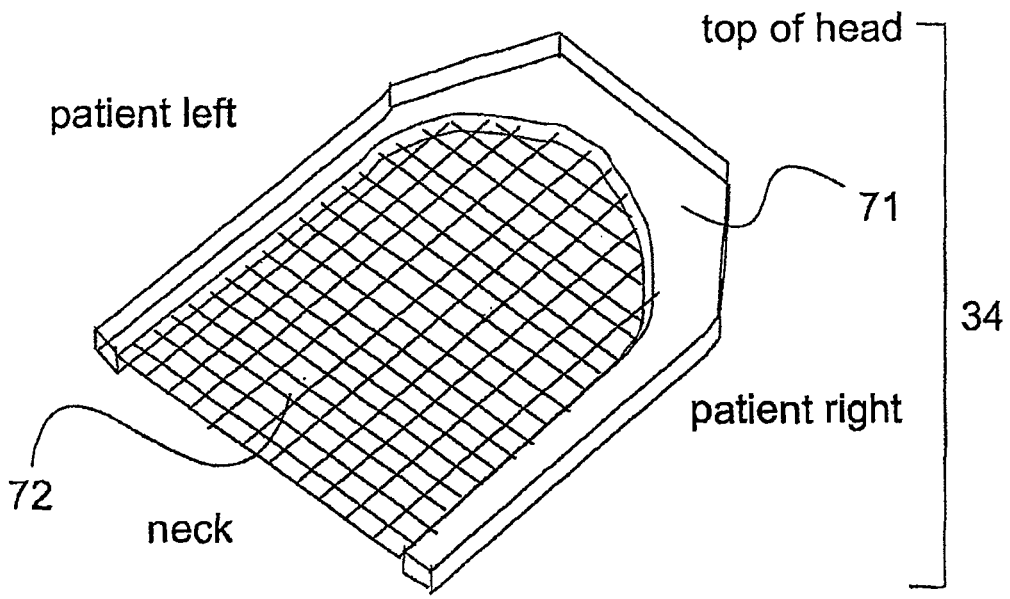
FIG. 8a is a representative view of a commercially available thermoplastic mask or other mask which rigidly conforms to the head, facial and/or neck contours of the patient.
Figure 8B:
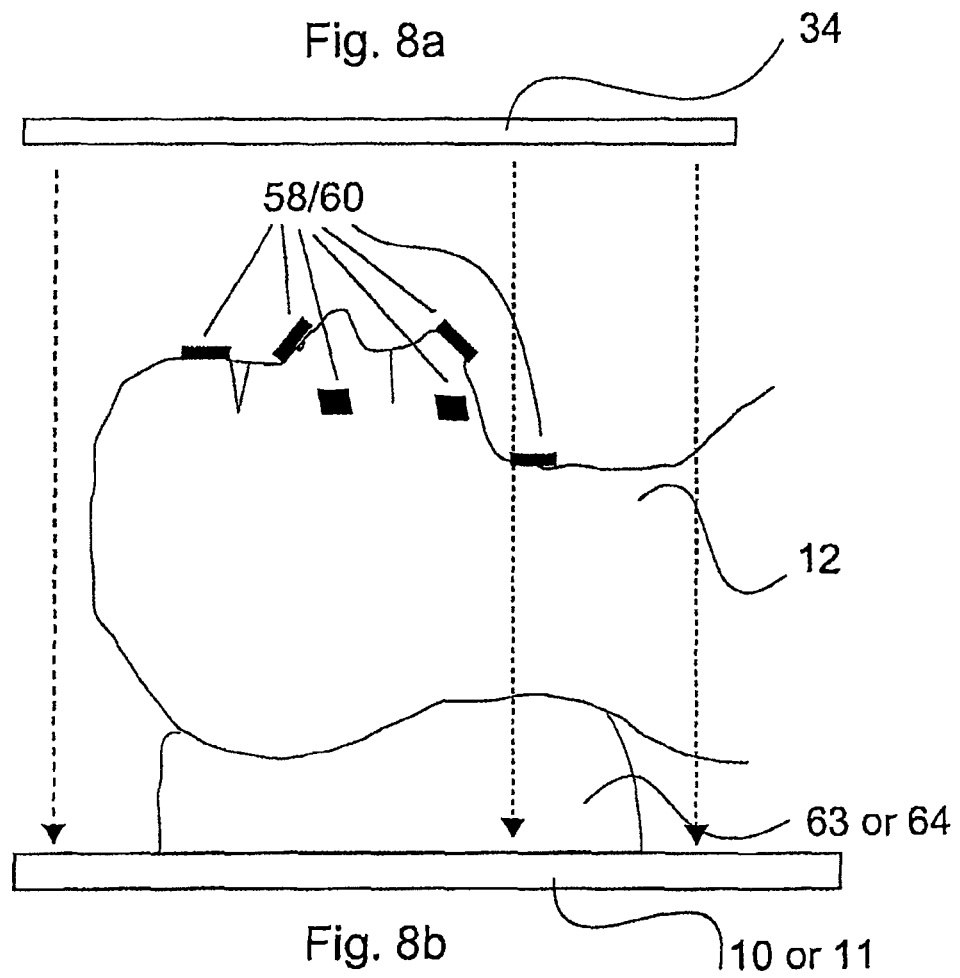
FIGS. 8b, 8c and 8d demonstrate how the invention is to be incorporated into a mask or mold of any body contour, in this case the head and neck.
Figure 8C:
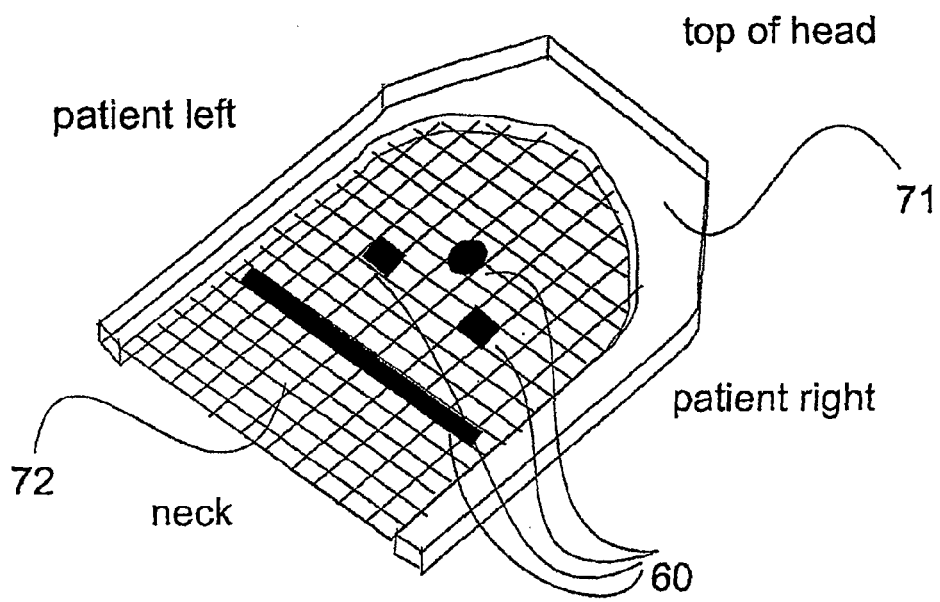
Figure 8D:
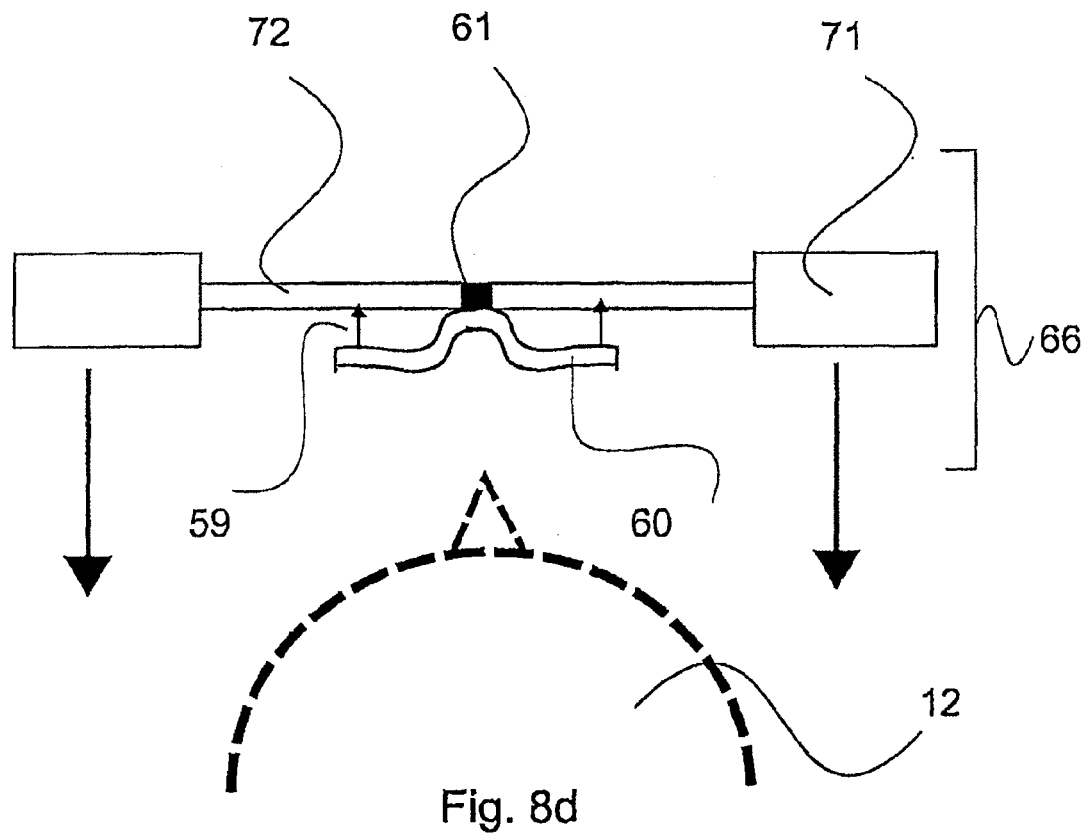

FIG. 8 is a representative view of a commercially available thermoplastic mask or other mask which rigidly conforms to the head, facial and/or neck contours of the patient (FIG. 8a—prior art). FIGS. 8b-d demonstrate how the invention is to be incorporated into a mask or mold of any body contour, in this case the head and neck.

FIG. 8 is a representative view to reduce variability in patient positioning, assess for laryngeal motion/swallowing, and to compensate for respiratory motion is described here.

FIG. 8 shows a commercially available mask which is conformed to the contour of a patient head, face, and/or neck. In the commercially available thermoplastic mask depicted here (FIG. 8a and FIG. 8b), pressure-measuring sensors 58/60 are first placed on the patient's skin at the areas of interest, which may include but would not be limited to the bilateral superior orbital ridges (overlying eyebrows), malar prominences (cheeks), upper nasal bridge, bottom of the mandible, sides of the mandible, the thyroid cartilage and area anterior to the voice box, elements of the clavicle and/or shoulder. The mask 34 may encompass the entire head, face, neck and shoulders, or it may encompass only 1 or several of the body regions noted. The sensors at each spot can be a sensor 58 of any shape containing one sensing element, or can be a small square, rectangular, a linear strip, circular, or an irregularly shaped array 60 containing multiple sensing elements. The mask 34 contains a stretchable material 72, typically but not necessarily a low melting-temperature thermoplastic, which is then conformed to the contours of the patient's head and/or neck and hardened as is standard commercial practice for head and neck immobilization. The sensors 58/60 are then attached to the stretched material 72 via a temperature or non-temperature sensitive glue/adhesive 59 or via a mechanical connector 59 (not shown) that faces the mask. Surrounding the stretchable material is a C-shaped rigid support 71 which contains a connector (not shown) that connects to the table 10 or flat surface 11 that itself connects to the table. An alternative to the above method of sensor incorporation into the mask/mold is to incorporate individual sensor(s), strip(s) and/or grid(s) of the pressure-sensing elements at the time of manufacture (FIG. 8c; head-on view shown in FIG. 8d). If a large grid or a long strip of the pressure-measuring sensors is utilized, the physical attachment of the pressure-measuring array to the flexible mask/mold material 72 will commonly be only in a small portion of the entire pressure-measuring sensor array 60 at the center 61 or to one side 61, since the sensors are not able to expand in-sync with the mask material when it is stretched. Once the mask is stretched to conform to the patient's head, face, neck or other body contour, the rest of the flexible sensor array 58/60 will have an adhesive backing or other attachment device 59 which will be used to affix the rest of the pressure-sensing array to the stretched mask or customized mold 72. The mold shown is stretched to conform to the head, face, neck and/or other body contours of the patient, onto which the pressure sensors can be attached either via an adhesive backing or mechanical connector 59 facing the mask which is placed first on the patient as outlined in FIG. 8b or via incorporation into the stretchable mask at time of manufacture 66 as outlined in FIG. 8c and FIG. 8d. The pressure-measuring sensor(s) 58 or 60 then send a wired or wireless signal 28 to the computer (not shown in this figure) 20 or 32, which stores or displays the pressure values which are measured in real-time. If a patient is shifted to one side compared with their initial planning scan or initial diagnostic radiology/nuclear medicine scan, then sensor(s) on the side to which the patient is shifted will register an increase in pressure while the contralateral side will register a decrease in pressure. This will be monitored in real-time, used to change patient position based on the pressure readings, and is described further in FIG. 13. The same method for attaching and utilizing the sensors may be used when using the stretchable mask/mold on other body sites, as shown in FIG. 11. The pressure sensors 58/60 are reusable and may be detached and used on another patient. Usually, the sensors will be detached from a patient's mask/mold and reused once the original patient's treatment or scanning course lasting several hours to several months or more is completed. Less commonly, the sensors could be detached and used on the mask/mold for a different patient, and then reattached to the mask/mold for the original patient; this is to be used primarily in cases where the sensor array/grid is small and attached to the mask/mold via a rigid, easily detachable mechanical connection.

Figure 9A:
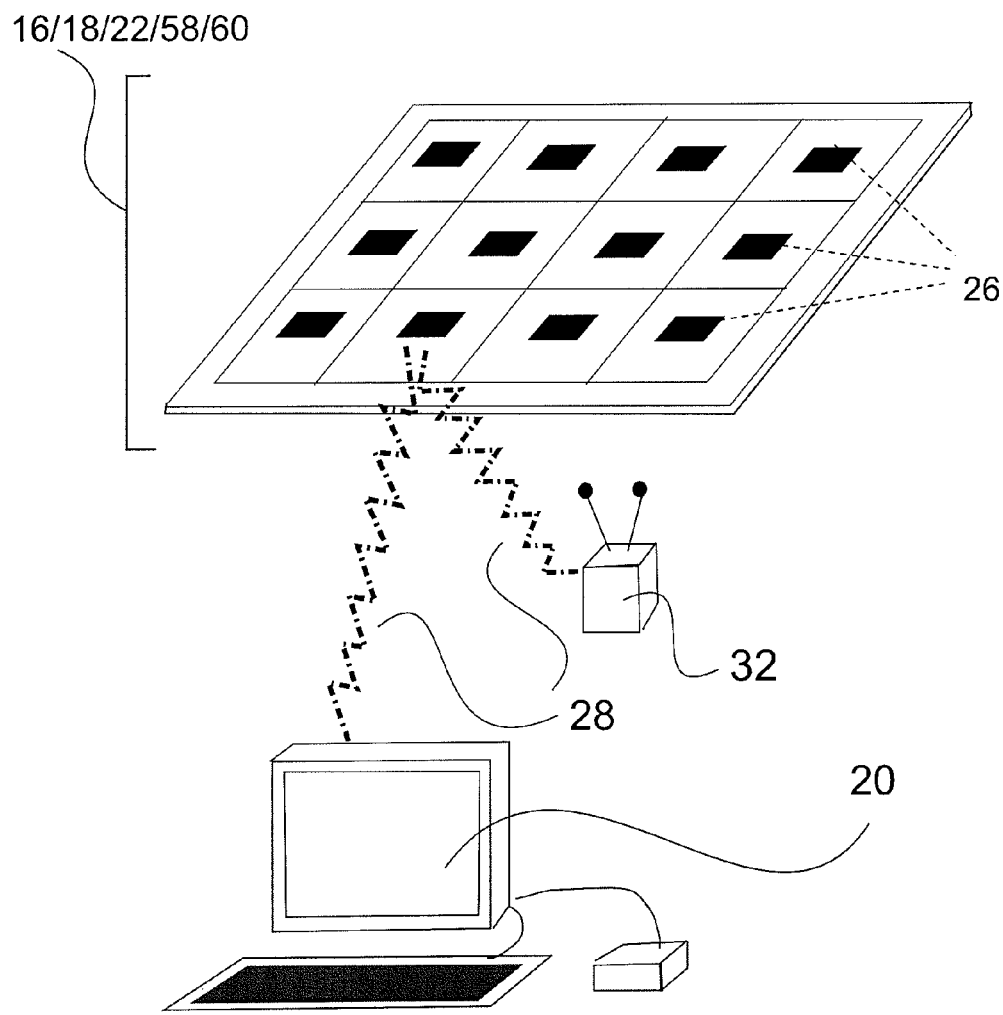
FIGS. 9a and 9b are close-up schematic view of the pressure sensors.
Figure 9B:
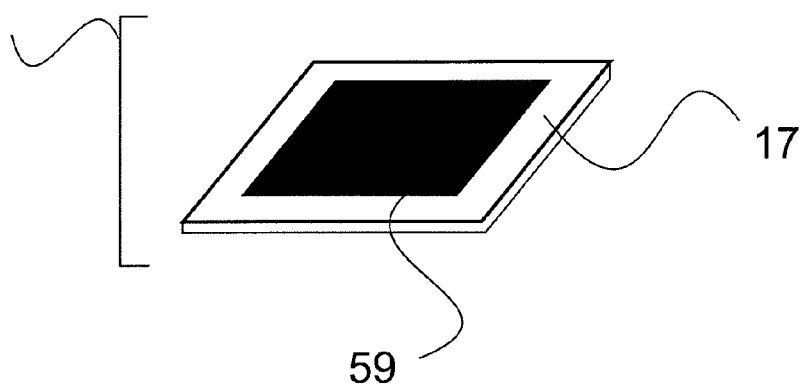

FIG. 9 is a close-up schematic view of the pressure sensors. FIG. 9a is a view of a schematic view of the pressure sensors 16/18/22/58/60, with their electronic output 28 to a computer 20 or other 32 display/storage device. Each of the sensors 16/18/58/60 contain one or more (up to tens of thousands or more) pressure sensing elements 26 spaced submillimeter up to tens of centimeters apart. FIG. 9b demonstrates the back of the flexible or rigid housing that holds the sensor(s) or sensor array(s) 16/18/22/58/60 which contains a backing 59 which can be a glue, adhesive, or mechanical connection to the table, rigid support or compression device, or to a customized mold or mask.

FIG. 10 is an embodiment of how sensors could be incorporated in specific areas in a mask of a body contour, in this case the head and neck, for positional verification. Also demonstrated is the method in which to perform laryngeal gating or determination of swallowing phase.

Figure 10A:
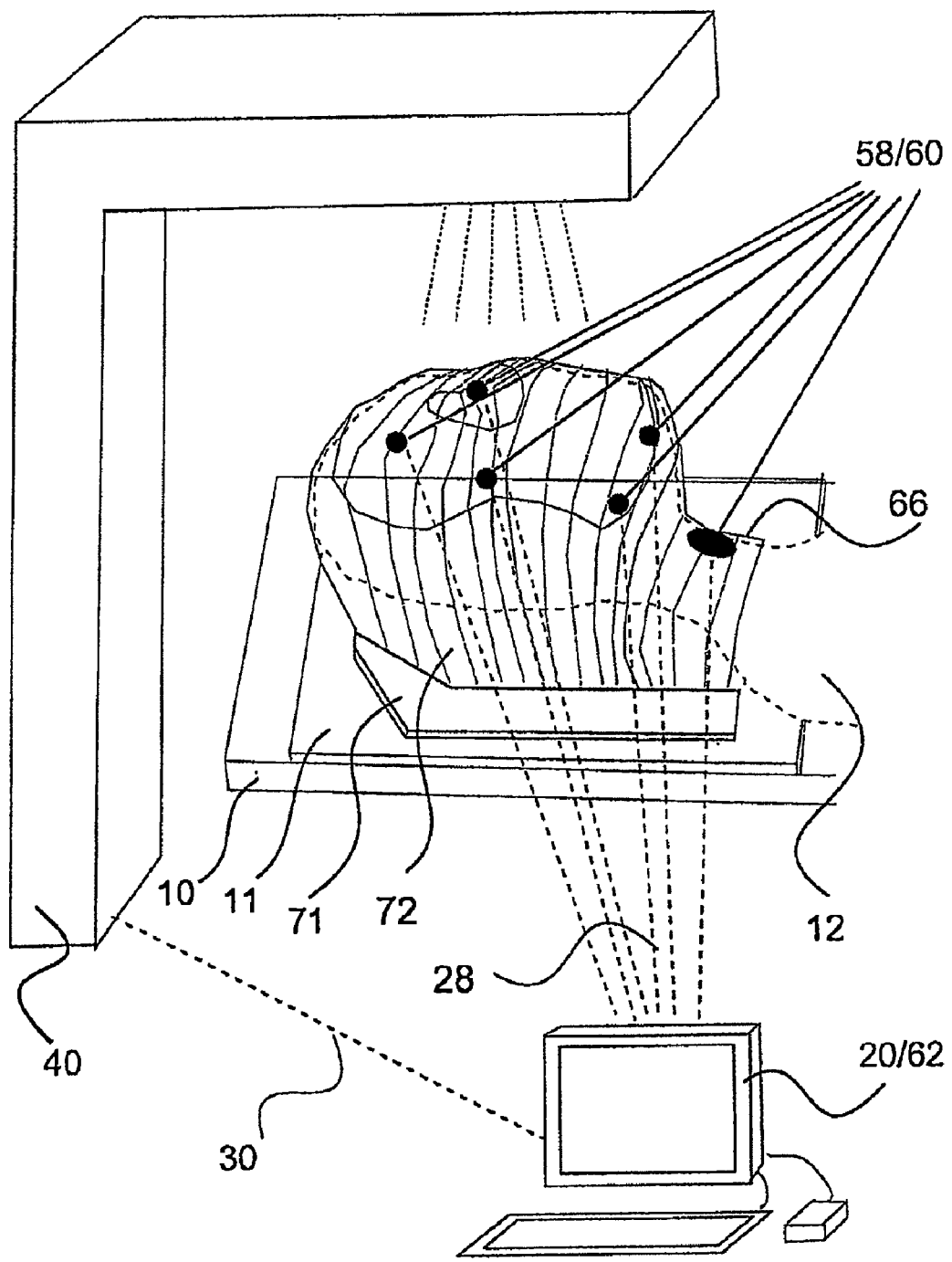
FIG. 10a demonstrates a commercially available thermoplastic mask which conforms to the contours of a patient's body in order to achieve immobilization for radiotherapy planning or treatment or a diagnostic radiology/nuclear medicine scan.
Figure 10B:
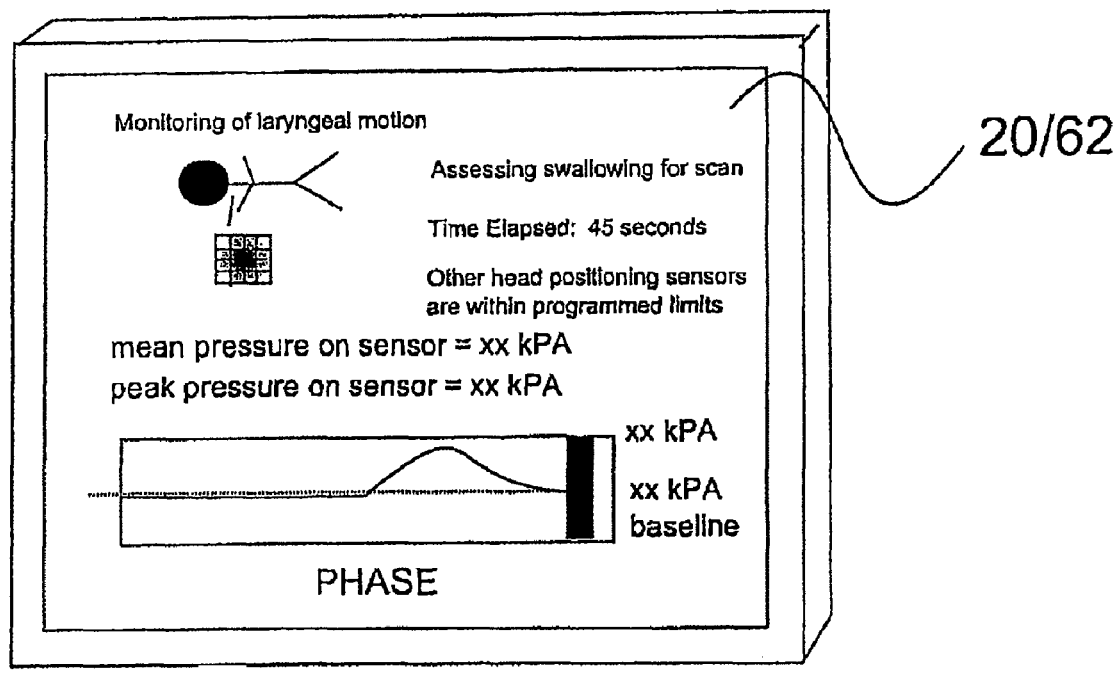
FIG. 10b represents a schematic for monitoring laryngeal motion.

FIG. 10a demonstrates a commercially available thermoplastic mask which conforms to the contours of a patient's body in order to achieve immobilization for radiotherapy planning or treatment or a diagnostic radiology/nuclear medicine scan. This particular mask is of the head, face and upper neck area, but other commercial systems may also cover the area encompassed by this mask as well as a portion or all of the neck and may or may not encompass the shoulders. Other anterior masks or molds will cover the neck only, the chest, abdomen and/or pelvis (FIG. 11), or any other part of the body. This system may also be used with a diagnostic radiology or nuclear medicine scan, including when using these diagnostic scans for purposes of radiotherapy planning. In the figure, the head/face/neck-conforming mask shown is in place incorporating the invention, with the pressure-measuring sensors 58/60 incorporated in areas of the face, head and neck as noted in FIG. 8 (including but not limited to the superior orbital ridge, the malar prominence, the nasal bridge, as well as the inferior aspect and/or sides of the mandible). If a mask is used that also covers the upper and mid-neck, laryngeal motion can be assessed with placement of pressure-measuring sensor(s) at the level of the skin overlying the thyroid and cricoid cartilages and other portions of the larynx. The mask 34/66 (71, 72) is attached to either a rigid board 11 or to the treatment/scan table 10 using standard commercial methods. FIG. 10b is a view of the output 28 from the pressure-measuring sensor(s) in the head and neck mask that are sent to an electronic receiving device 20, 32, 62. This device then displays in real-time the amount of pressure that is exerted on each sensor, which are either arranged individually or placed in strip(s) or grids(s) that are affixed to the mask as noted in FIG. 8. The display can either be graphical, in which the amount of pressure being exerted on a given sensor is displayed as a change in color (commonly, higher pressure would be represented in gradations of red or black, while lower exerted pressure on the sensor would be presented in gradations of blue or white), or the pressure value may be represented in numerical form. In the figure shown, the laryngeal gating sensors can consist of a n×m (often 4×4) grid of sensors, and the pressure measurements are represented in gradations of black and white. As noted previously, laryngeal gating can be accomplished with one sensor or multiple sensors that are arranged linearly or in a grid arrangement as shown in the figure. The format of the screen could vary, but in the case represented in this figure the location of the sensors is represented by the placement of boxes with the pressure sensor reading placed in a geographically representative location in a graphical depiction of the mask. In this case where the mask is covering the head, face and neck, the representation of sensor placement is over the malar prominences, inferior and lateral portions of the mandible, thyroid cartilage and larynx, as well as the lower neck. In the display depicted here, laryngeal motion is also being assessed by taking a reading of the pressure being exerted by the thyroid cartilage and larynx on the overlying pressure-reading sensor(s). The patient has just completed swallowing, which has been detected by the differential pressure that was exerted on the sensors in real-time. If the patient swallows during treatment, the computer 20 in laryngeal monitoring mode 62 sends an output 30 to pause the radiation therapy machine. If the computer is connected to a diagnostic radiology/nuclear medicine scanner, the output 30 may prompt the diagnostic radiology/nuclear medicine scanner to disregard the images taken while the patient swallowed, or put the images associated with each phase of swallowing into a different bin which can later be used for comparison of anatomical differences in the patient with swallowing versus not swallowing. Commonly, the phase of swallow and laryngeal movement will be divided into 2 or more gradations and patterns of pressure that demarcate the extent to which a patient is swallowing. Taking all of these gradations and patterns measured by the pressure sensor(s) is used to constitute a phase or cycle of swallowing.

Figure 11A:
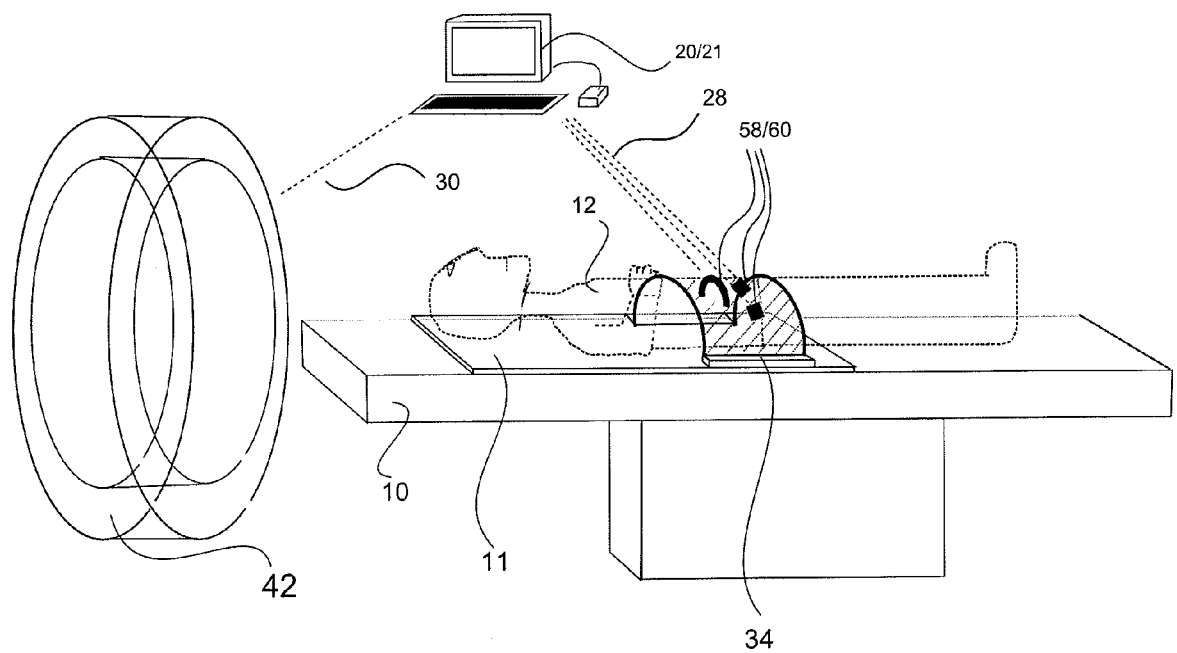
FIG. 11a is a side view which shows a patient immobilized for treatment for thoracic, abdominal and/or pelvic radiotherapy or stereotactic radiosurgery with a body-conforming mold or mask.
Figure 11B:
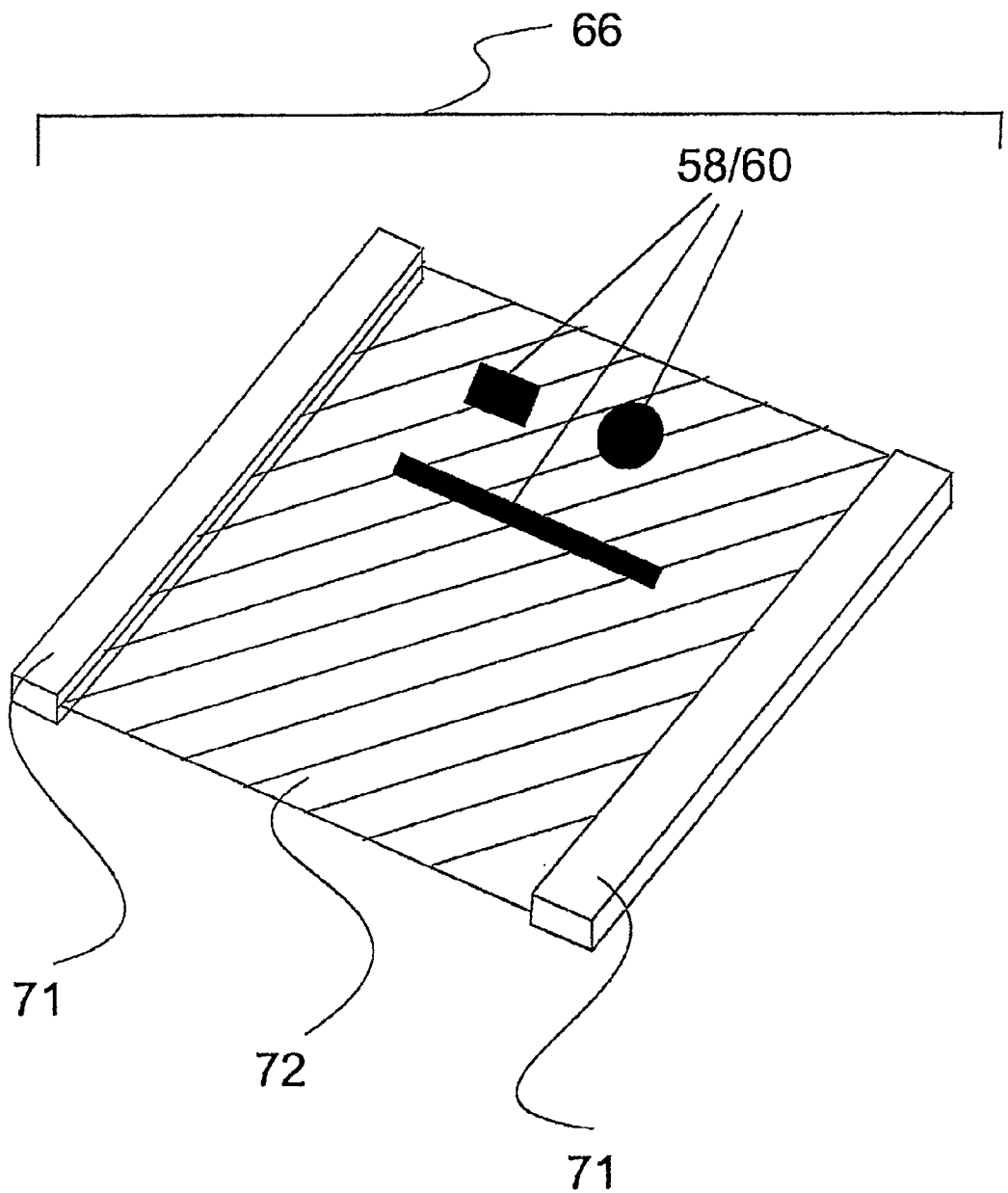
FIG. 11b is a representation of a body conforming mold or mask having sensors attached or embedded thereon prior to attachment to the patient.

FIG. 11a is a side view which shows a patient immobilized for treatment for thoracic, abdominal and/or pelvic radiotherapy or stereotactic radiosurgery with a body-conforming mold or mask. FIG. 11b shows a mold or mask prior to being conformed to the body contour, in this case incorporating the sensors at the time of manufacture. The mold or mask achieves abdominal immobilization and/or compression.

FIG. 11 shows a commercially available device used for radiotherapy, stereotactic radiosurgery or diagnostic imaging of the abdomen or pelvis 34 or 66. Similar systems are used for the thorax, head, neck, or any other body part for immobilization, and is also shown in FIG. 8 for head and neck immobilization. FIG. 11a demonstrates a case of abdominal and/or pelvic immobilization, in which the compression device is utilized to prevent significant abdominal motion and/or the attendant organ and tumor motion with respiration. The incorporation of the sensor(s) with the anterior mask or mold 34/66 is identical to that described in FIG. 8. In brief, sensor(s) or array(s) of sensors are incorporated into the anterior mask or mold either at time of manufacture or on the day of initial planning or diagnostic scan, in order to verify patient position and/or monitor respiration. If the patient moves or is out of position relative to the mask, then sensor(s) on the side to which the patient is incorrectly shifted and/or rotated will register an increase in pressure, with a corresponding decrease in pressure on the contralateral side. With respiration, there is differential pressure exerted on this rigid device with respiration; this could be used as a surrogate of patient respiration (explained further in FIG. 12). Optionally, sensors would be placed on the table or posterior mold and output readings that could be integrated with those from 58/60. With patient inhalation there generally would be increased pressure placed on the device, while with patient exhalation there would generally be decreased pressure placed on the sensor(s) which could be quantified and sent electronically in wired or wireless format 28 to a computer 20 in respiratory monitoring mode 21 or receiving device 32 that are either in the treatment room or outside. Based on the pressure exerted on the sensor and the phase of respiration to which it corresponds, the computer 20/21/32 sends a signal 30 to control a radiotherapy machine 40 or a diagnostic radiology/nuclear medicine scanner 42. The exerted pressure pattern that corresponds with a specific phase of the respiratory cycle (expiration, inspiration, etc.) can then be recalled during subsequent radiotherapy sessions or diagnostic imaging/nuclear medicine sessions. For radiotherapy, this would be used to turn the radiation beams on or off according to the phase(s) of the respiratory cycle or excursion that have been chosen on the initial planning day to treat the patient. This is similar to a commercially-available method for respiratory gating, which uses abdominal motion as a surrogate for respiration. However, in the setting of extracranial stereotactic radiosurgery or stereotactic radiotherapy in which abdominal compression can be utilized, the commercially-utilized surrogate of abdominal motion is difficult to obtain. This method therefore has utility as a surrogate for respiration in that setting as described in FIG. 12a, as well as in the setting of conventional fractionated radiotherapy previously described. For diagnostic radiology and nuclear medicine studies, the sensor 16/18/22/58/60 can be used to associate a set of images with each phase of the respiratory cycle for comparison with the prior diagnostic radiology or nuclear medicine scan. FIG. 11b demonstrates a view of a commercially available body mask or mold 66 prior to being conformed to the patient's body contour. It is an embodiment of the mask which is shown in FIG. 8. Although the mask or mold 34/66 may consist of any deformable shape or material, the most common embodiment shown here would consist of a low-melting temperature thermoplastic material 72, with rigid supports at the sides 71 that would attach to the table on which the patient lying, or a device which is rigidly attached to the table. Immobilization of the mask or mold onto the table or rigid attachment is accomplished using standard commercially-available attachment methods. The example shown in this figure has the sensor(s) incorporated at the time of manufacture, but as described in previous figures the sensors may be placed onto the mask 34 on the day of simulation with an adhesive backing or a mechanical linkage, with similar changes to the thermoplastic material 72 and rigid supports 71.

FIG. 12 is a view of a commercially available abdominal compression device. Incorporated on the head of the device that compresses the patient's abdomen is the invention, used primarily for respiratory gating and determination of respiratory phase.

Figure 12A:
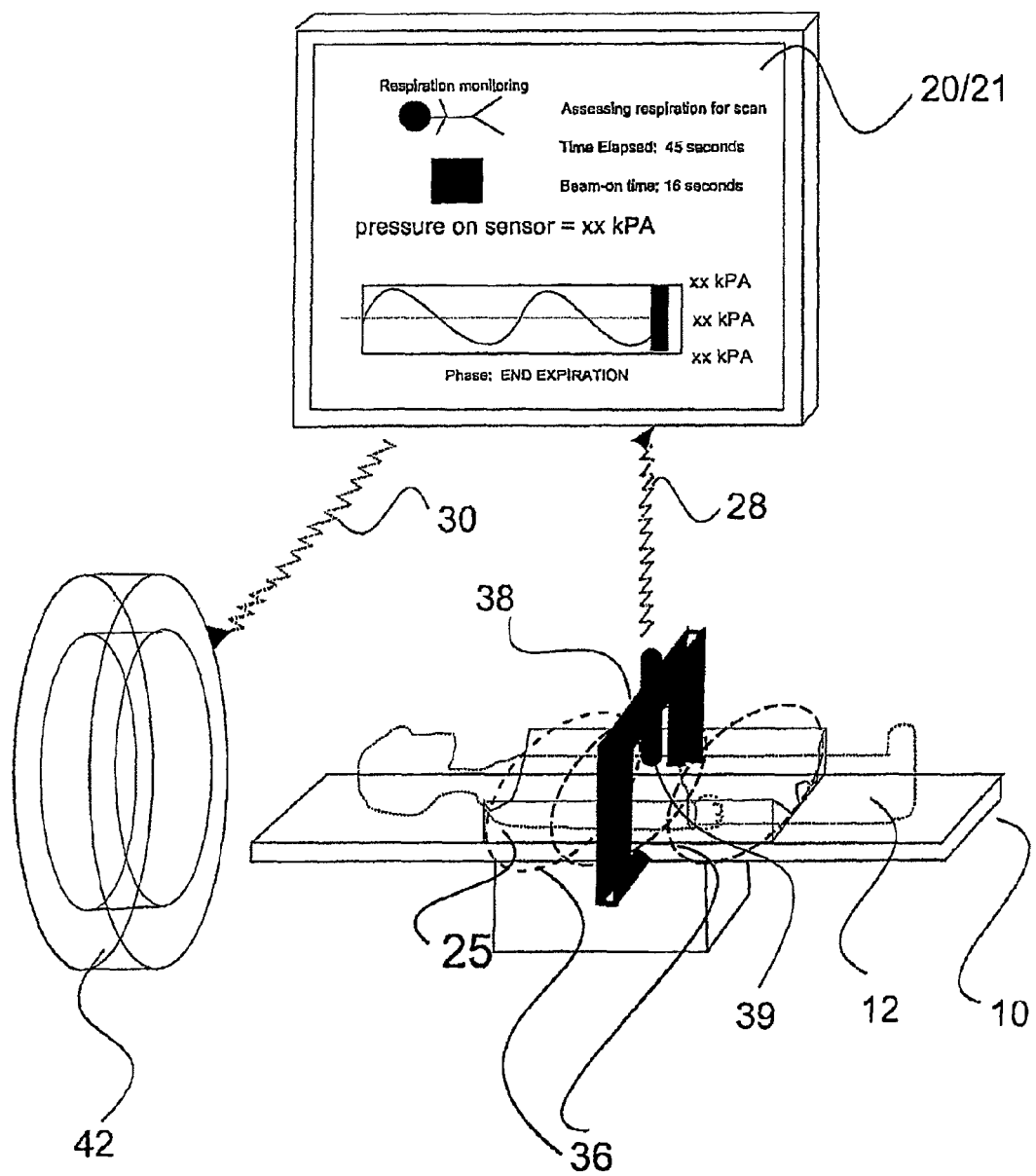
FIG. 12a is a view of a commercially available abdominal compression device. Incorporated on the head of the device that compresses the patient's abdomen is the invention, used primarily for respiratory gating and determination of respiratory phase.
Figure 12B:
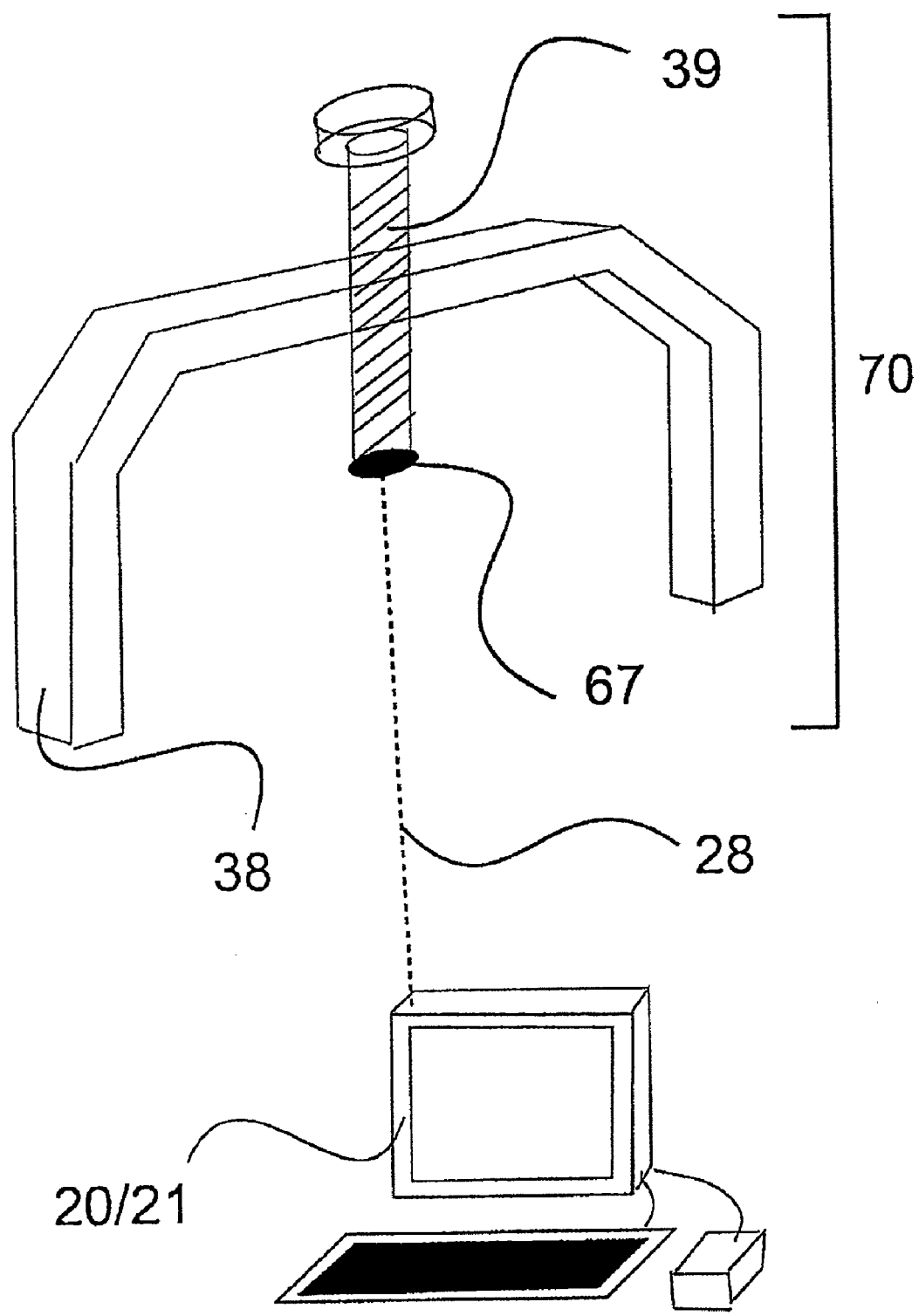
FIG. 12b is a schematic of the chest compression device comprising a sensor and a computer.
Figure 13A:
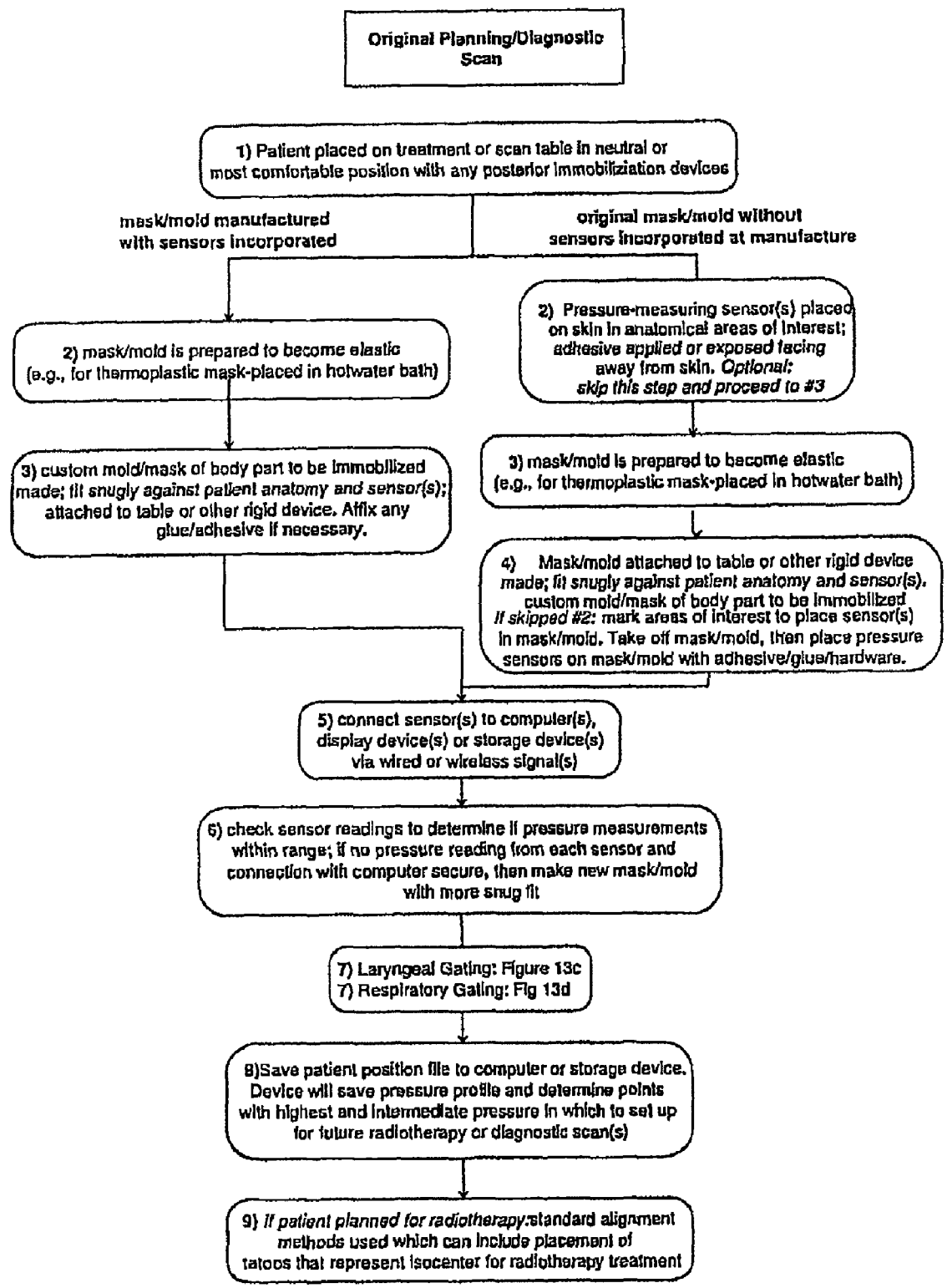
FIGS. 13a, 13b, 13c and 13d are an outline that demonstrates how a patient would be set-up and the invention used on the initial planning or diagnostic scan day (day 1), and in subsequent days for setup reproducibility and for respiratory/laryngeal gating.
Figure 13B:
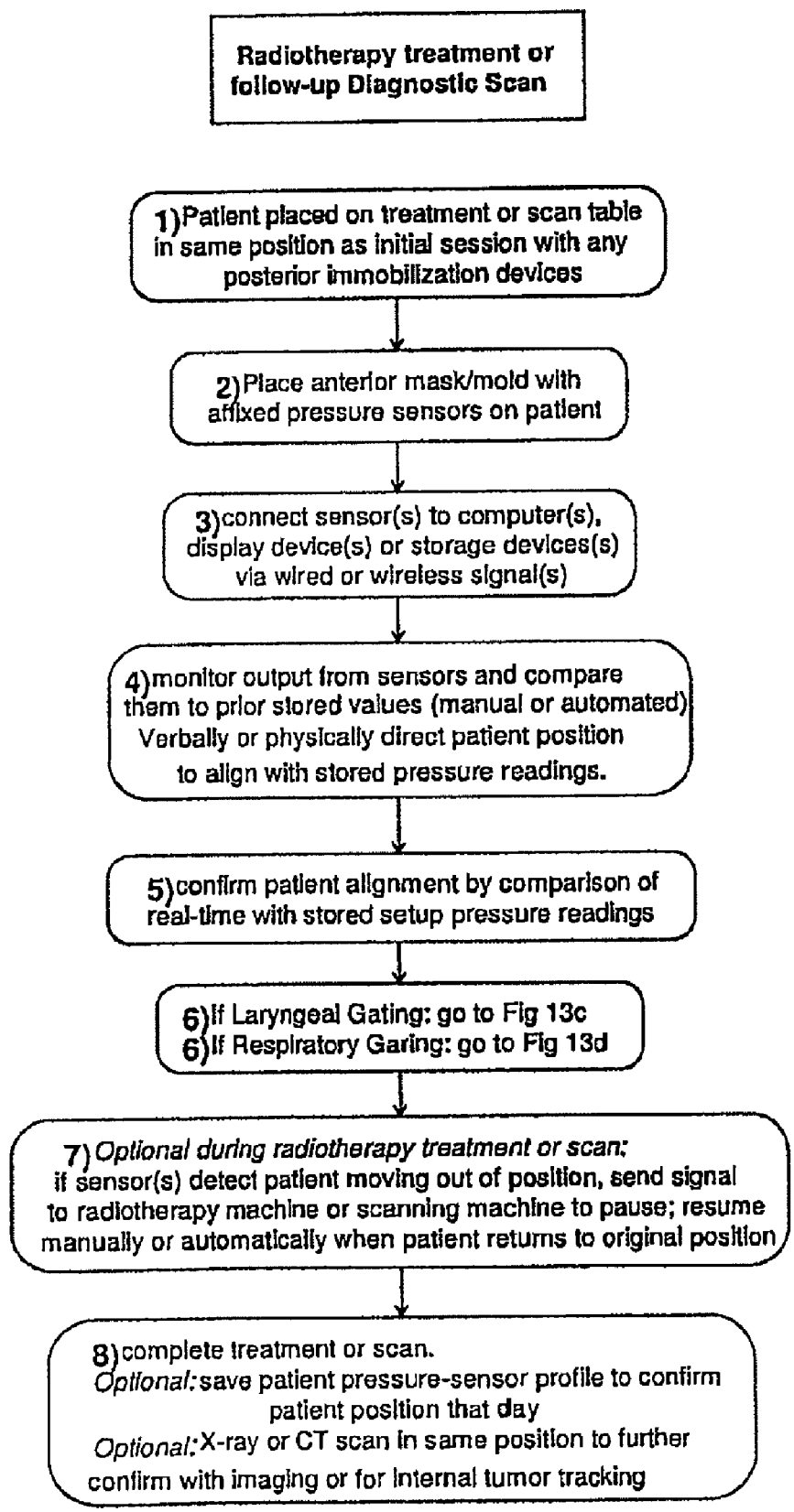
Figure 13C:
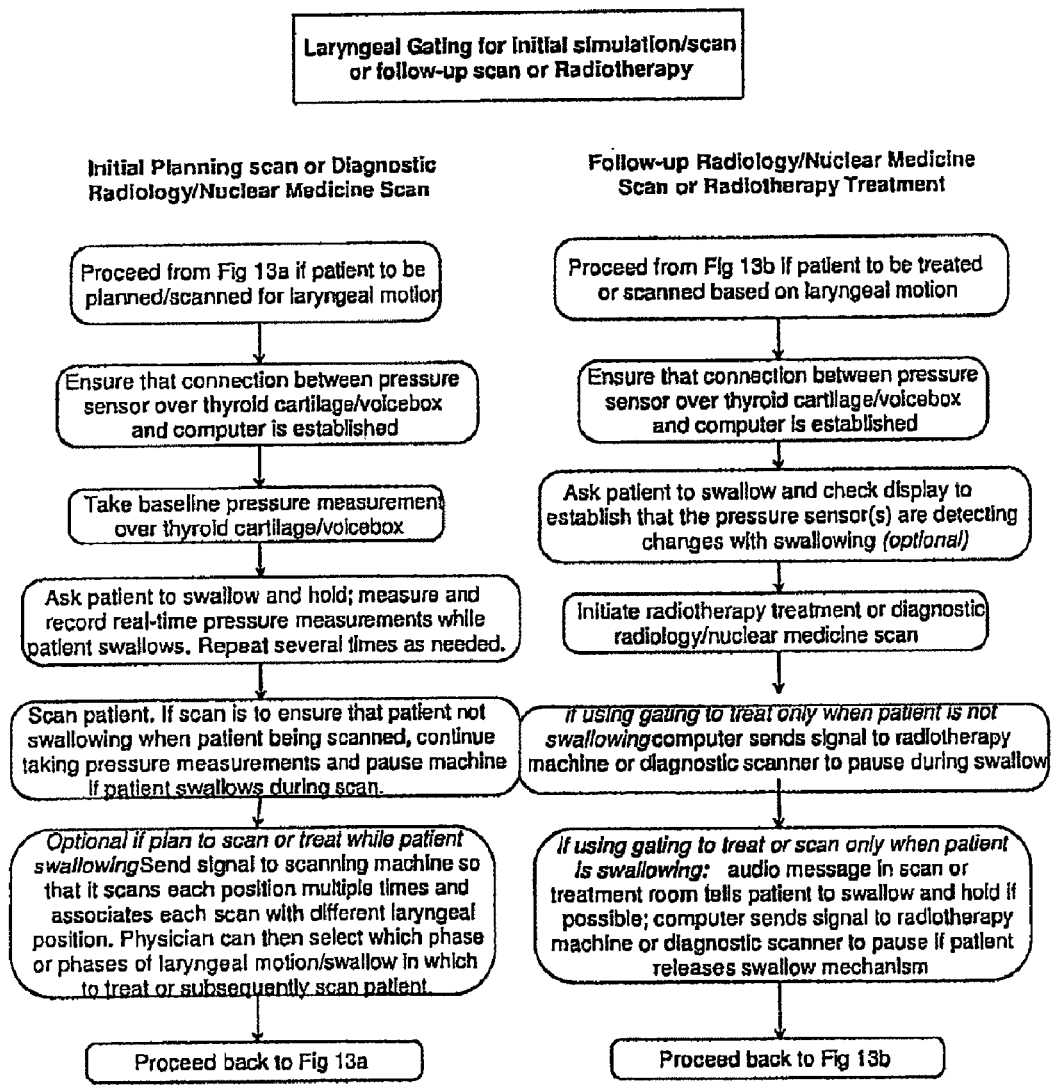
Figure 13D:
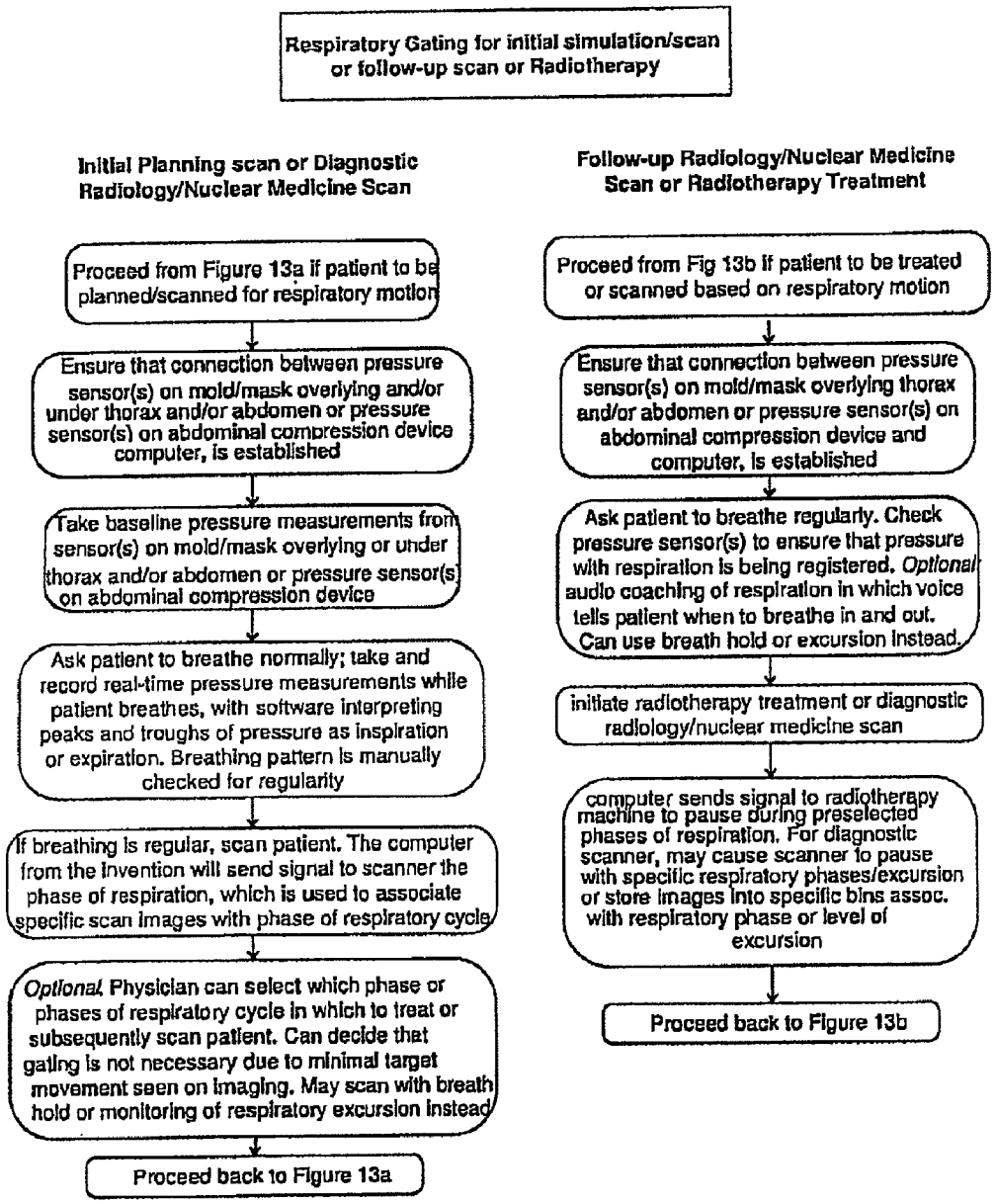

FIG. 12 demonstrates a method of achieving respiratory gating in the setting of abdominal compression. FIG. 12a is a perspective view which demonstrates one version of a commercially available device to achieve further immobilization and abdominal compression. This commercially available device and method utilizes a flexible material 36 with a vacuum seal around the anterior portion of the body to achieve immobilization. In order to achieve further compression of the abdomen to decrease diaphragm motion with breathing, an ancillary frame 38 is attached at the bottom to the patient table, attached to the mold of the patient's posterior body contour, or may be rigidly based on the floor or any other hard surface. As utilized in commercial practice, the frame is attached to a compression device 39 which screws into a rigid base. The invention described here incorporates a pressure-measuring sensor 67 (which is essentially the same as sensors 16/18) into the portion of the compression device that is in direct contact with the abdomen. The compression device could be manufactured with the sensor incorporated at time of manufacture, or could be added on with an adhesive backing or a mechanical connector. Optionally, a posteriorly-based mold 25 with or without pressure sensors (FIG. 3c), pressure sensors on the table (FIG. 4), and/or a rigid anterior immobilization device 34 in place of the flexible immobilization device 36 with or without sensors (FIG. 11) may be added for patient immobilization and/or respiratory monitoring. All sensor(s) output 28 the real-time pressure to a computer 20 or other device with a software-programmable respiratory monitoring mode 21. Based on the differential pressure being exerted, the computer will determine the phase of respiration based on the surrogate marker of pressure transmitted through the compressed abdomen and/or the other pressure sensors. As a patient breathes, there are changes in chest and/or abdominal excursion and expansion during the respiratory cycle which translates into changes in weight-bearing placed on sensors at the level of the thorax, abdomen and/or anterior compression device. With inspiration, more measured pressure will be exerted by the body on the sensor grids placed underneath the thorax as well as the abdomen; this effect will be magnified if there is anterior compression for patient immobilization. With breath expiration and decreased chest excursion and decreased expansion as air exits the lungs, there will be decreased pressure placed on the sensor grids or an up-down migration of the pressure peaks representing rib movement. Standard methods for respiratory gating for radiotherapy or diagnostic scan are utilized. One such standard method would consist of dividing each respiratory cycle into 5-20 or more equally-spaced patterns of gradations of pressure on the sensor(s), with a typical segment number of 10 as known to those of skill in the art. Modifications of this standard method as described in FIG. 5 can be used, including respiratory excursion or breath hold. Any subsequent scans (pre-therapy, post-radiation therapy) can be performed with respiratory monitoring or breath hold, in which images from these scans (CT, MRI, PET, PET-CT, etc.) would be associated with sets of images that are associated with the respiratory-monitored bins. The weight-bearing pattern that corresponds with a specific phase of the respiratory cycle (expiration, inspiration, etc.) or level of chest or diaphragmatic excursion can then be recalled during subsequent radiotherapy sessions or diagnostic imaging. Based on the signal 28 received from the sensor grid, this can be used to interface with the diagnostic scanning machine 42 or radiotherapy machine 40 (not shown) with signal 30. For radiotherapy, this would be used to turn the radiation beams on or off according to the phase(s) of the respiratory cycle or level of respiratory excursion that have been chosen on the initial planning day to treat the patient. In the setting of extracranial stereotactic radiosurgery or stereotactic radiotherapy in which abdominal compression is utilized, the commercially-utilized surrogate of visible abdominal motion is difficult to obtain. This method therefore permits respiratory gating even when there is abdominal compression for radiosurgery or fractionated radiotherapy that would otherwise be difficult or impossible to obtain. For diagnostic radiology and nuclear medicine studies, the sensor grid 67 (comprising sensor array 16/18/22) can be used to associate a set of images with each phase of the respiratory cycle for comparison with the phase of the respiratory cycle from the prior diagnostic radiology or nuclear medicine scan. The pressure-measuring sensor(s) in this context is also used to establish that consistent pressure on the abdomen is being established on a day-to-day basis. FIG. 12b is a close-up view of an example of a commercially available device described in FIG. 12a, demonstrating the invention on the bottom of the compression device. The compression device 70 itself is commercially available. The sensor(s) output in real-time the pressure values to one or more computers 20/21 which displays, stores, and/or interprets the readings.

FIG. 13 is an outline that demonstrates how a patient would be set-up and the invention used on the initial planning or diagnostic scan day (day 1), and on subsequent days for setup reproducibility and for respiratory/laryngeal gating. This is an additional refinement to the procedures described in FIG. 7, including additional procedures for incorporation of the sensors into anteriorly-based pressure sensors.

FIG. 13 is an outline of a typical method in which the pressure-measuring sensor(s) can be applied in accurately positioning a patient for radiotherapy, diagnostic radiology and/or nuclear medicine scan. On day 1 (FIG. 13a), the patient is placed in the same position and with the same devices as they will be positioned with on subsequent days for radiotherapy treatment or scan. This would include any posterior body molds (including but not limited to the commercially available Vac-Lok or alpha cradle systems). The tabletop or posterior body molds could incorporate pressure sensors in different areas of the table or posterior mold as described in the previous figures. For this invention, as described in previous figures, the patient would either then have pressure measuring sensor(s) placed on the skin in strategic areas prior to fitment of the anterior mask/mold or the mask/mold would incorporate them at the time of manufacture. This can be accomplished by having the mask manufactured with the sensor(s) incorporated as described in FIG. 8.

An alternative method would consist of the mask/mold first being conformed to the body contour in the region of interest, the areas of interest being marked on the mask/mold after it hardens, and then the sensor(s) being placed in these regions and fitment repeated by placing the mask/mold with the attached sensors back on the patient. In all the possible embodiments of the method, the flexible and deformable casing for the sensor(s) can incorporate an adhesive backing or mechanical connector for attachment to a commercially available mask or mold; as noted above, this can be attached to the mask either before (placing the sensor(s) directly on the skin before mask is contoured to the body area) or after the mask/mold hardens. A fastener that loops around holes in the material of the anterior mask or mold may additionally be used to prevent movement of the sensor(s) relative to the mask on subsequent days.

The sensor(s) are connected to a computer or storage device via a wired or wireless electronic connection. The pressure measurements obtained from the sensor(s) are checked to ensure that the electronic connection is valid and to ensure that there is enough pressure on the sensor(s) to validate tightness of fit of the mask or mold. If a patient is undergoing abdominal immobilization using a vacuum-based abdominal and/or pelvic device with or without fixed rigid hardware that is used to press on the abdomen to achieve abdominal compression, the vacuum-based chest, abdominal and/or pelvic immobilization device can first be assembled around the patient. The pressure sensor(s) are then attached to the rigid component (which is usually a carbon fiber or plastic screw) of the abdominal compression device as noted in a previous figure. The attachment of the sensor(s) to the head of the component which will contact the patient can be performed at the time of manufacture as an integrated part of the hardware, or the sensor(s) can have an adhesive backing or a mechanical locking device which is used to attach the sensor(s) to the component. The sensor(s) on the head of the rigid component is attached to the computer or storage device. The patient is then asked to breathe in or breathe out to the greatest possible extent then hold their breath, with the pressure sensor measurements being recorded as a reference so that the abdominal compression mechanism can be positioned in the same manner during subsequent radiotherapy or diagnostic radiology/nuclear medicine sessions. Use of abdominal compression does not preclude the use of the other methods of patient immobilization and sensor integration previously noted.

The pressure reading from the sensor can be used to calibrate the amount of compression that the rigid component is placing on the abdomen, and the compression is adjusted accordingly. The pattern with which the patient's body exerts pressure on the anterior body mask(s) or mold(s) is stored in the computer or a memory storage device. Any molds of the posterior aspect of the body may be made—typically using a commercially available device—and may incorporate sensor grid(s) or strip(s) as described in previous figures. Methods of alignment which are currently utilized in standard practice can be utilized. In the patient being planned for radiotherapy, this will typically involve the placement of 3 pinpoint tattoos at the level representing the center of the treatment field. At the discretion of the user, results taken on the first scan from the pressure sensor(s) may be used to shift the patient into a neutral position which may be more easily reproduced on subsequent days, since most patients tend to tense up on the initial day and then relax into a more neutral position in subsequent sessions.

This may or may not require conforming a new mask or mold onto the patient. In the patient being planned or scanned with laryngeal gating, changes in position of the thyroid cartilage, cricoid and other components of the larynx are noted when a patient is asked to swallow. The procedure is noted in FIGS. 3b and 8, and the method is noted pictorially in FIG. 13c. In short, the patient has had pressure measuring sensor(s) placed on any portion of the skin overlying the thyroid cartilage, cricoid cartilage or any other portion of the larynx, and has had the commercially available mask or mold that overlies any or all portions of the head, face, neck and/or shoulders placed rigidly over the sensor(s). The baseline pressure measurements from the sensor(s) are outputted to the computer and stored. The patient is then asked to swallow, and the computer records the measurements in real-time. The patient may also be asked to swallow and hold the swallowing motion as long as possible. The pressure values are then recorded and/or displayed and the pattern of change in the pressure in each sensor with swallowing is noted. The patient then undergoes the planning scan or initial diagnostic radiology or nuclear medicine scan. The computer in the invention can output a signal to the radiology or nuclear medicine scanner that indicates the phase or extent of patient swallowing.

The patient may be asked to swallow or be asked to avoid swallowing as much as possible, depending on the application. If and when the patient swallows, depending on the application, the scanner may either discard the images related to the swallowing movement or may place images that represent every phase of the swallowing cycle into bins that are associated with the phase of the swallowing motion. This may be reviewed by a physician to determine which phases(s) of the swallowing motion are desirable to treat with radiotherapy on subsequent days, or which phases(s) of the swallowing motion in which to obtain a scan (on the same day or on subsequent days) for diagnostic purposes. One embodiment of the invention and technique is its use only on day 1 to take diagnostic scan images in different phases of swallowing and/or laryngeal movement to assess the patient's swallowing or vocal motion. In this case, the patient would proceed through the method outlined in FIGS. 13a and 13c but not undergo the method outlined in FIG. 13b. In the patient being planned or scanned with respiratory gating, the changes in weight-bearing pattern with excursion are noted as in FIGS. 11 and 12, with the method as described in those figures. The method is also described in FIG. 13d. In short, on the initial planning or day of initial scan, the change in pressure on the sensor(s) placed on the posterior, anterior mask/mold and/or abdominal compression device described in the previous figures, including the method from FIG. 7, is noted. This corresponds with the patient's phase of respiration, in which an increase in pressure on the sensor(s) will generally correspond with breath inspiration. Decrease in pressure measured by the sensor(s) would generally correspond with breath expiration. The patient will be asked to breathe normally and may receive audio or visual coaching on how to breathe predictably. The regularity of the breathing will be noted, and if the real-time change in the pressures with respiration are regular, then the patient will be scanned using a respiratory scanning protocol as is standard commercial practice. The scanner will receive an output from the pressure-measuring sensor(s), and will place scan images into a bin depending on the phase of respiration as measured by the sensor(s). A physician may then choose which phases of respiration (if any) in which to take future scan images (on the same day or on subsequent days), or in which phases of respiration (if any) during which to selectively treat a patient with radiotherapy. On day 2 and beyond (FIG. 7b or 13b) for radiotherapy or during subsequent radiographic/nuclear medicine imaging, the same setup for patient positioning would be used, including any posterior molds or neck-rests. The anterior mask(s) or mold(s) containing the pressure-measuring sensor(s) conformed to the patient's body contour on day 1 would be locked into place or the anterior abdominal compression device placed based on the patient's original setup. The patient may be initially aligned using standard commercial practice, which may or may not include the use of a triangulating set of lasers to align a patient according to marks placed on a mask or pinpoint tattoos or other markings placed on a patient's skin or the mask. The sensor(s) are then connected to the computer, and depending on the area being treated the patient may or may not be asked to hold their breath in inhale or exhale.

The pressure measurements from the sensor(s) are compared to the initial sensor measurements, and if they are in agreement the patient starts radiotherapy treatment or the follow-up diagnostic radiology/nuclear medicine scan. For radiotherapy purposes, if there is a global decrease in pressure measured (especially if the area to receive therapeutic radiation is the head and neck area), this would indicate the possibility of significant weight loss and the need for evaluation for a possible new radiation therapy plan. If the sensor(s) on one side of the patient detect increased pressure while the other side detects decreased pressure, the patient is asked to tilt that component of their body (e.g., head, mandible, neck curvature, chest, abdomen or pelvis). This is done until there is a match with the stored pressure measurements from day 1. The acceptable concordance in the match will vary, but would typically be ±5% of the day 1 reading in all or most of the pressure sensor(s) on the anterior mask(s) or mold(s). If the patient is to undergo laryngeal gating (FIG. 13c), the computer is switched to laryngeal monitoring mode and pressure from the sensor(s) overlying the larynx and thyroid cartilage is displayed on the computer in real-time. This mode does not preclude monitoring of patient position during the treatment or scan. During the radiation therapy treatment, the computer will instruct the treatment machine to pause treatment when the patient reaches a user-defined phase of their laryngeal position which corresponds with swallowing or not swallowing (e.g., when a patient is detected to be swallowing while receiving radiation in the area of the larynx). For a diagnostic radiology or nuclear medicine scan, the computer will output the phase of swallowing to the scanner, and depending on the user-defined mode the scanner could place the images into separate bins representing each phase of the swallowing cycle for future review, or it may pause the scanner when the patient is at a specific phase of the swallowing cycle (e.g., not take scan images if the patient is swallowing). If the patient is undergoing respiratory monitoring on day 2 or beyond (FIG. 13d), the pressure sensor(s) will instruct the radiotherapy treatment machine to pause if the patient is not at the user-selected phase(s) of the respiratory cycle, level of excursion (selected by the physician on day 1), or level of breath hold at the desired excursion point. For the patient undergoing a diagnostic radiology scan on day 2 and beyond, the practice is similar to that for laryngeal gating. The computer will output the phase of respiration or level of excursion to the scanner, and depending on the user-defined mode the scanner could place the images into bins representing each phase of the respiratory cycle, or it may pause the scanner when the patient is at a specific phase of the respiratory cycle or excursion (e.g., pause the acquisition of scan images if the patient is not at a specific phase chosen by a physician on day 1, such as when the patient is at breath inspiration). During radiotherapy treatment or diagnostic radiology/nuclear medicine scan, the computer from the invention may send a signal to the treatment unit or the scanner to pause if significant patient movement is detected within the scan, otherwise known as intrafraction movement. After completion of that day's radiotherapy treatment, all pressure measurements may or may not be stored as a record that the patient was treated in the correct position each day. For the patient undergoing radiotherapy, a further optional confirmation of position currently in commercial practice is to take a cone-beam CT, in-room CT or other imaging scan and compare it on a 3D basis to the original scan image from day 1. Such scans could also be utilized to assess for any anatomical changes such as muscle or fat loss that can occur with weeks of daily radiotherapy treatment. For radiotherapy, standard commercial practices of confirmation of patient position such as 2D portal imaging may also be utilized. Such confirmatory imaging would likely not be utilized if the invention were being used only for diagnostic radiology and/or nuclear medicine purposes. The immobilization devices can then be taken off and the patient can leave the treatment or diagnostic scan table.

Another embodiment omits having the scanner pause if a patient moves out of position or extent of desired respiratory excursion during the diagnostic or planning scan. Instead, the exact times when the patient moves out of position can be recorded in the computer (comparing the time-stamp of the computer 20 with that of the table position and time-stamp from the diagnostic scanner), and a second or more full or partial scan(s) can be performed with the patient in the desired position. The imaging software may then select only those images where the patient was in the desired position or level of chest/abdominal/diaphragmatic excursion based on the time and table position-stamps that identify when the patient had moved out of position during the first scan, discarding those images taken when the patient was out of position, and integrate the 2 or more desired sets of images. Thus, a composite image with the patient in the desired position and/or level(s) of respiratory excursion can be created.

In current radiotherapy applications that require precise administration of radiation, 2D portal imaging or confirmatory CT scans are taken more frequently than once a week, and may be taken with each radiotherapy administration. The method described here, with the attainment of reliable patient positioning, may obviate the need for such frequent imaging. In this manner, the patient will not be exposed to the additional wide-field radiation exposure from these imaging scans, and the overall treatment time would be decreased. With this decrease in overall treatment time, more patients could be treated on the radiotherapy machine, thereby increasing machine and staff productivity.

Certain newer forms of radiotherapy, including protons and heavy ions, are highly sensitive to attenuation as they pass through any material, including the materials used in standard immobilization devices. The sensors described in this invention may be used in that context, attached, affixed or embedded onto the treat table, and used for patient positioning with no or fewer physical immobilization devices. Use of these sensors may or may not also obviate the need for daily radiographs to confirm patient position in those settings.

The purpose of this device is to reduce variability in patient positioning during a diagnostic or planning scan, or during a radiotherapy treatment.

Figure 14:
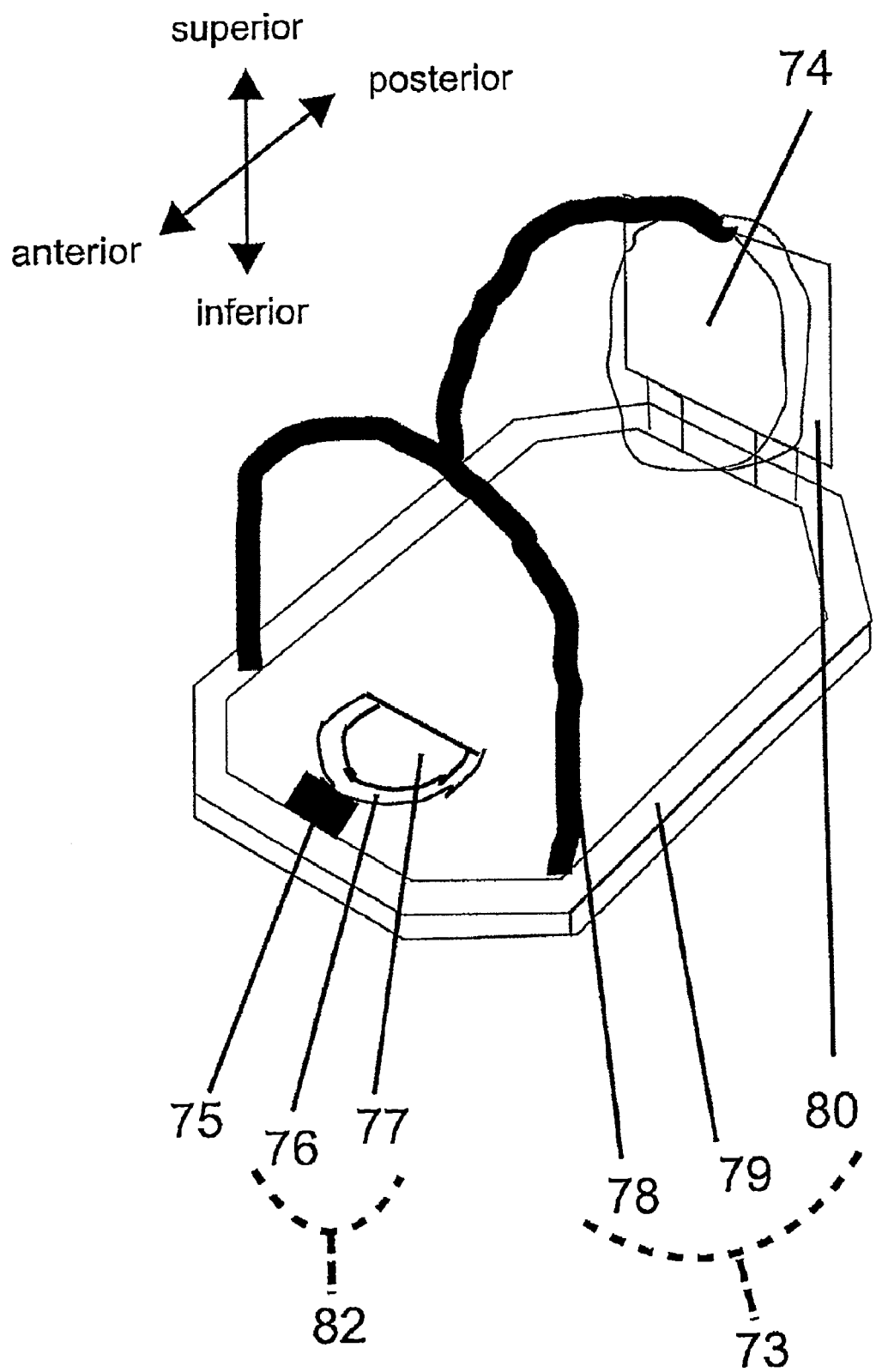
FIG. 14 is one representation of a commercially available, relocatable head ring that is used for radiotherapy immobilization purposes.

FIG. 14 is one representation of a commercially available, relocatable head ring that is used for radiotherapy immobilization purposes. This ring incorporates a dental impression to which it is rigidly affixed. Other similar forms of patient immobilization utilizing a dental impression or other device where the patient bites on an appliance for improved immobilization exist and can be used with the invention described in this document.

Figure 15:
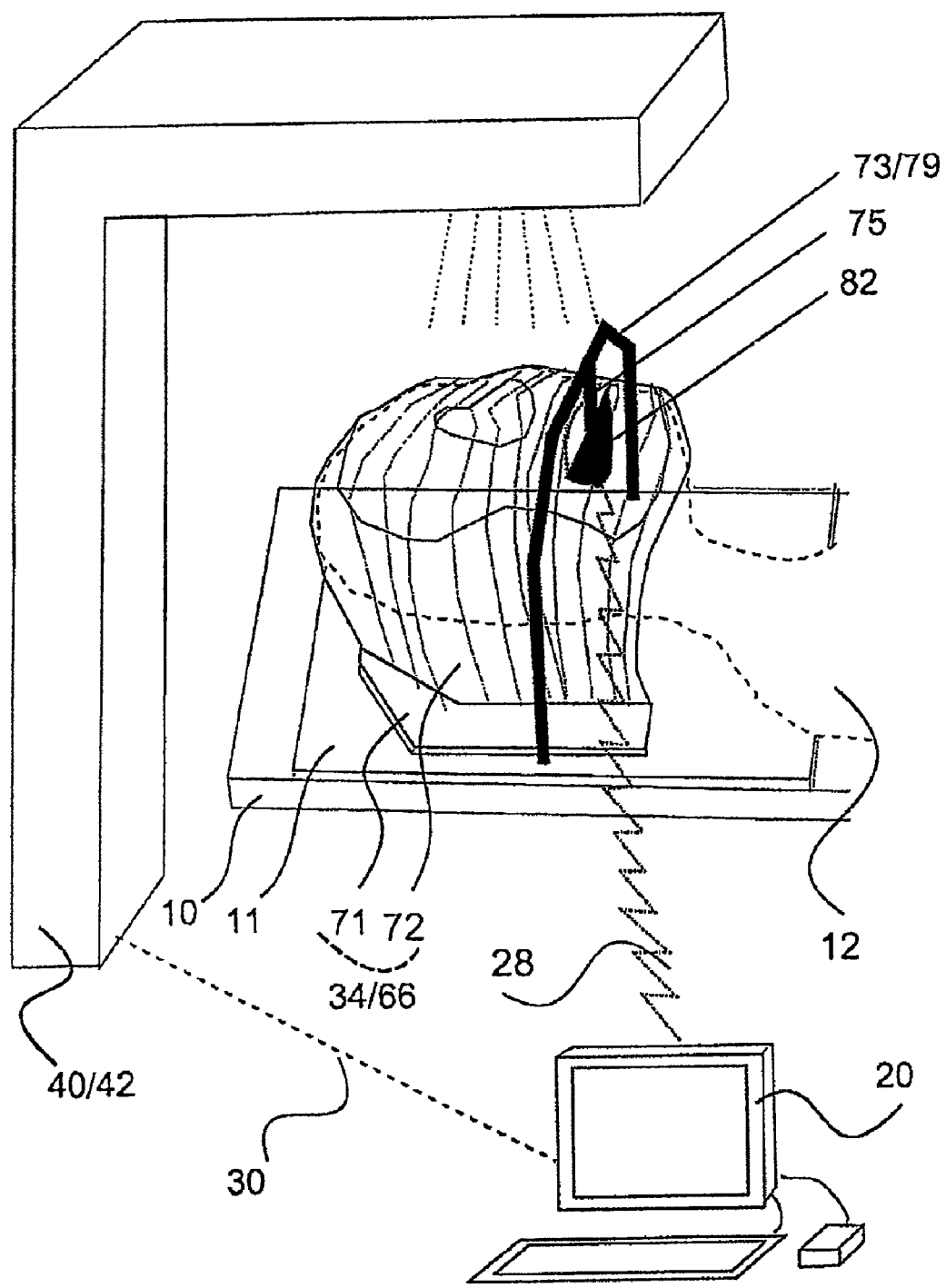
FIG. 15 represents a patient on a diagnostic radiology, nuclear medicine, cerebral angiography, or radiation therapy table with any commercially-available immobilization device or patient tracking device that contains a mouthpiece in place.

FIG. 14 represents a Gill-Thomas-Cosman (GTC) frameless stereotactic immobilization device 73 that is commercially available. The orientation of the device in relation to the patient is shown. The device consists of a mouthpiece 82, made of any flexible or rigid material including silicon putty, paraffin, moldable thermoplastic pellets, or bite wedges. The patient clamps down onto the mouthpiece during the scan or treatment during which he or she is being immobilized. The mouthpiece is connected to a connecting apparatus 75, which may be a rectangular plastic, carbon fiber or other material, which in turn is attached to a rigid frame 79 in the middle of which the patient's head is place. The frame is immobilized onto a diagnostic scan or radiation treatment table (not shown). Additional components of the GTC device are straps 78 that press on the anterior and superior portions of a patient's skull, aiding in the immobilization. The posterior portion of this strap is attached to a head support plate 80, which in turn is attached to the rigid frame. The head support plate 80 may contain a custom mold 74 of the occiput or posterior skull as commonly used in the GTC head frame. Alternatively, a commercially-available neck rest may be used in place of the custom impression 74, as described in the literature, to support both the skull and the posterior neck. Either the custom impression of the skull/occiput or the neck rest may contain strip(s) or grid(s) of pressure sensors as described in FIG. 3c. The mouthpiece 82 as used in the GTC device commonly consists of a dental impression of the hard palate 77 and/or upper teeth and upper alveolar ridges 76. Although not utilized commonly in the GTC device, the mouthpiece 82 may also consist of impressions of both the maxillary and mandibular teeth. Alternate embodiments of the GTC device exist, including devices which utilize a frame 79 that is not closed, and the ends of which attach directly onto the patient treatment table but still retain the mouthpiece. This alternate embodiment is represented in FIG. 15. Additionally, the mouthpiece 82 may be connected not to a frame, but may be connected to an appliance that contains fiducial markers (including infrared beacons, electromagnetic beacons, or metallic or other beacons that are tracked by fluoroscopy or other forms of real-time tracking radiography), as is commercially available.

FIG. 15 represents a patient on a diagnostic radiology, nuclear medicine, cerebral angiography, or radiation therapy table with the GTC immobilization device in place. A thermoplastic immobilization mask is also in place in this example, but all or part of this mask may be omitted or expanded based on the clinician's preference or application.

FIG. 15 represents a patient on a diagnostic radiology, nuclear medicine, cerebral angiography, or radiation therapy table with any commercially-available immobilization device or patient tracking device that contains a mouthpiece in place. In this example, a modification of the GTC frame 73/79 is used, in which two open ends of the frame slot into the table 10 or onto a rigid board 11 attached to the table, onto which the patient is placed. An alternate embodiment has the frame attached to a stand which is immobilized onto the floor of the scanner or the treatment room. Alternatively, a standard and widely available closed GTC frame can be used as depicted in FIG. 14. A commercially available thermoplastic immobilization mask 34/66 material 72 attached to a mask-holder 71 is also in place in this example, and may be used with any embodiment (open, closed frame) or omission of the frame 73/79. The mask may or may not incorporate the pressure-measuring sensors as an embodiment of FIGS. 8 and 10a. Not shown but optionally present behind the patient is a mold of the patients occiput (74 in FIG. 14) or standard neck rest 24, to secure the posterior portion of the head and/or neck. As noted in FIG. 3c, this may also incorporate the pressure sensors. The sensor(s) in the dental appliance 82, as well as any sensor(s) in the thermoplastic mask or mold of the patient's face and head and any mold of the patient's occiput or any neck rest, will communicate with the computer 20/62 via either a wired or wireless connection 28. While in the process of the patient receiving the scan, treatment or radiotherapy, the computer 20 may utilize an algorithm that calculates or otherwise displays to or alerts the radiology or radiotherapy technician that the patient has moved. Optionally, if the computer notes excessive patient movement, it may automatically pause the scan or treatment via a direct connection to the scan or treatment machine 40 via a signal 30. This feature is also described in prior figures, but is expanded to include the output from the sensors in the dental impression or appliance.

Figure 16:
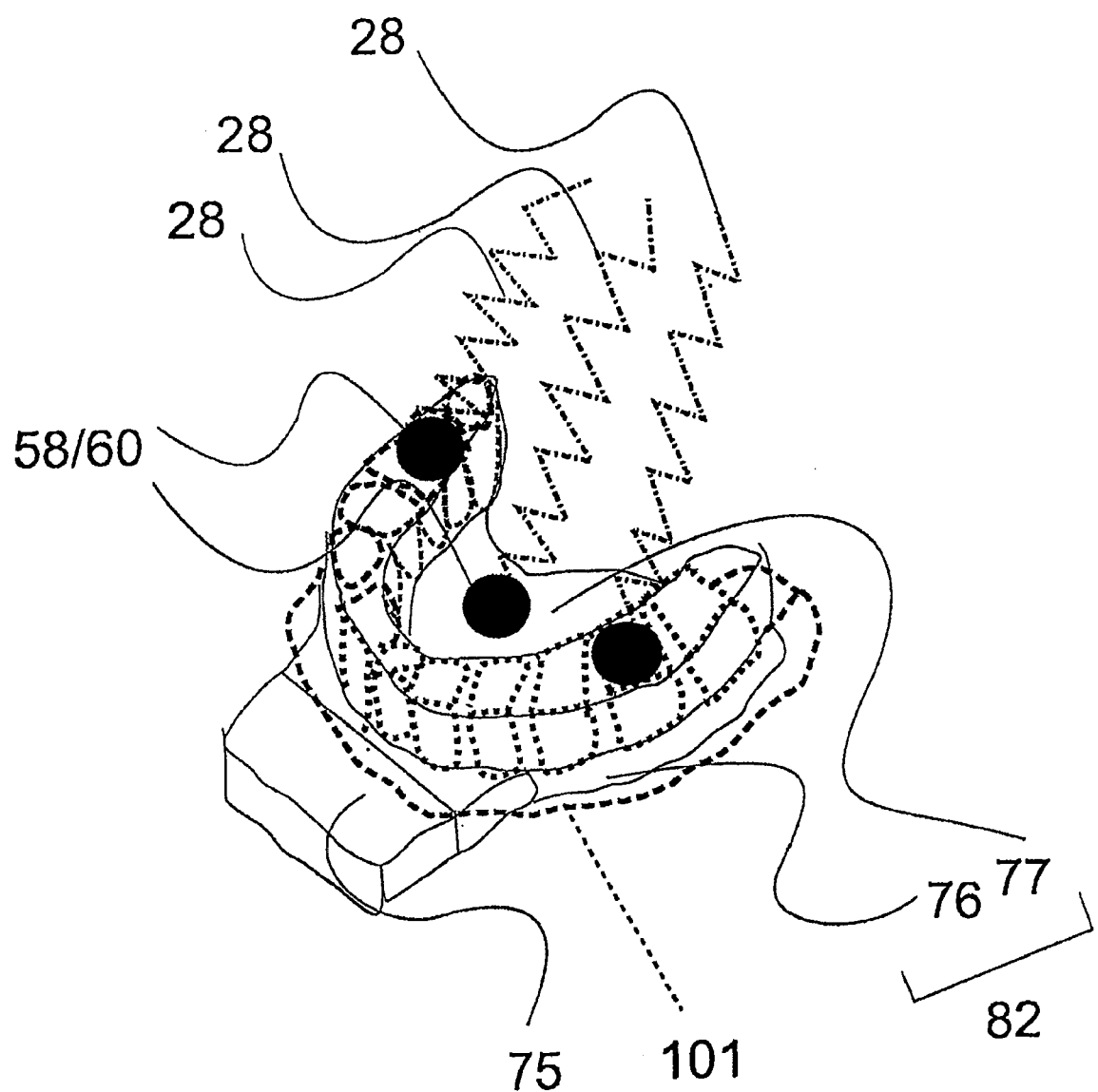
FIG. 16 example of a dental impression, mouth guard, or "bite block".

FIG. 16 example of a dental impression, mouth guard, or "bite block". Although the impression is only that of the upper teeth/upper alveolar ridge, a system that uses an impression of the lower teeth with or without that of the upper teeth can be integrated. Furthermore, one could use a bite block that does not contain a custom impression but consists of a noncustomized rectangular or other block onto which the patient bites. This figure also demonstrates the electronic sensors in place.

FIG. 16 is an example of a commercially available dental impression 82, mouthpiece, "bite block" or mouth guard. The figure demonstrates a view of the patient's upper teeth and hard palate, looking up from below the level of the patient's mouth. This appliance 82 is composed of the alveolar ridge/teeth element 76 as well as the hard palate portion 77. Demonstrated in the figure is the patient's maxilla 101 containing the upper alveolar ridge, upper teeth and hard palate. In between the dental appliance 82 and the maxilla 101 are pressure-measuring sensors 58/60, which communicate via an electronic signal 28 to the computer 20 (not shown). In this figure, the three electronic pressure-measuring sensors 58/60 are each placed abutting right and left upper molar teeth, as well as at the hard palate. In the most common application that is used for mouthpieces in stereotactic scanning and treatment, impressions 76 and 77 are made of the upper teeth and/or upper gums and/or hard palate. Impressions of the lower teeth and/or lower gums and/or floor of mouth may be made alternatively, or in combination with the impression of the maxillary (upper) teeth, gums and hard palate. When used in combination, these are known commercially as triple trays. The impression material used can be one of a number of commercially available materials, including but not limited to silicon putty. Another commonly used dental method that can be utilized in this application is a mouth guard, which also can use a number of methods and which can make a mold of a patient's upper gums and hard palate as well as the mandible, lower teeth and floor of mouth. The pressure-measuring sensors 58/60 can be placed in any of the aforementioned locations at the time that the mold or dental impression is made. If wires are used to send the electronic output to the computer 20, there will be space left in the dental impression for the wires. Frame 73/79 can be omitted and the dental impression or appliance used to track the movement of the patient's oral cavity (and by extension the skull) via fiducial markers (composed of metallic or gold seeds, an optical marker which is tracked by cameras, or electromagnetic beacons) which are commercially available and are attached to the dental impression with extension 75. In this case, the sensors would be used to ascertain the fidelity of the patient's bite. Otherwise, extension 75 is used to rigidly connect the dental impression with the frame 73/79. Although a dental impression is shown in this figure, any dental appliance (moldable, a non-custom block, etc) that is used to immobilize a patient or to track a patient's movement may incorporate the invention.

Figure 17:
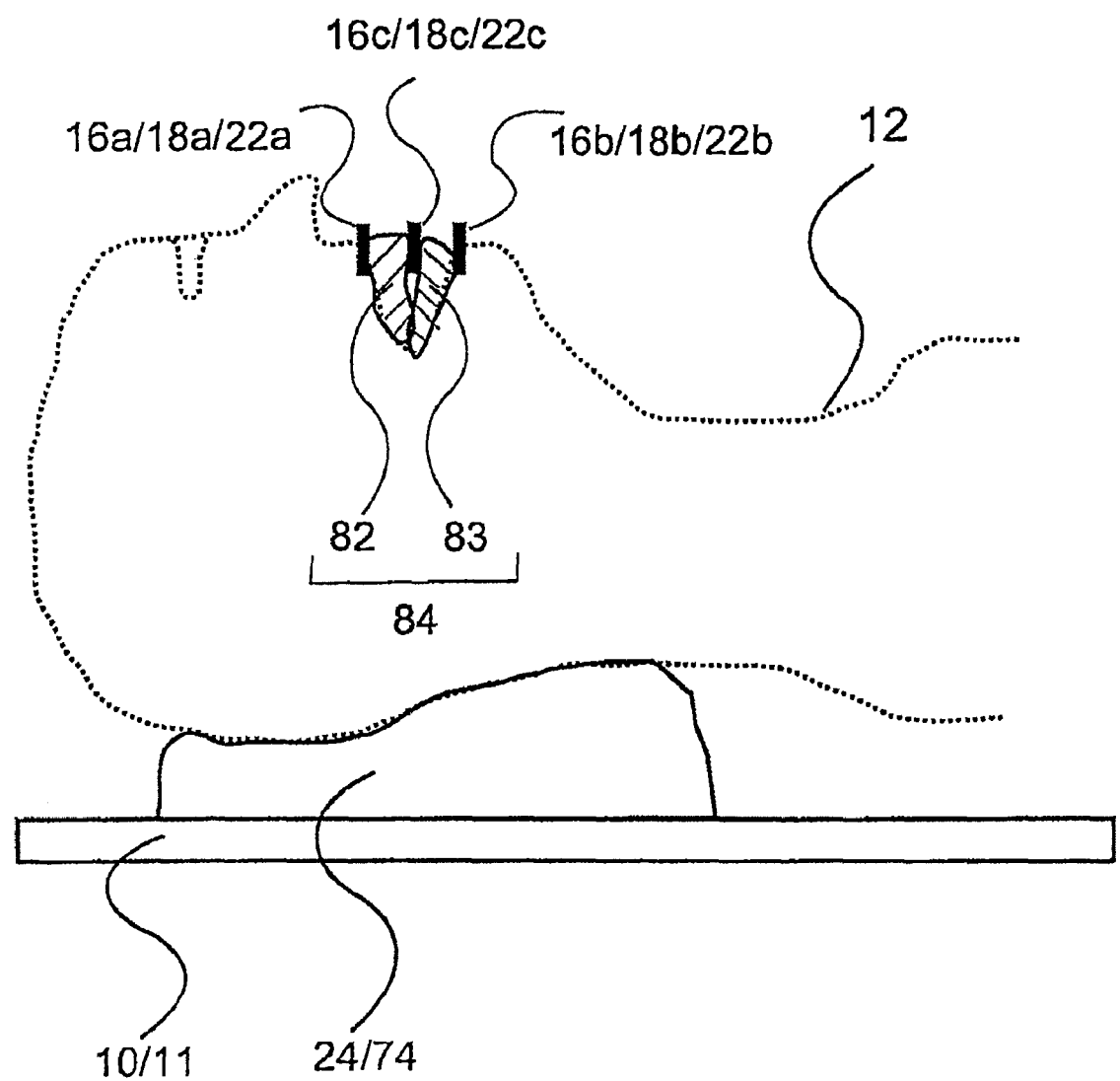
FIG. 17 example of a bite block with a sensor that is inserted into a slot in between dental impressions of the upper and lower teeth/alveolar ridges, as well as between the upper bite block and the maxilla and the lower bite block and the mandibular ridge/teeth.

FIG. 17 example of a bite block with a sensor that is inserted into a slot in between dental impressions of the upper and lower teeth/alveolar ridges, as well as between the upper bite block and the maxilla and the lower bite block and the mandibular ridge/teeth.

FIG. 17 is a side view of a patient who has been immobilized for a diagnostic or interventional radiology scan, nuclear medicine scan, angiography scan, or radiation treatment. The patient 12 has both a maxillary (upper ridge) 82 and mandibular (lower ridge) 83 impression that has been made. These may be connected to a ridge frame (not shown here), directly to a GTC or other stereotactic head-frame, or a fiducial marker array (not shown) that is used to track the position of the skull by using the fiducials connected to the dental impression as a surrogate as known to those of skill in the art. Also not shown is an optional thermoplastic mask or other mold of the anterior portion of the skull, which would aid in immobilization. There are 3 sets of electronic pressure-measuring sensors that are shown to have been placed: between the maxillary dental impression 82 and the patient 12 (16a/18a/22a), between the mandibular dental impression 83 and the patient 12 (16b/18b,22b), and between the two dental impressions 82 83 (16c/18c/22c). Alternatively, the maxillary and mandibular dental impressions can be made as a unit 84 including but not limited to a partial or full triple tray. The pressure sensors are connected electronically to a computer (not shown), which records and displays a quantitative measure of the amount of pressure being exerted on the pressure sensors. Each sensor may be an individual sensor, a grid of sensors or a strip of sensors, which is commercially available. Any combination of 82 may be used (76 and/or 77), with or without a partial or full mandibular impression 83; and quantity and pattern of pressure readings from the sensors would be used to track any movement or variation of position during scan and/or treatment, as well as any variation between any scan and/or treatment days in initial patient positioning setup. As noted in previous figures, a standard neck-rest 24 or customized mold 74 of the posterior skull and/or posterior neck may be used.

FIG. 18 a flowchart that demonstrates how a patient would receive a diagnostic scan, radiation treatment, and any subsequent scans using the invention.

Figure 18A:
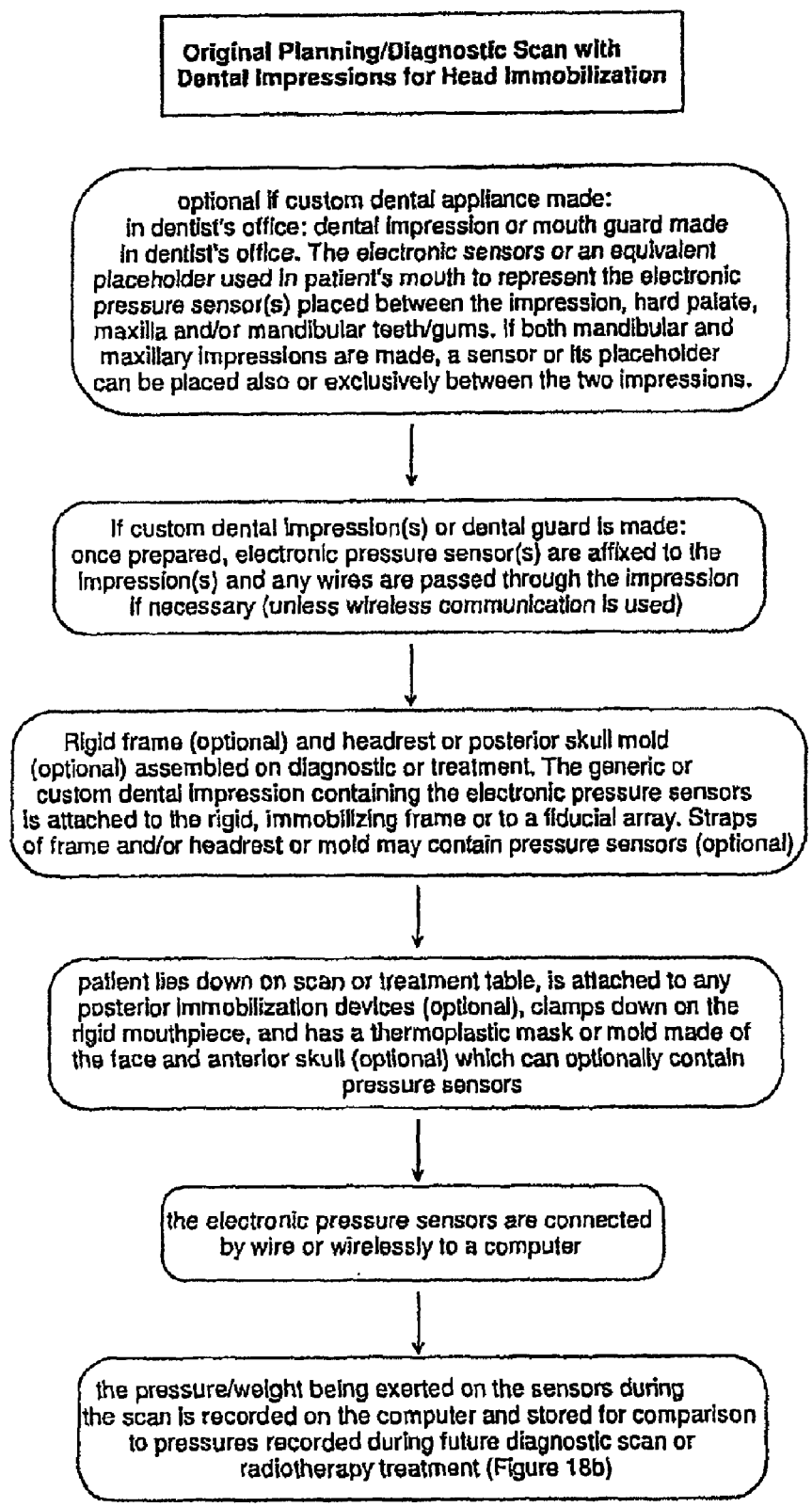
FIG. 18a shows the steps taken during a planning scan.
Figure 18B:
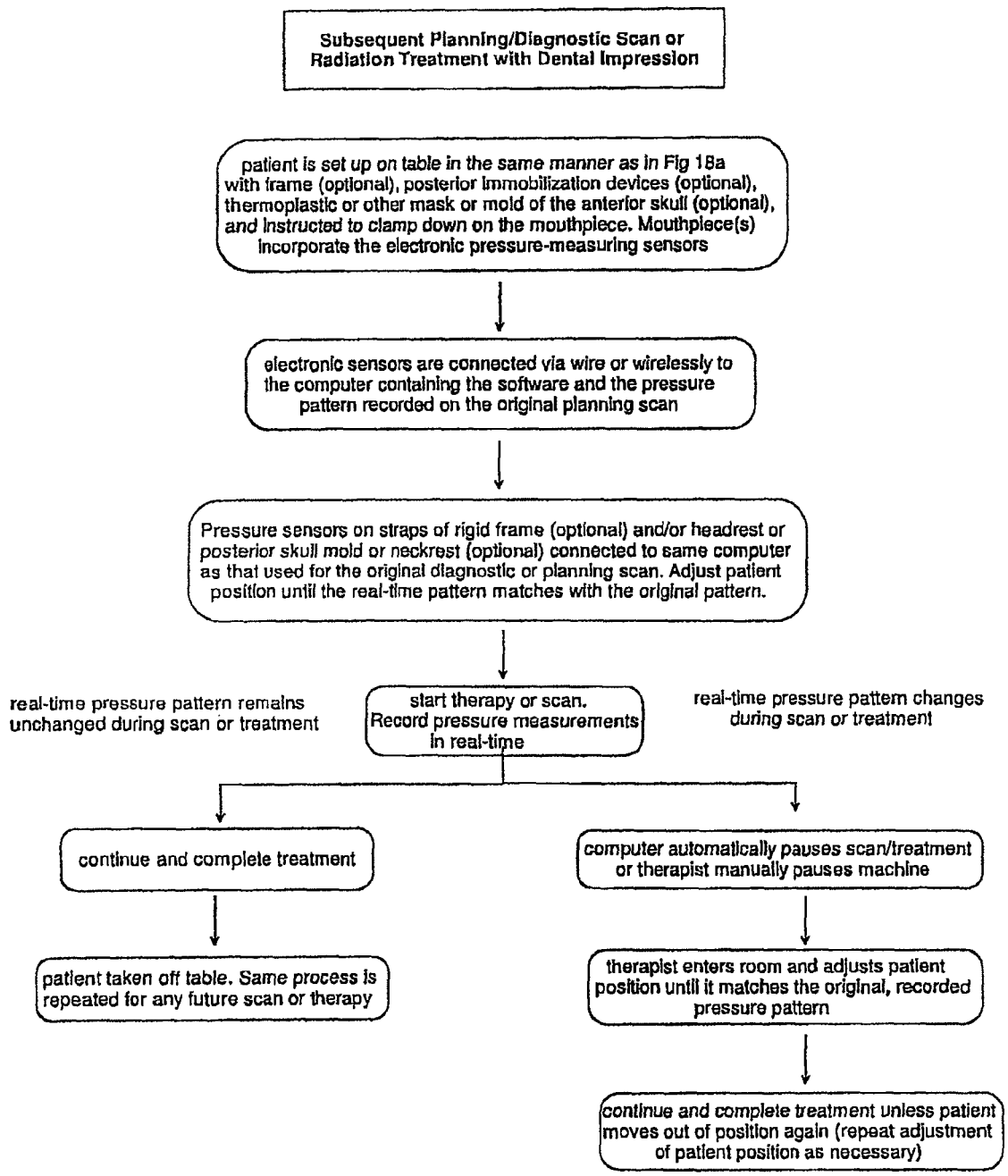
FIG. 18b shows the steps taken during a subsequent scan, or during a radiotherapeutic or other treatment that requires complete and accurate stereotactic reproduction of the patient's position recorded during the initial scan (represented in FIG. 18a).

FIG. 18 is a flowchart which shows a likely implementation of this invention. FIG. 18a shows the steps taken during a planning scan. FIG. 18b shows the steps taken during a subsequent scan, or during a radiotherapeutic or other treatment that requires complete and accurate stereotactic reproduction of the patient's position recorded during the initial scan (represented in FIG. 18a).

The embodiment to reduce variability in patient positioning, track patient motion in real-time, and/or to track respiratory motion in patients who are positioned in prone or decubitus position is described herein.

Figure 19:
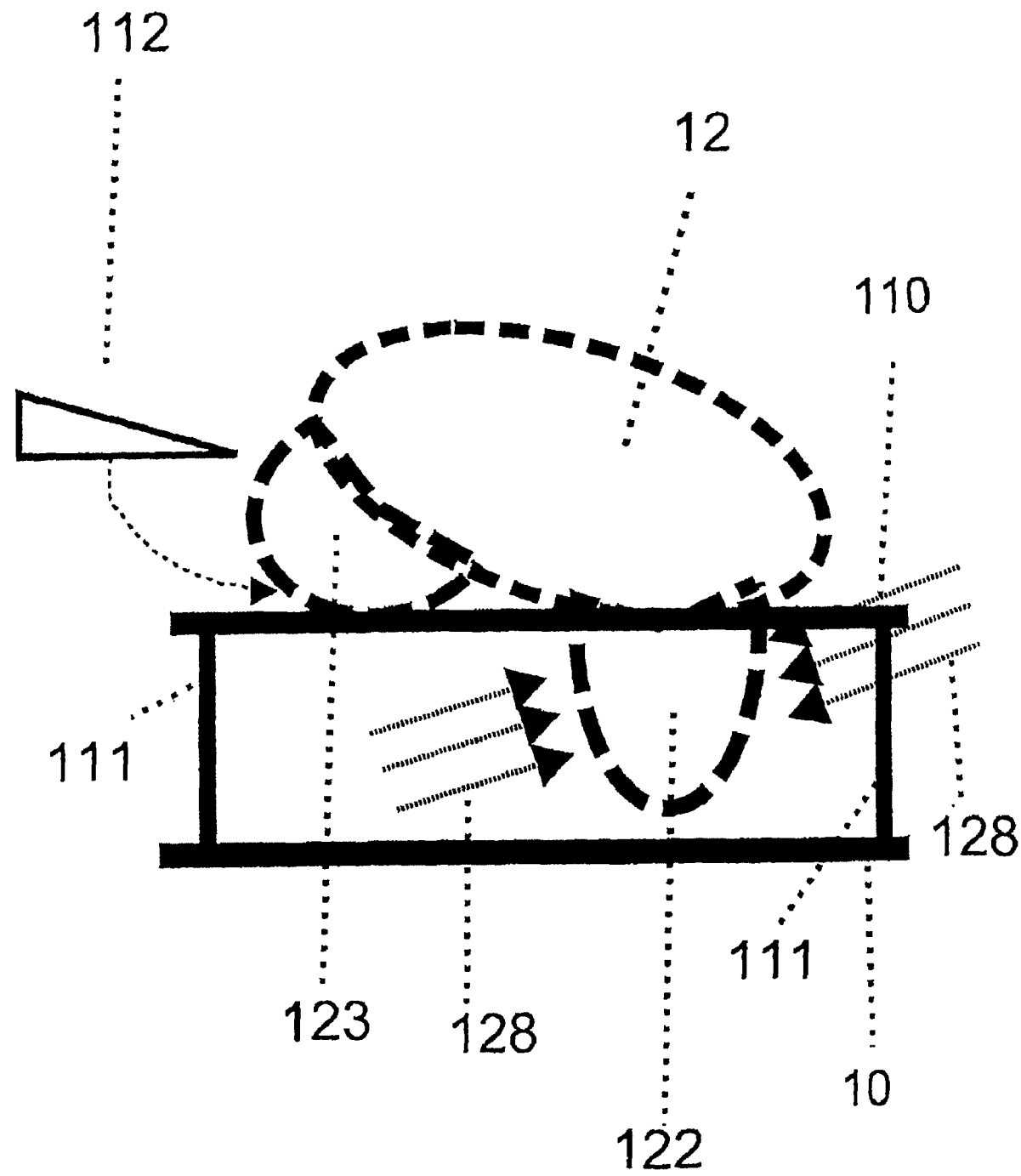
FIG. 19 describes how a patient is commonly positioned for prone therapy in a manner that is the current embodiment of the technique, in this case showing how a patient is positioned for prone breast radiotherapy.
Figure 20:
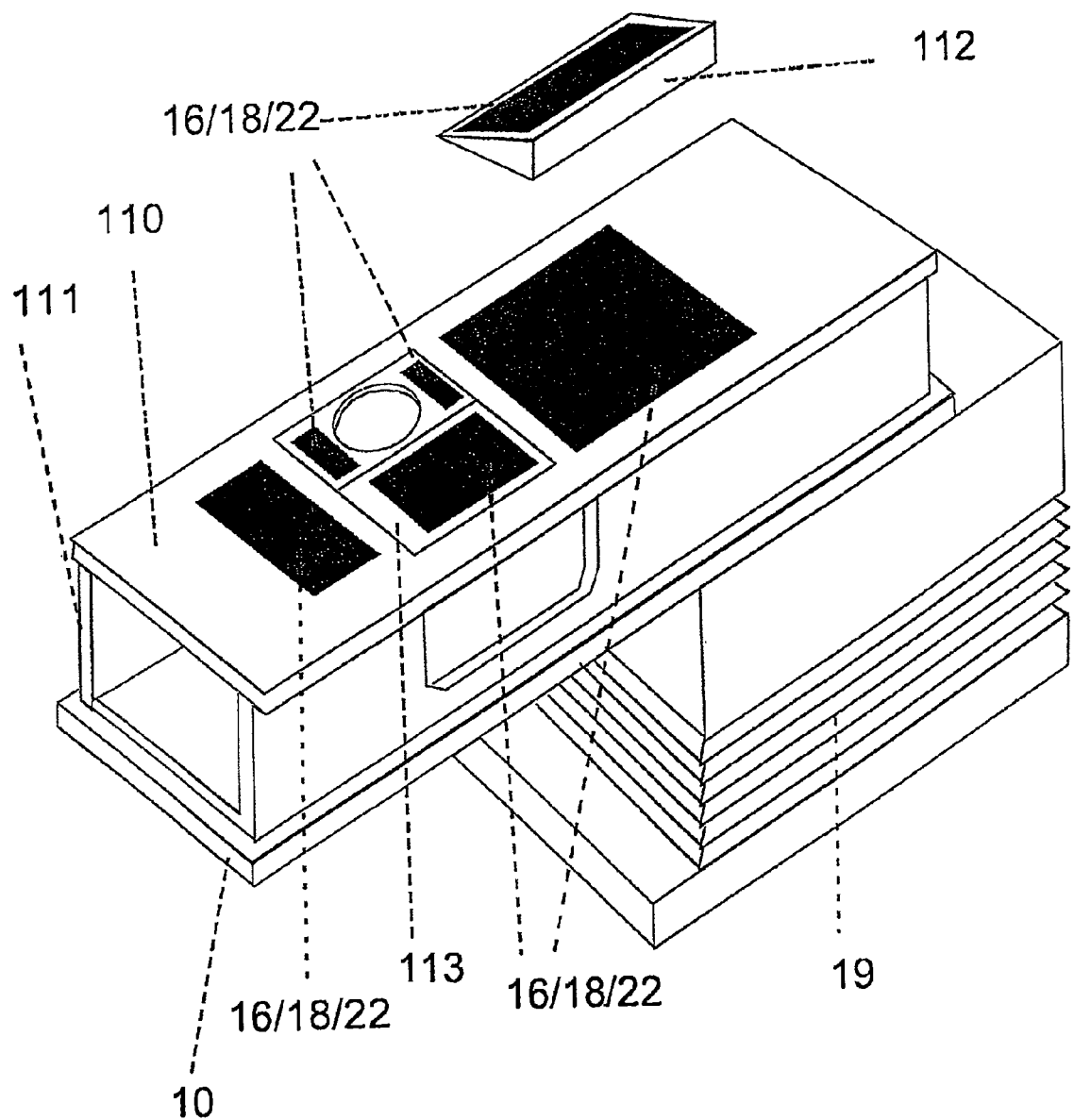
FIG. 20 is a slanted view of any commercially-available prone breast radiotherapy positioning device on top of a radiotherapy scanning, diagnostic radiology or nuclear medicine scanning table.

FIG. 19 describes how a patient is commonly positioned for prone therapy in a manner that is the current embodiment of the technique, in this case showing how a patient is positioned for prone breast radiotherapy. The radiology, nuclear medicine or radiation therapy technologist positions the patient on their stomach on an elevated platform 110 which is supported by pillars or a rigid wall 111 often perpendicular to and always above the scan or treatment table 10. The breast that is being scanned or treated 122 is placed through an opening in the elevated platform 110. The other breast 123 is placed directly on the elevated platform 110 or may be supported by a wedge 112 or other shape including a custom-forming Vac-Lok device, in order to rotate the patient so that the breast is hanging even further away from other portions of the patient's anatomy including the chest wall and the heart. The wedge may approximate the length of the contralateral breast that is being supported, or may extend through all or a part of the length of the patient's body or the elevated platform. In patients being treated with radiotherapy, the treatment beams are often administered with two opposing beams 128, although other beam arrangements are possible.

FIG. 19 is an axial (head-on) view of commercially available systems that are used for prone breast radiotherapy. These systems usually consist of an elevated platform which has an opening on one side. The patient lies flat on her stomach, with the breast being scanned or treated hanging through the opening.

FIG. 20 is a slanted view of any commercially-available prone breast radiotherapy positioning device on top of a radiotherapy scanning, diagnostic radiology or nuclear medicine scanning table. This demonstrates the same commercially-available immobilization device that is embodied in FIG. 1, but with the addition of the pressure sensors.

FIG. 20 describes how the invention is to be incorporated into this commercially-available apparatus. Demonstrated here is a slanted view of the commercially-available positioning devices that are shown in FIG. 1. The table 10 is supported by a mechanical device 19 that permits the table to be moved up, down, in and out, and which is a component of almost every standard diagnostic scanning or radiation therapy table. Above table 10 is the elevated platform 110 which is supported by pillars or a vertically oriented platform 111. Commonly, there is an opening at the side so that the breast being treated would be visible from these angles, and the position of the breast confirmed by the technician or therapist; in commercial practice, this is often by alignment with tattoos or marks that have been placed on the patient, although other techniques such as external breast contour mapping can be performed. Also shown is a wedge 112 which may be placed on the elevated platform 110 or may replace an insert into the platform 113 which is used to support the breast that is not being scanned or treated. The pressure sensors 16/18/22 may be incorporated into any or all of the elements of the commercially-available apparatus for patient positioning for prone breast therapy or scanning described here. The real-time, quantitative pressure sensors are attached to an electronic receiving and recording device which is used to ascertain the position of the patient. In an initial diagnostic or planning scan, these readings can be used to place the patient in an optimal position to have the untreated breast pushed out of the way of the radiotherapy beams, and to optimize the rotation of the patient so that the treated breast is as far away from the lung, heart and other normal structures as possible. These readings are also stored for future reference. On future scanning or radiotherapy treatment sessions, the sensor readings are displayed to the technician or therapist and interpreted by the software in real-time, and the position of the patient is modified accordingly so that they are in the same position as during the initial diagnostic or planning scan. The sensors can also be used to replicate a patient's position between a diagnostic scan and any radiotherapy session, between the radiotherapy planning session and any radiotherapy treatment session, and between any two or more radiotherapy treatment sessions. While the patient is undergoing treatment, the sensors can be used to determine if the patient is moving; if this is the case, the receiving computer can output a signal to either the therapist/technician outlining the extent of this movement and/or any recommendations for treatment interruption, or a signal directly to the scanning or treatment machine noting the need for temporary interruption of the scan or treatment. The sensors may be used to monitor the patient's phase in the respiratory cycle in these patients placed in the prone or decubitus position. The pressure sensors may also be used in any specialized diagnostic or treatment machine in which the prone tissue and patient positioning device is inseparable from a tabletop 10, which may or may not incorporate a table positioning apparatus 19.

Figure 21:
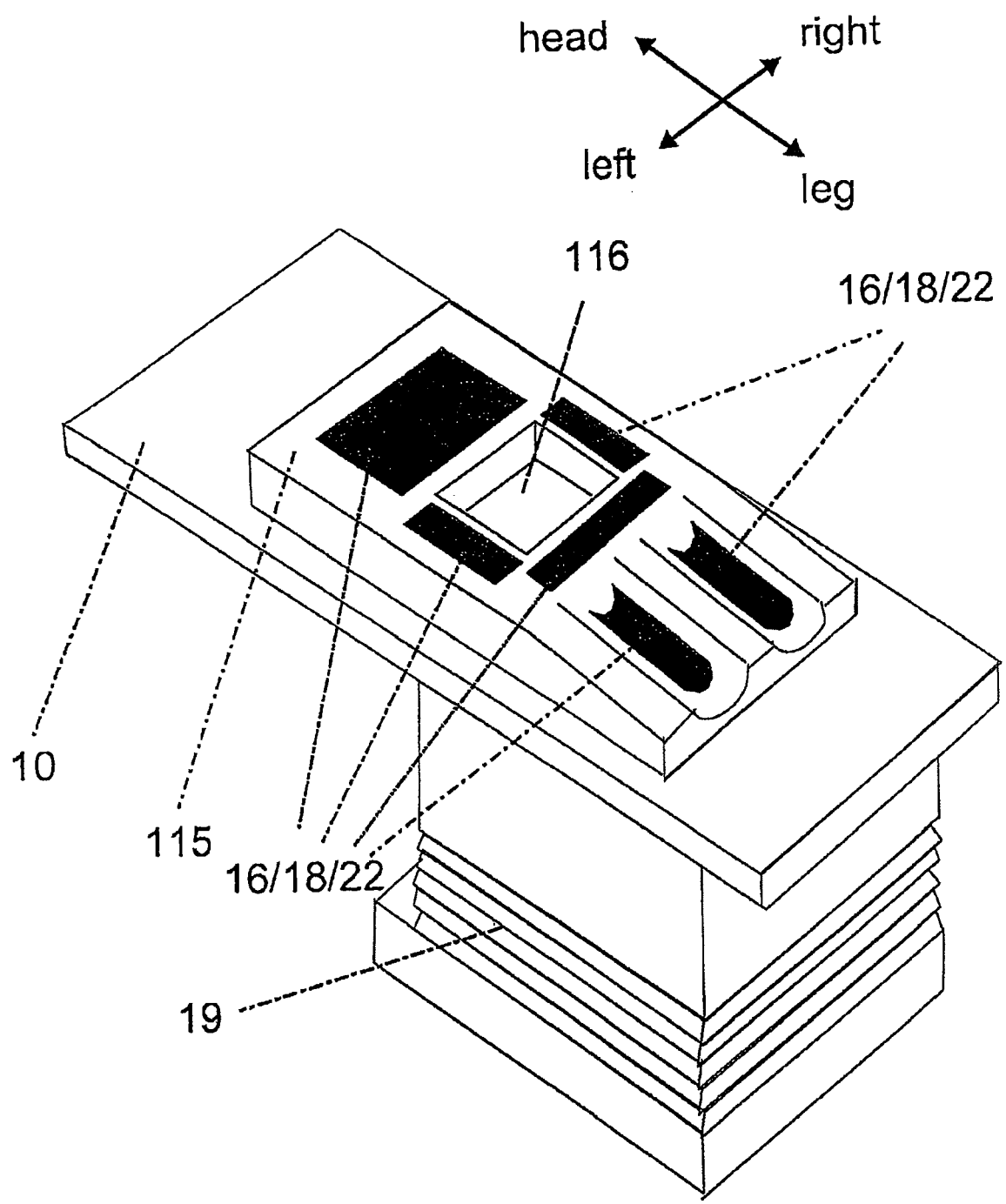
FIG. 21 demonstrates a commercially available prone belly board commonly used in the treatment of the abdomen or pelvis in a patient.

FIG. 21 is a slanted view of any commercially-available prone abdominal and pelvic belly board device. The utility of the pressure sensors in this application is the same as that described for the prone breast radiotherapy positioning device.

FIG. 21 demonstrates a commercially available prone belly board 115, commonly used in the treatment of the abdomen or pelvis in a patient. This is also commonly placed on top of a diagnostic scanning, radiotherapy scanning, or radiotherapy treatment table 10. While advantageous for pushing the intestines out of the path of radiation beams, the prone belly board has known positioning uncertainties often exceeding those of patients lying on their backs, as is known to those of skill in the art. The patient lies prone above this device, and their abdominal pannus falls into the space 116 that is built into the belly board 115. The belly board frequently contains semi-circular indentations into which the legs are placed, shown in this figure. Sensors 16/18/22 are to be used in order to achieve optimal patient positioning for a scan, and are placed between the belly board and the patient. The original recorded readings from the sensors can be referenced in future scans or treatment sessions in order to reproduce patient positioning as described in prior figures for supine positioning as well as prone breast positioning in this application; namely, optimal patient positioning on initial scan, reproduction of patient position between treatments, monitoring of real-time and recorded patient movement during treatment, and monitoring and electronic output to the scanning or treatment machine depending on the phase of the respiratory cycle or respiratory excursion as determined by the quantitative measurements obtained from the pressure sensors.

The system includes a radiotherapy treatment or diagnostic radiology/nuclear medicine scanning table in common commercial use 10 that a patient (12) is place upon. Also, included is a rigid board 11 which is attached to the treatment table with device 13. Other accessories may be placed into this board or directly onto the table 10 and held rigidly in place, as is standard commercial practice.

Protrusions, hooks or other connectors 13 (in common commercial use) can be affixed to a flat surface, board or immobilizing device incorporating the pressure-mapping grids. These protrusions or hooks are used to mount or slot the surface or board onto receiving devices or connectors 14 at the sides of the treatment or diagnostic table 10.

Indentations, receiving bars, or other connectors 14 that are at the sides of the table 10 (in common commercial use), which are receiving devices for protrusions or hooks 13 to mount or slot in a flat surface, board or immobilizing device that incorporate a pressure-mapping sensor grid, or other device to immobilize a patient onto the treatment or diagnostic radiology table. Other accessories may be placed into this board and held rigidly in place, as is standard commercial practice.

An example of an irregularly shaped grid of pressure sensors on a flat surface 16, onto which the patient places a portion or entirety of their body is shown in the Figures. The shape can be circular, ellipsoid, or irregular in any dimension. It may consist of a single sensor element or sensor grid, or it may consist of one or several strip(s) of pressure sensors aligned along either the transverse, diagonal or longitudinal axis of the immobilization device. Each sensing element 26 of the sensor grid 16/18/22/58/60 is spaced from a submillimeter distance to tens of centimeters apart from the adjacent sensing element(s). Multiple sensor arrays may be used simultaneously, in any portion of the body.

A rigid, thin board onto which is attached to (either at time of manufacture, or subsequent to manufacture with a thin, flexible mat either glued or otherwise attached to the rigid board), a grid of pressure-sensitive sensors 16/18 is shown in the Figures.

A square or rectangular grid of pressure sensors on a flat surface wherein each sensor can be spaced from a submillimeter distance to tens of centimeters apart from the adjacent sensor 16 is shown.

A computer 20 can receive the output from the pressure sensors. The computer can be used to visually compare different days' worth of data, as well as to store the weight-bearing patterns obtained from the pressure sensors. The therapist may change the patient's position based on this data. The computer may receive output from one or a multitude of individual strip(s) or grid(s) of pressure measuring sensors.

An embodiment of the computer in 20 which receives the output 28 from the pressure sensors (mode 21). This computer will store or have stored the phase of respiration that corresponds with the different phases of the respiratory cycle or respiratory excursion. It will then send a signal to the computer controlling the radiotherapy linear accelerator 40 or diagnostic scanner 42 via a signal 30 depending on the particular phase of the respiratory cycle or excursion detected based on the surrogate of change in weight-bearing pattern. For radiotherapy, this would lead to the beam of the linear accelerator 40 being administered to the patient based on the cycle or level of excursion or breath hold. For diagnostic imaging, a common embodiment would be placing a scanned image into a bin with an electronic tag that indicates the respiratory phase or level of respiratory excursion in which the scan was taken.

An example of a grid of pressure sensors 22 that are not placed on a flat surface, in this case incorporated into or placed on top of an irregularly shaped surface 24, 25 or 74 molded to the patient's posterior body contour is shown. It is an embodiment of 16 or 18, but the sensors are not on a flat surface, and is often incorporated into a flexible and pliable backing or case.

An example of a head and/or neck rest 24 74, which can be used to immobilize the patient's head and/or neck from the posterior aspect is shown. This immobilization device may optionally incorporate pressure sensor(s) 22 at time of manufacture, or the sensor(s) may be temporarily or permanently affixed with an adhesive or mechanical connection.

A vac-lok, alpha-cradle or other mold 25 in common commercial use can be used to immobilize the posterior aspect of a patient's thorax, abdomen, pelvis, and/or extremity for a radiotherapy or diagnostic radiology/nuclear medicine scan. This immobilization device may optionally incorporate pressure sensor(s) 22 at time of manufacture, or the sensor(s) may be temporarily or permanently affixed with an adhesive or mechanical connection.

An example of components of the grid of pressure sensors 16/18/22/58/60. Wherein each square 26 spaced apart from each other represents an individual sensing element is shown.

An electronic (wired or wireless) signal 28 which can be transmitted from the grid(s) or strip(s) of sensors which sends the pressures mapped at each sensor in the grid(s), in real-time. The signal may be transmitted every few milliseconds, every few seconds, or longer intervals, depending on the limits of the particular sensor and transmitter, as well as the application (e.g., respiratory gating).

An electronic (wired or wireless) signal 30 can be transmitted from computer 20, which incorporates the signal interpreting the respiratory cycle, and controls the treating 40 or diagnosis 42 machine and/or its control module. For radiotherapy, the signal would turn the treatment beam on or off. For diagnostic radiology or nuclear medicine scan, it would control the scanning device to create a bin of images at each axial slice that corresponds with the given cycle of the patient's respiration for example. The computer 20 can also receive an electronic signal from the radiotherapy or diagnostic machine, indicating when that machine is turned on; if machine activity creates electromagnetic activity that interferes with the pressure sensor readings, the computer 20 will automatically correct for these perturbations using software algorithms. A recording device 32 (e.g., computer, personal data assistant, or any other memory storage device as are known in the art) can receive an output from the pressure-mapping grid of sensors. This may also be a second or third computer that receives the same data as the primary computer, and may be in another location.

A facemask or any anteriorly-placed mask 34/66, in common commercial use, can be custom-fitted to the patient's head and/or facial and/or neck and/or upper thorax contour for the purposes of immobilization and can be used in head and/or neck embodiments of the present invention. This may or may not be omitted during the treatment or diagnostic scan.

In FIG. 12(*a*) rings 36 represent a device that immobilizes the patient's body from the anterior or sides, in common commercial use. The device may consist of flexible plastic or polycarbonate that is wrapped around the patient (in common commercial use), and then vacuumed until a tight seal is established around the patient in order to achieve immobilization. This may be omitted during radiotherapy or a diagnostic scan focused on the thorax, abdomen, pelvis, and/or extremity. Alternatively, a rigid mask 34 may be used, obviating the need for any vacuum seal to be generated.

A linear accelerator, proton beam therapy head or other device that delivers radiation for therapeutic purposes 40 is exemplified in the Figures.

Pressure or weight-bearing profile of patient on the sensing grids/strips on the day of initial planning or diagnostic/nuclear medicine scan 50 is shown.

Pressure or weight-bearing profile of patient on the sensing grids/strips on the day of subsequent diagnostic/nuclear medicine scan or radiotherapy treatment 52 is shown (often in real-time) with representation on patient's body of placement of weight-sensing grid(s) 54.

An on-screen button selected by the therapist 56 can assist in aligning a patient with the reference pattern and can transpose an outline of the stored 50 pressure peak(s) on the real-time pressure graph 52. This could also prompt the program to instruct the user to shift or rotate the patient in a specific direction or along a specific axis or automatically shift or rotate the patient. Such an automatic shift may be electronically outputted to a mechanical device on the table which can rotate or translate the patient as is known to those with skill in the art.

A single sensor in a housing 58, or a collection of pressure-measuring sensors arrayed in a rectangular, circular, elliptical, strip(s) or any irregular shape 60 can be placed directly onto the skin of the patient prior to the placement of the mask or mold onto the patient. These sensor(s) are typically flexible and will usually have an adhesive backing which is used to attach to the mask once it becomes rigid which conforms to the shape of the patient's head, face, neck, and/or any other body contour. A temperature-sensitive adhesive may be used, such that the sensor(s) can be easily detached and reattached to the mask. An insert may be placed between the mask and the sensor(s) if it is found that the pressure reading obtained from the sensor(s) is too low, or the mask may be remolded if that is the case. If arrayed as a grid or other arrangement of multiple sensors in a single housing, each sensor element 26 is spaced from a submillimeter distance to tens of centimeters apart from the adjacent sensor element. The sensors will typically be arrayed inside a rubber or other flexible material which can bend, and the entire sensor including the casing could be from less than 1 millimeter to several centimeters thick.

The sensor 58 or sensor array 60 can be attached with an adhesive with which the sensor, array, grid, or strip(s) of sensors can be attached to the mold or mask of the patient's body contour. This glue or adhesive may be applied onto the backing of the pressure-measuring sensor(s) or their flexible casing when the mask is fitted to the patient (usually, at the time of simulation or initial diagnostic scan), or it may be incorporated into the sensor(s) as an adhesive backing which is protected by a non-stick wax paper or other temporary protective covering which is removed when the mask is fitted to the patient. Temperature-sensitive or other adhesives may be used for purposes of each detachment and reattachment as needed. Other hardware or devices to attach sensor(s) to the body-conforming mask or mold may also be used.

A collection of pressure-measuring sensor elements arrayed in a rectangular, circular, elliptical, strip(s) (arranged in a transverse, longitudinal or diagonal direction) or any irregular shape 58/60 can be incorporated into the mask or mold prior to stretching the flexible mask or mold material to conform to the contours of the patient's head, face, neck, chest, abdomen, or other body contour. Each individual sensor in an array can be spaced from a submillimeter distance to tens of centimeters apart from the adjacent sensor point. The sensors will typically be arrayed inside a rubber or other flexible material which can bend, and which could be from less than 1 millimeter to several centimeters thick. All or a portion of the sensor(s) may be attached to the mask/mold at the time of manufacture.

An attachment point for a strip or larger array of pressure-measuring sensors which are built or embedded into a mold or a deformable mask 61. If the strip or grid of sensors is too large, it may be necessary to have only a portion of the sensor(s) attached to the deformable mask/mold material since the mask material will stretch to fit the patient body contour, while the sensor(s) cannot stretch. The edges of the sensor grid(s) or strip(s) can later be affixed to the mask with an adhesive tape, glue, or other attachment device.

An embodiment of the computer in which the output from the pressure sensors can be used to determine the position of the larynx and whether a person is swallowing 62 is shown. Depending on this, the computer may send an electronic signal to the computer controlling the radiotherapy machine to pause the radiation beam or to the diagnostic radiology or nuclear medicine scanner to place the images associated with a particular phase of swallowing into a bin with an electronic tag that indicates the phase of swallowing in which the scan was taken.

An example of a head and/or neck rest 24 can be used to immobilize the patient's head and/or neck from the posterior aspect. The head and/or neck rest can be a noncustomized head and neck cradle, customized vac-loc, customized alpha-cradle or other mold in common commercial use, and can be used to immobilize the posterior aspect of a patient's head and/or neck.

Reference No. 65 (FIG. 3*a*) is an example of components of the grid of pressure sensors. Each square represents an individual sensing element 26 which is spaced anywhere from submillimeter distances to tens or more centimeters apart from the adjacent pressure-measuring sensor.

Reference No. 34/66 exemplifies a mask, in common commercial use, which is custom-fitted to the contour of a patient's body part. The patient will be immobilized between the mask and the table, and a neck-rest or customized mold may optionally be placed between the table and the patient. The mask can include the head and/or facial and/or neck and/or upper thorax contour or abdominal or pelvic area for the purposes of immobilization. The mask incorporates the features 71 and 72, as well as other features which are not shown which are used in common commercial practice in order to immobilize the object directly onto the table 10, a rigid board 11 which attaches to the table, or other rigid device which is fixed in relation to the table (not shown).

A commercially available apparatus 70 which consists of a frame 38 used to fix the device in space, and compresses the abdomen via a screw or ratcheting device 39 in order to obtain control of and decrease motion of the diaphragm. It consists of the frame 38 which rigidly locks into place on a mold of the patient's posterior body contour 25 or directly onto the table 10, the floor, or another device 11 which itself is fixed relative to the table. The frame is connected to a device 39 which screws or ratchets down, which acts to compress the abdomen, usually but not necessarily at the level of the xiphoid process. The part of this apparatus which contacts the abdomen may contain a pressure-measuring sensor as described in this invention. In an embodiment of the invention, a single sensor or a collection of pressure-measuring sensors 67 arrayed in a rectangular, circular, elliptical, strip(s) (arranged in a transverse, longitudinal or diagonal direction) or any irregular shape and number of sensing elements can be incorporated into the rigid screw 39 or other device which compresses the abdomen to decrease diaphragm and abdominal motion with respiration. The sensor(s) can be placed in a flexible or rigid material which would either be affixed to the compression device 39 at the time of manufacture, or be attached to the compression device via an adhesive or a direct mechanical link.

A radiotherapy treatment machine 40 can treat the patient with x-ray, gamma rays, electrons, protons, neutrons, heavy ions, or any other type of radiation. For the purposes of this invention, can be interchanged with diagnostic radiology or nuclear medicine scanning device 42, which can include but would not be limited to CT, MRI, MRS, PET/PET-CT, or SPECT. For purposes of this invention, these can be interchanged with 40.

Reference No. 36 exemplifies a flexible device (commercially available), which wraps around the patient and is used to achieve a vacuum seal and immobilization of the patient. In commercial practice, this will most commonly consist of but is not limited to the BodyFix device (Medical Intelligence, Schwabmünchen Germany). Alternatively, a rigid device 34 (commercially available or currently in use) that utilizes a thermoplastic mask, body cast, VacLok, or any rigid stereotactic body frame can be used to immobilize the patient from the side and/or front. This frame may not necessarily have to utilize vacuum-based fixation or fixation with anterior compression, although either or both could be accommodated.

Reference No. 70 (FIG. 12*b*) exemplifies an additional device in the context of 50 which achieves further abdominal compression to limit abdominal, thoracic and diaphragm motion which may take place during respiration. The system shown in this diagram is an optional component of the Medical Intelligence BodyFix system, but any commercially available system that contains different components but attains the same goal of abdominal compression can be used.

A rigid frame 71 is a component of the custom facemask 34/66 or body mask 34/66, onto which the formable material 72 which can conform to the body contour and become rigid (usually thermoplastic) to the body is attached. This is then mounted onto the table as noted for mask 34/66. In the case of the thermoplastic material in common commercial practice, it is heated in a water bath in order to become flexible although any method to make the material in the mask/mold conform to the patient's head, facial and/or neck contour could be used. The mask/mold then becomes rigid. This material may 66 or may not 34 incorporate the pressure-measuring sensors 58/60 at the time of manufacture.

Part of the radiotherapy treatment or scanning machine supports the table and allows the table to be moved up, down, and into and out of the treatment or scanning machine 19. Although not shown in all figures, it is a standard component of radiotherapy or diagnostic scanning tables 10. The output from the computer 20 can also be used to move any robotic platform that automatically translates or rotates based on the suggested patient movement. Although any such robotic system can be used, one common system that could be used would be the HexaPod system (Elekta, Stockholm, Sweden).

Platform 110 elevated above radiotherapy table on which patient is positioned, usually for prone breast radiotherapy or scanning, as a component of one of a number of commercially available positioning systems can have sensors 16/18/58/60/22, described herein affixed to this platform underneath the arms, abdomen, pelvis, thorax, or contralateral untreated breast.

The elevated platform is suspended above a side load-bearing structures 111. This commonly contains an opening through which the radiotherapy or diagnostic scanning beams can pass, and which the therapist can check to ascertain correct positioning of the breast that is being scanned or treated as per standard commercial practice.

Wedge 112, which may have a straight or curved surface, may be placed on top of the platform and underneath the patient to further rotate the patient. The wedge may be the entire length or a portion of the patient, and will have a component that is placed underneath the contralateral untreated breast. The wedge, if used, may contain the pressure sensors 16/18/22. The wedge may be used in lieu of insert 113 or may be placed directly on the elevated platform 110 or insert 113. An alternative embodiment of the wedge can be a customized mold, which may or may not contain the pressure sensors described.

A removable rectangular or circular platform 113 can be moved to the opposite site, which supports the breast that is not being treated or scanned.

A commercially-available belly board 115 is shown. Although several variations exist, they all consist of a patient lying in prone position with an opening for the abdomen. This is often placed on top of a treatment or scanning table in a similar manner to the prone breast device.

An opening 116 in prone belly board through which the abdominal pannus is placed with the patient in prone position. In patients being treated with radiotherapy to the abdominal or pelvic areas, this can decrease the amount of normal intestines being treated with high doses of radiation.

A breast 122 being treated with radiotherapy or being imaged is shown, as well as a contralateral breast 123, which is being compressed away to avoid any incidental radiation. Pressure sensors may be placed underneath the untreated breast 123 to permit its reproducible positioning during daily radiotherapy.

Representation of radiotherapy or diagnostic mammography beams are shown to treat or image the breast. MRI and nuclear imaging applications can also be used in this manner.

One skilled in the art will appreciate that numerous equivalents of the foregoing materials and equipment are readily available and that these Examples may be modified in accordance with the principles hereof using no more than routine experimentation. All references cited herein, including patents, patent applications, and publications, are hereby incorporated by reference in their entireties, whether previously specifically incorporated or not.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims; or in the text itself, and, each of these documents or references ("herein-cited references"), as well as each document or reference cited in each of the herein-cited references (including any manufacturer's specifications, instructions, etc.), is hereby expressly incorporated herein by reference.

REFERENCES CITED

U.S. Pat. No. 3,565,195
U.S. Pat. No. 5,531,229
U.S. Pat. No. 5,595,191
U.S. Pat. No. 6,973,202 B2
U.S. Pat. No. 5,764,723
U.S. Pat. No. 4,262,306
U.S. Pat. No. 4,846,173
U.S. Pat. No. 5,315,630
U.S. Pat. No. 5,588,430
U.S. Pat. No. 5,622,187
U.S. Pat. No. 6,279,579 B1
U.S. Pat. No. 7,199,382 B2
U.S. Pat. No. 5,727,554
U.S. Pat. No. 6,621,889 B1
U.S. Pat. No. 3,565,195
U.S. Pat. No. 4,827,763
U.S. Pat. No. 4,830,461
U.S. Pat. No. 5,010,772
U.S. Pat. No. 5,693,886
U.S. Pat. No. 5,796,059
U.S. Pat. No. 5,930,152
U.S. Pat. No. 5,983,727
U.S. Pat. No. 6,847,391 B1
U.S. Pat. No. 7,030,764 B2
U.S. Pat. No. 5,775,337
U.S. Pat. No. 6,826,423
U.S. Pat. No. 7,073,508 B2
U.S. Pat. No. 4,905,267
U.S. Pat. No. 3,565,195
U.S. Pat. No. 5,531,229
U.S. Pat. No. 5,595,191
U.S. Pat. 2004/0015176 A1
U.S. Pat. No. 5,588,430
U.S. Pat. No. 4,846,173
Li X, et al. Technical and dosimetric aspects of respiratory gating using a pressure-sensor motion monitoring system. Medical Physics 33(1); 145-154, 2006, is incorporated herein by reference in its entirety.

Ashruf C, Thin flexible pressure sensors. Sensor Review 22(4); 322-327, 2002, is incorporated herein by reference in its entirety.

Hamlet S, Larynx motion associated with swallowing during radiation therapy. Int J Radiat Oncol Biol Phys 1994;28: 467-70, is incorporated herein by reference.

Kooy H M, Dunbar S F<Tarbell, N J et al. Adaptation and Verification of the Relocatable Gill-Thomas-Cosman Frame in Stereotactic Radiotherapy", Int. J. Radiation Oncology Biol. Phys., 30(3); 685-691, 1998, is incorporated herein by reference.

Gill S S, Thomas D C T, Warrington A P, et al. Relocatable frame for stereotactic external beam radiotherapy. Int J Radiat Oncol Biol Phys 1991;20:599-603, is incorporated herein by reference.

Radionics XKnife Brochure description of Gill-Thomas-Cosman frame, page 8

Kim S, et al. An Immobilization system for claustrophobic patients in head-and-neck intensity-modulated radiation therapy. Int. J. Radiation Oncology Biol. Phys., 59(5), 1531-1539, 2004.

U.S. Patent documents:
U.S. Pat. No. 4,051,380 Lasky
U.S. Patent 2006-0262898 Partain
U.S. Pat. No. 5,564,438 Mechant
U.S. Patent 2007-0033735A1 Formenti Martin J, Fitzpatrick K, Horan G et al. "Treatment with a belly-board device significantly reduces the volume of small bowel irradiated and results in low acute toxicity in adjuvant radiotherapy for gynecologic cancer: results of a prospective study." Radiotherapy and Oncology 74: 267-274, 2005.

Koelbl O, Richter S, Flentje M. "Influence of patient positioning on dose-volume-histogram and normal tissue complication probability for small bowel and bladder in patient receiving pelvic irradiation: a prospective study using a 3D planning system and a radiobiological model." Int Jrnl Radiation Oncol Biol Physics 45(5):1193-1198, 1999.

The invention claimed is:

1. A patient positioning system for alignment of a patient during radiation therapy and diagnostics (RTD) comprising: a patient immobilization device conformed to at least a portion of a patient's anatomy; at least one pressure sensor attached to the patient immobilization device for sensing the patient; and an external interrogator device, wherein said immobilization device transmits data to said external interrogator device and said external interrogator device analyzes said data and transmits a control output indicative of a position within the patient immobilization device of the portion of the patient's anatomy.

2. The patient positioning system of claim 1 further comprising a patient stabilizer interconnected with the immobilization device and the external interrogator device.

3. The patient positioning system of claim 1, wherein said control output comprises regulative feedback for maintaining a precise initial patient position and an accurate patient position continuously prior to, in the course of and subsequent to a medical treatment or diagnostic session.

4. The patient positioning system of claim 3, wherein said regulative feedback comprises surrogate feedback accounting for respiratory phase or excursion to deliver instructions to turn on or off an RTD unit, as a function of said respiratory phase or excursion.

5. The patient positioning system of claim 4, further comprising selectively delivering radiation to a predetermined region of a patient's anatomy comprising thoracic, abdominal and/or pelvic regions.

6. The patient positioning system of claim 3, wherein said regulative feedback comprises surrogate feedback accounting for patient movement to deliver instructions to turn on or off an RTD unit as a function of the movement.

7. The patient positioning system of claim 6 wherein the surrogate feedback accounts for patient swallowing.

8. The patient positioning system of claim 1, wherein said control output comprises regulative feedback maintaining a precise initial patient position and an accurate patient position continuously prior to, in the course of and subsequent to each of at least two medical treatment or diagnostic sessions.

9. The patient positioning system of claim 2, further comprising means for automatically manipulating said patient stabilizer to control patient position in real time according to output from said external interrogator device.

10. The patient positioning system of claim 1, wherein said at least one sensor comprises a plurality of sensors.

11. The patient positioning system of claim 1, wherein said at least one sensor is removably attached with an adhesive.

12. The patient positioning system of claim 1, wherein said at least one sensor is permanently embedded into said patient immobilization device.

13. The patient positioning system of claim 1 wherein the patient immobilization device comprises at least one of a neck rest, a customized mold of at least a portion of the patient's head, a flat surface, and a bite piece.

14. The patent positioning system of claim 1 wherein the control output is further indicative of a weight of the portion of the patient's anatomy.

15. The patient positioning system of claim 1, wherein the control output is further indicative of the size of the portion of the patient's anatomy.

16. The patient positioning system of claim 1 wherein the RTD is selected from the group consisting of radiation therapy, stereotactic radiotherapy and stereotactic radiosurgery utilizing one or more of photons, protons, neutrons and heavy ion particles; and diagnostic radiology and nuclear medicine utilizing x-ray radiographs, Computed Tomography, Magnetic Resonance Imaging, Positron Emission Tomography, and Single Photon Emission Computed Tomography.

17. The patient positioning system of claim 1 wherein the at least one pressure sensor is selected from the group consisting of capacitance, resistive, rubber, textile, haptic and piezoelectric sensors.

18. A patient positioning system for alignment of a patient for radiation therapy and diagnostics (RTD) comprising: a head and/or neck immobilization device conformed to at least a portion of the head and neck region of the patient; at least one sensor attached to the immobilization device(s) for sensing the patient; and an external interrogator device, wherein said sensor(s) attached to the immobilization device(s) transmits data to said external interrogator device and said external interrogator device analyzes said data and provides a control output indicative of a position within the patient immobilization device of the portion of the head and a neck region of the patient.

19. The patient positioning system of claim 18 further comprising a patient stabilizer interconnected with the immobilization device and the external interrogator device.

20. The patient positioning system of claim 18, further comprising means for automatically manipulating said patient stabilizer to control patient position in real time according to output from said external interrogator device.

21. The patient positioning system of claim 18, wherein said at least one sensor comprises a plurality of sensors and sensing elements.

22. The patient positioning system of claim 18, wherein said at least one sensor is removably attached with an adhesive or said at least one sensor is permanently embedded into said patient immobilization device.

23. The patient positioning system of claim 18, wherein said output comprises regulative feedback maintaining a precise initial head and neck region position and an accurate head and neck region position continuously prior to, in the course of and/or subsequent to a radiotherapy session.

24. The patient positioning system of claim 23, wherein said regulative feedback comprises surrogate feedback accounting for patient movement to deliver instructions to turn on or off an RTD unit as a function of the movement.

25. The patient positioning system of claim 18, wherein said control output comprises regulative feedback maintaining a precise initial head and neck region position and an head and neck region position continuously prior to, in the course of and subsequent to a radiotherapy session.

26. The patient positioning system of claim 23 or 25, wherein said control output comprises data as to the position of the patient's larynx and swallowing status.

27. The patient positioning system of claim 18 wherein the patient immobilization device comprises at least one of a neck rest, a customized mold of at least a portion of the patient's head, a flat surface, and a bite piece.

28. A patient positioning system for alignment of a patient during medical treatment or diagnostics comprising: a surface for placing a portion of a patient's anatomy thereon with a weight of the portion of the patient's anatomy bearing on the surface; at least one sensor attached to the surface for sensing the patient on the surface; and an external interrogator device, wherein said at least one sensor transmits data to said external interrogator device and said external interrogator device analyzes said data and transmits a control output indicative of a position of the portion of the patient's anatomy on the surface; a memory for storing the control output from a plurality of patient positioning sessions and the interrogator unit further compares the control output from first and second patient positioning sessions and generates data indicative of the differences between the patient's position during the first patient positioning session and the second patient positioning session.

* * * * *